US012797526B2

(12) United States Patent
Tsoory et al.

(10) Patent No.: US 12,797,526 B2
(45) Date of Patent: Nov. 17, 2026

(54) SMART PERITONEAL DIALYSIS DEVICE

(71) Applicant: Liberdi Ltd., Or Akiva (IL)

(72) Inventors: Hezkiah Tsoory, Maor (IL); Shahar Harari, Tel-Aviv (IL)

(73) Assignee: Liberdi Ltd., Or Akiva (IL)

( * ) Notice: Subject to any disclaimer, the term of this patent is extended or adjusted under 35 U.S.C. 154(b) by 785 days.

(21) Appl. No.: 18/049,458

(22) Filed: Oct. 25, 2022

(65) Prior Publication Data

US 2023/0072277 A1 Mar. 9, 2023

Related U.S. Application Data

(60) Division of application No. 16/480,550, filed as application No. PCT/IL2018/050117 on Feb. 1, 2018, now Pat. No. 12,220,509, which is a continuation of application No. PCT/IL2017/050117, filed on Feb. 1, 2017.

(60) Provisional application No. 62/488,944, filed on Apr. 24, 2017, provisional application No. 62/289,362, filed on Feb. 1, 2016.

(51) Int. Cl.
*A61M 1/28* (2006.01)
*A61M 5/142* (2006.01)

(52) U.S. Cl.
CPC ........ *A61M 1/282* (2014.02); *A61M 5/14228* (2013.01); *A61M 2205/3553* (2013.01); *A61M 2205/52* (2013.01); *A61M 2230/00* (2013.01)

(58) Field of Classification Search
CPC .................. A61M 1/282; A61M 1/284; A61M 1/28–288; A61M 1/14
See application file for complete search history.

(56) References Cited

U.S. PATENT DOCUMENTS

| | | | |
|---|---|---|---|
| 4,034,127 A | | 7/1977 | Busanovich et al. |
| 4,610,469 A | | 9/1986 | Wolff-Mooij |
| 4,624,664 A | | 11/1986 | Peluso et al. |
| 4,718,890 A | | 1/1988 | Peabody |
| 4,778,447 A | | 10/1988 | Velde et al. |
| 4,919,658 A | | 4/1990 | Badia |
| 4,967,754 A | | 11/1990 | Rossi |
| 5,167,816 A | | 12/1992 | Kruger et al. |
| 5,340,359 A | | 8/1994 | Segura Badia |
| 5,722,947 A | * | 3/1998 | Jeppsson ................ A61M 1/28 128/DIG. 13 |

(Continued)

FOREIGN PATENT DOCUMENTS

| | | |
|---|---|---|
| CN | 1905907 A | 1/2007 |
| CN | 102481444 A | 5/2012 |

(Continued)

OTHER PUBLICATIONS

Chinese Office Action, Chinese Patent Application CN201880091524, dated Aug. 3, 2021.

(Continued)

*Primary Examiner* — Courtney Fredrickson
(74) *Attorney, Agent, or Firm* — M&B IP Analysts, LLC

(57) ABSTRACT

A device for monitoring and/or modifying a peritoneal dialysis treatment, including a memory which stores at least one treatment protocol; a control circuitry connected to the memory, wherein said control circuitry generates a report and/or modifies the treatment if an outcome of the treatment is not a desired outcome of the treatment protocol.

17 Claims, 27 Drawing Sheets

(56) References Cited

U.S. PATENT DOCUMENTS

| | | | | |
|---|---|---|---|---|
| 5,733,503 | A | 3/1998 | Kowatsch et al. | |
| 5,743,892 | A | 4/1998 | Loh et al. | |
| 5,938,634 | A | 8/1999 | Packard | |
| 6,228,047 | B1 | 5/2001 | Dadson | |
| 7,013,928 | B2 | 3/2006 | Navis | |
| 7,890,341 | B2 | 2/2011 | McNally et al. | |
| 8,974,410 | B2 | 3/2015 | Miller et al. | |
| 9,050,411 | B2 | 6/2015 | Kelly et al. | |
| 9,050,421 | B2 | 6/2015 | Bene | |
| 9,078,972 | B2 | 7/2015 | Gupta et al. | |
| 10,071,202 | B2 | 9/2018 | Handler | |
| 10,437,958 | B2 | 10/2019 | Daniel et al. | |
| 10,744,253 | B2 | 8/2020 | Gerber et al. | |
| 2001/0012930 | A1 | 8/2001 | Ebner et al. | |
| 2002/0123715 | A1 | 9/2002 | Sorenson et al. | |
| 2003/0144647 | A1 | 7/2003 | Miyahara | |
| 2003/0216677 | A1 | 11/2003 | Pan et al. | |
| 2005/0197646 | A1 | 9/2005 | Connell et al. | |
| 2006/0015015 | A1 | 1/2006 | Kawamoto et al. | |
| 2006/0280646 | A1 | 12/2006 | Shiosawa | |
| 2008/0015487 | A1 | 1/2008 | Szamosfalvi et al. | |
| 2008/0045884 | A1 | 2/2008 | Landherr et al. | |
| 2008/0208111 | A1* | 8/2008 | Kamen | A61M 1/154 604/29 |
| 2008/0226507 | A1 | 9/2008 | Nia et al. | |
| 2009/0054743 | A1 | 2/2009 | Stewart | |
| 2009/0326513 | A1 | 12/2009 | Deutsch et al. | |
| 2010/0000040 | A1 | 1/2010 | Shaw et al. | |
| 2010/0057178 | A1 | 3/2010 | Simon | |
| 2010/0211003 | A1 | 8/2010 | Sundar et al. | |
| 2010/0226821 | A1 | 9/2010 | Ricciardi et al. | |
| 2010/0249663 | A1 | 9/2010 | Nishtala | |
| 2011/0054440 | A1 | 3/2011 | Lewis | |
| 2012/0123322 | A1* | 5/2012 | Scarpaci | A61M 1/152 250/573 |
| 2013/0131574 | A1 | 5/2013 | Cosentino et al. | |
| 2013/0184638 | A1 | 7/2013 | Scarpaci et al. | |
| 2013/0303996 | A1 | 11/2013 | Rasooly et al. | |
| 2013/0345621 | A1 | 12/2013 | Cicchello et al. | |
| 2014/0018727 | A1 | 1/2014 | Burbank et al. | |
| 2014/0094740 | A1 | 4/2014 | Lee et al. | |
| 2014/0194809 | A1 | 7/2014 | Plahey et al. | |
| 2014/0276374 | A1 | 9/2014 | Minkus | |
| 2014/0309584 | A1 | 10/2014 | Bluchel et al. | |
| 2015/0005699 | A1 | 1/2015 | Burbank et al. | |
| 2015/0013381 | A1 | 1/2015 | Duffy | |
| 2015/0038896 | A1 | 2/2015 | Yu et al. | |
| 2015/0148776 | A1 | 5/2015 | Sobue et al. | |
| 2015/0150905 | A1 | 6/2015 | Zimmeck | |
| 2015/0209499 | A1 | 7/2015 | Kelly et al. | |
| 2015/0238680 | A1 | 8/2015 | Kelly et al. | |
| 2015/0252800 | A1 | 9/2015 | Buckberry et al. | |
| 2016/0058933 | A1 | 3/2016 | Ballantyne et al. | |
| 2016/0213912 | A1 | 7/2016 | Daneluzzi | |
| 2016/0262984 | A1 | 9/2016 | Arnott et al. | |
| 2017/0136166 | A1 | 5/2017 | Chen et al. | |
| 2017/0281847 | A1 | 10/2017 | Manda et al. | |
| 2017/0319769 | A1 | 11/2017 | Wieslander et al. | |
| 2018/0021500 | A1 | 1/2018 | Gerber et al. | |
| 2018/0243547 | A1 | 8/2018 | Fox et al. | |
| 2018/0353670 | A1 | 12/2018 | Kommala et al. | |
| 2019/0125954 | A1 | 5/2019 | Mathiot et al. | |
| 2019/0287668 | A1 | 9/2019 | Tiwari et al. | |
| 2019/0341146 | A1 | 11/2019 | Kamen et al. | |
| 2019/0358387 | A1 | 11/2019 | Elbadry et al. | |
| 2019/0381231 | A1 | 12/2019 | Tsoory et al. | |
| 2020/0066415 | A1 | 2/2020 | Hettig et al. | |
| 2020/0155744 | A1 | 5/2020 | Tsoory et al. | |

FOREIGN PATENT DOCUMENTS

| | | | |
|---|---|---|---|
| CN | 102989047 | A | 3/2013 |
| CN | 103118581 | A | 5/2013 |
| CN | 204463124 | U | 7/2015 |
| CN | 105073158 | A | 11/2015 |
| CN | 106730091 | A | 5/2017 |
| EP | 00256640 | | 4/1987 |
| EP | 0368959 | B1 | 7/1992 |
| EP | 0742017 | A2 | 11/1996 |
| EP | 0790841 | B2 | 11/2000 |
| EP | 1108444 | A2 | 6/2001 |
| EP | 2682605 | A1 | 1/2014 |
| EP | 2857054 | A1 | 8/2019 |
| EP | 3558444 | A1 | 10/2019 |
| EP | 3281655 | A1 | 6/2020 |
| IN | 322019 | | 10/2017 |
| IN | 022019 | | 9/2018 |
| JP | S59177056 | | 2/1984 |
| JP | S61176358 | A | 8/1986 |
| JP | S63500639 | A | 3/1988 |
| JP | S645565 | A | 1/1989 |
| JP | H0451957 | U | 5/1992 |
| JP | H6023052 | A | 2/1994 |
| JP | H0889571 | A | 4/1996 |
| JP | H0923023 | A | 1/1997 |
| JP | H09239023 | A | 9/1997 |
| JP | H11235382 | A | 8/1999 |
| JP | 2001511400 | A | 8/2001 |
| JP | 2006223448 | A | 8/2006 |
| JP | 2007050277 | A | 3/2007 |
| JP | 2007529282 | A | 10/2007 |
| JP | 2008528173 | A | 7/2008 |
| JP | 2009136681 | A | 6/2009 |
| JP | 2009527343 | A | 7/2009 |
| JP | 2011510324 | A | 3/2011 |
| JP | 2012500385 | A | 1/2012 |
| JP | 2014174057 | A1 | 9/2014 |
| JP | 2016502911 | A | 2/2016 |
| WO | 9906082 | A1 | 2/1999 |
| WO | 2007140241 | A1 | 12/2007 |
| WO | 2012011975 | A1 | 1/2012 |
| WO | 2012155067 | A1 | 11/2012 |
| WO | 2015159915 | A1 | 10/2015 |
| WO | 2015173833 | A2 | 11/2015 |
| WO | 2015179824 | A1 | 11/2015 |
| WO | 2016198092 | A1 | 12/2016 |
| WO | 2018115530 | A1 | 6/2018 |
| WO | 2018142406 | A1 | 8/2018 |

OTHER PUBLICATIONS

European Patent Application No. 118747755.9, Extended European Search Report dated Apr. 12, 2021, 24 pages.

International Patent Application No. PCT/IB2021/060959, International Search Report and Written Opinion dated Dec. 28, 2021.

Japanese Patent Application No. JP2019540099, Office Action dated Jan. 4, 2022 - English Translation available.

Mexican Patent Application No. MX/a/2018/009298 Office Action dated May 27, 2022.

U.S. Appl. No. 16/074,230, Restriction Requirement dated Apr. 14, 2022.

IL office action and search report mailed Feb. 8, 2021 for application 278995.

International Preliminary Report on Patentability of Application No. PCT/IB2021/060959 mailed Jun. 8, 2023, 6 Pages.

Japanese Patent Application No. JP2021082323, Office Action dated Jul. 5, 2022—English Translation available.

Mexican Patent Application No. MX/a/2018/009298 Office Action dated Oct. 11, 2022.

Brazilian Search Report for Patent Application No. BR112018015694-9, mailed Feb. 1, 2017, 10 pages.

Extended Hearing Notice for Indian Patent Application No. 201947030569, mailed Mar. 4, 2024, 02 pages.

Final Office Action mailed Apr. 2, 2024 on for U.S. Appl. No. 16/074,230, filed Jul. 31, 2018, 06 pages.

Hearing Notice for Indian Patent Application No. 201817032293, mailed Jul. 28, 2023, 02 pages.

Hearing Notice for Indian Patent Application No. 201947030569, mailed Feb. 13, 2024, 02 pages.

(56) References Cited

OTHER PUBLICATIONS

Mexican Patent Application No. MX/a/2019/008791, Office Action dated Sep. 14, 2023.
Non-Final Office Action mailed on Sep. 13, 2023 on for U.S. Appl. No. 16/074,230, filed Jul. 31, 2018, 11 pages.
Office Action for Chinese Patent Application No. 201780020122.9, mailed Jun. 3, 2020, 19 pages.
Office Action for Chinese Patent Application No. 201780020122.9, mailed Mar. 3, 2021, 14 pages.
Office Action for Chinese Patent Application No. 201780020122.9, mailed Jan. 24, 2022, 10 pages.
Office Action for Chinese Patent Application No. 20188009152.4, mailed Jul. 6, 2022, 14 pages.
Office Action for Chinese Patent Application No. 20188009152.4, mailed Mar. 24, 2023, 18 pages.
Office Action for European Patent Application No. 17747112.5, mailed Jun. 1, 2023, 06 Pages.
Office Action for European Patent Application No. 17747112.5, mailed Apr. 4, 2024, 06 Pages.
Office Action for Indian Patent Application No. 201817032293, mailed May 13, 2021, 06 pages.
Office Action for Japanese Patent Application No. 2019540099, mailed Oct. 4, 2022, 12 pages.
Office Action for Japanese Patent Application No. 2023015281, mailed Nov. 29, 2023, 14 pages.
Office Action for Japanese Patent Application No. 2023067779, mailed Feb. 6, 2024, 09 pages.
U.S. Appl. No. 16/074,230 Final office action dated May 4, 2023.
U.S. Appl. No. 16/074,230 Non-Final office action dated Jun. 22, 2022.
"1st Japanese Office action dated Feb. 22, 2021 issued for JP2018-558506".
"1st Official Action mailed May 25, 2021 for U.S. Appl. No. 16/480,550".
1st Indian Office Action mailed May 13, 2021 regarding IN201817032293.
Chinese office action dated Mar. 3, 2021 for CN201780020122.9 (P10713-PCT-CN).
Communication mailed on Apr. 21, 2020 by EPO pursuant to Rules 70{2} and 70a{2} EPC to indicate maintenance of EP application 17747112.5 and to provide comments and/or amendments.
Extended ESR dated Apr. 12, 2021 & invitation dated Apr. 30, 2021 to file comments for EP application 18747755.
Extended European Search Report for Application No. 17747112.5 mailed Apr. 2, 2020, 10 pages.
International Preliminary Report on Patentability of Application No. PCT/IL2017/050117 mailed Aug. 16, 2018, 10 Pages.
International Preliminary Report on Patentability of Application No. PCT/IL2018/050117 mailed Aug. 15, 2019, 10 Pages.
International Search Report and Written Opinion for Application No. PCT/IL2017/050117, mailed May 18, 2017, 16 pages.
International Search Report and Written Opinion for Application No. PCT/IL2018/050117, mailed May 10, 2018, 15 pages.
International Search Report and Written Opinion from International Application No. PCT/IB2020/062117 mailed Apr. 4, 2021, 12 pages.
Israel Office Action and Search Report for Application No. IL278995, dated Feb. 8, 2021, 10 pages.
Mexican Patent Application No. MX/a/2019/008791, Office Action dated May 15, 2024.
Non-Final Office Action mailed Feb. 12, 2024 for U.S. Appl. No. 16/480,550, filed Feb. 1, 2018, 9 pages.
Notice of Allowance for U.S. Appl. No. 16/074,230, mailed Oct. 1, 2024, 08 pages.
Notice of Allowance for U.S. Appl. No. 16/480,550, mailed Sep. 29, 2024, 08 pages.
Office Action for Chinese Application No. 201780020122.9 dated Jun. 3, 2020.
Office Action for Indian Patent Application No. 201947030569, mailed Dec. 22, 2021, 07 pages.
U.S. Appl. No. 16/480,550 Non-Final office action dated Jul. 21, 2022.
U.S. Appl. No. 16/480,550, Final Office Action dated Apr. 25, 2023.
U.S. Appl. No. 16/480,550, Final office Action dated Mar. 24, 2022.

* cited by examiner

SMART PERITONEAL DIALYSIS DEVICE

RELATED APPLICATIONS

This is a Divisional Application of U.S. patent application Ser. No. 16/480,550 filed on Jul. 24, 2019, now pending, which claims the benefit of International Application No. PCT/IL2018/050117 filed on Feb. 1, 2018. The PCT/IL2018/050117 application claims the priority benefit of International Application No. PCT/IL2017/050117 filed on Feb. 1, 2017 and the U.S. Provisional Patent Application No. 62/488,944 filed 24 Apr. 2017. Additionally, the International Application No. PCT/IL2017/050117 filed on Feb. 1, 2017 claims the priority benefit of U.S. Provisional Patent Application No. 62/289,362 filed on Feb. 1, 2016.

The contents of the above-referenced applications are incorporated herein by reference in their entirety.

FIELD AND BACKGROUND OF THE INVENTION

The present invention, in some embodiments thereof, relates to a device for a dialysis treatment and, more particularly, but not exclusively, to a device for monitoring a peritoneal dialysis treatment.

Peritoneal Dialysis is a lifesaving procedure for removing waste and excess water from the blood. It is used primarily to sustain the health of patients who have experienced renal failure. While peritoneal dialysis may seem as a simple process, many of its effects on the body are not fully understood. This lack of knowledge translates to questions about whether the therapy patients receive is being delivered in an optimal fashion.

The peritoneal dialysis removes wastes and excess water from the blood inside the body using the peritoneum as a natural semipermeable membrane. Wastes and excess water move from the blood, across the peritoneal membrane, and into a special dialysis solution, called dialysate, in the abdominal cavity and more specifically the peritoneal cavity. The waste materials that are removed include uremic wastes, excess water, and excess minerals. Urea clearance has become the chief indicator of the adequacy of dialysis. Urea levels in spent dialysate present a good estimator of the performance of the dialysis session.

SUMMARY OF THE INVENTION

Some examples of some embodiments of the invention are listed below:

Example 1. A device for monitoring and/or modifying a peritoneal dialysis treatment, comprising:

- a memory which stores at least one treatment protocol;
- a control circuitry connected to said memory, wherein said control circuitry generates a report and/or modifies said treatment if an outcome of said treatment is not a desired outcome of said treatment protocol.

Example 2. The device of example 1, further comprising an interface, wherein said interface delivers an alert to a patient and/or a caregiver based on said report.

Example 3. The device of example 2, further comprising a tubing shaped and sized to allow flow of fluid into a catheter, and wherein said control circuitry modifies said treatment based on said flow of said fluid and/or based on said fluid content within said tubing.

Example 4. The device of example 3, comprising:

- a pump rotor in association with said tubing, wherein said pump rotor is configured to move said fluid, and wherein said control circuitry modifies said treatment by modifying the rotation of said pump rotor.

Example 5. The device of examples 3 and 4, comprising at least one testing path fluidically connected to said tubing, wherein said testing path is shaped and sized to allow at least partial fluid flow from said tubing to said testing path.

Example 6. The device of example 5, comprising at least one light sensor connected to said control circuitry for measuring the properties of light passing through fluid within said testing path.

Example 7. The device of example 5, comprising at least one color scale proximally to said testing path for visually analyzing the color of fluid within said testing path.

Example 8. The device of example 2, comprising at least one clinical sensor connected to said control circuitry for sensing at least one patient clinical parameter, and wherein said outcome of said treatment is a clinical outcome indicated by said patient clinical parameter.

Example 9. The device of example 8, wherein said patient clinical parameter is selected from a list consisting of heart rate, blood pressure, and/or body weight.

Example 10. The device of examples 8 or 9, wherein said control circuitry signals said interface to generate an alert to a patient and/or to a caregiver if said patient clinical parameter is not in a desired range of values.

Example 11. The device of any one of examples 8 to 10, further comprising a communication circuitry for transmitting an indication to a physician if said patient clinical parameter is not in a desired range of values.

Example 12. The device of any one of examples 8 to 11, wherein said memory stores values of said patient clinical parameter.

Example 13. The device of any one of examples 8 to 12, wherein said control circuitry modifies said treatment or modifies at least one treatment parameter or selects a different treatment protocol stored in said memory if said patient clinical parameter is not in a desired range of values.

Example 14. The device of example 13, wherein said at least one modified treatment parameter comprises dwelling time, treatment duration and/or composition of infused dialysate.

Example 15. The device of examples 8 to 14, wherein said control circuitry signals said interface to indicate which dialysate bag to select or which dialysate bag to provide to a user.

Example 16. The device of example 3, comprising at least one clinical sensor connected to said control circuitry for measuring a chemical composition of dialysate fluid within said tubing.

Example 17. The device of example 16, wherein said clinical sensor measures an ionic strength of said dialysate fluid and/or dextrose levels and/or urea levels and/or creatinine levels in said dialysate fluid.

Example 18. The device of any one of examples 16 or 17, wherein said control circuitry signals said interface to generate an alert indication if said chemical composition is not in a desired range of values.

Example 19. The device of any one of examples 16 to 18, further comprising a communication circuitry for transmitting an indication to a physician if said chemical composition is not in a desired range of values.

Example 20. The device of any one of examples 16 to 19, wherein said control circuitry modifies said treatment or modifies at least one treatment parameter or selects a different treatment protocol if said chemical composition is not in a desired range of values.

Example 21. The device of example 20, wherein said at least one modified parameter of said treatment comprises dwelling time, treatment duration and/or composition of infused dialysate.

Example 22. The device of example 1, further comprising at least one sensor for measuring biological properties and/or chemical properties and/or physical properties of a drained dialysate during a draining process; and wherein said control circuitry detects peritonitis based on said measured properties of said drained dialysate.

Example 23. The device of example 22, further comprising an interface for delivery of indications to a patient and/or a caregiver; wherein said control circuitry signals said interface to generate an alert indication if said peritonitis is detected.

Example 24. The device of example 23, further comprising a communication circuitry, wherein said communication circuitry transmits said alert indication to a physician.

Example 25. The device of any one of examples 22 to 24, wherein said control circuitry modifies at least one parameter of said treatment protocol or selects an alternative treatment protocol stored in said memory if said peritonitis is detected.

Example 26. The device of any one of examples 22 to 25, wherein said biological properties comprise white blood cells number in said drained dialysate.

Example 27. The device of any one of examples 22 to 26, wherein said physical properties comprise the turbidity level of said drained dialysate.

Example 28. The device of any one of examples 22 to 27 wherein said sensor is an optical sensor configured to measure the optical density of said drained dialysate in at least one wave length.

Example 29. A method for modifying a peritoneal dialysis treatment based on the content of a drained dialysate using a device, comprising:

measuring at least one parameter related to said content of said drained dialysate, by at least one sensor or a manual indicator of said device;

modifying said treatment based on said at least one parameter of said measuring.

Example 30. The method of example 29, comprising:

detecting peritonitis based on said at least one parameter of said measuring.

Example 31. The method of example 30, comprising:

treating said peritonitis based on said detecting.

Example 32. The method of example 31, wherein said treating comprises instructing a user of said device to add antibiotics to a dialysate bag.

Example 33. The method of example 32, wherein said treating comprises switching between a dialysate bag to an antibiotic-containing bag.

Example 34. The method of any one of examples 29 to 33, wherein said at least one parameter is an inflammation-related parameter.

Example 35. The method of example 34, wherein said inflammation-related parameter comprises a turbidity level of said drained dialysate.

Example 36. The method of example 34, wherein said inflammation-related parameter comprises the level of white blood cells and/or bacteria in said drained dialysate.

Example 37. The method of example 34, wherein said inflammation-related parameter comprises the level of pro-inflammatory cytokines in said drained dialysate.

Example 38. The method of anyone of examples 31 to 37, wherein said modifying comprises infusing an antibiotic solution into the peritoneal cavity.

Example 39. The method of example 30, wherein said modifying comprises terminating said treatment.

Example 40. The method of example 29, comprising:

determining the efficacy of a peritoneal dialysis treatment based on a value of said at least one parameter of said measuring.

Example 41. The method of example 40, wherein said at least one parameter comprises dextrose levels of said drained dialysate.

Example 42. The method of examples 40 or 41, wherein said at least one parameter comprises creatinine levels of said drained dialysate.

Example 43. The method of anyone of examples 40 to 42, wherein said at least one parameter comprises urea levels of said drained dialysate.

Example 44. The method of any one of examples 40 to 43, wherein said modifying comprises increasing the dwelling time of a dialysate within a peritoneal cavity if said efficacy is lower than a desired efficacy.

Example 45. The method of any one of examples 40 to 44, wherein said modifying comprises reducing the dwelling time of a dialysate within a peritoneal cavity if said efficacy is larger than a desired efficacy.

Example 46. The method of any one of examples 40 to 45, wherein said modifying comprises increasing the dextrose levels of infused dialysate.

Example 47. The method of any one of examples 40 to 46, comprising:

delivering and indication to a patient and/or to a caregiver if said efficacy is not a desired efficacy.

Example 48. The method of any one of examples 40 to 46, comprising:

transmitting an indication to a physician if said efficacy is not a desired efficacy.

Example 49. A method for modifying a peritoneal dialysis treatment protocol which has at least one parameter using a device, comprising:

measuring at least one outcome of said peritoneal dialysis treatment during said treatment by said device;

determining if said at least one outcome is a desired outcome;

modifying said at least one treatment parameter by said device if said outcome is not a desired outcome according to said determining.

Example 50. The method of example 49, wherein said at least one outcome comprises a clinical outcome.

Example 51. The method of example 50, wherein said at least one clinical outcome comprises the volume of a drained dialysate, and wherein said modifying comprises modifying dwelling time of dialysate and/or the content of said dialysate based on said volume of drained dialysate.

Example 52. The method of example 50, wherein said at least one clinical outcome comprises the chemical and/or the biological content of a drained dialysate, and wherein said modifying comprises modifying dwelling time of dialysate and/or the content of said dialysate based on said content of said drained dialysate.

Example 53. The method of example 50, wherein said at least one clinical outcome comprises an ionic strength of a drained dialysate, and wherein said modifying comprises modifying dwelling time of dialysate and/or the dextrose levels of said dialysate based on said ionic strength of said drained dialysate.

Example 54. The method of any one of examples 49 to 53, comprising:

receiving input related to a user of said device, wherein said input comprises clinical input of said user and/or input related to activation of said device by said user.

Example 55. The method of example 54, wherein said input comprising input regarding activation of said device by said user.

Example 56. The method of example 55, wherein said determining comprises determining if said activation of said device based on said input is according to a determined treatment protocol.

Example 57. The method of example 56, comprising generating a treatment compliance report based on said determining.

Example 58. The method of example 57, comprising transmitting said treatment compliance report to a physician or an expert.

Example 59. The method of any one of examples 56 to 58, comprising:

alerting said user if said activation of said device is not according to said determined treatment protocol.

Example 60. A detachable unit of a peritoneal dialysis device, comprising:

a detachable housing;

a tubing with two openings shaped and sized to be partly associated with a pump rotor within said housing;

at least two connectors, wherein each of said two connectors is connected to said tubing at one of said two openings, and wherein said two connectors are fixed in the same side of said housing.

Example 61. The unit of example 60, wherein at least one of said two connectors is a disinfecting connector, and wherein said tubing comprises disinfecting fluid proximally to said disinfecting connector.

Example 62. The unit of example 61, wherein said disinfecting connector comprises at least one foil shaped and sized to be teared by an external connector.

Example 63. The unit of any one of examples 60 to 62, comprising at least two flow regulators surrounding said tubing near said connectors, wherein said flow regulators are shaped and sized to allow fluid flow between said tubing and said connector.

Following are some additional examples of some embodiments of the invention:

Example 1. A device for monitoring and/or modifying a peritoneal dialysis treatment, comprising:

a memory which stores at least one treatment protocol;

a control circuitry connected to said memory, wherein said control circuitry generates a report and/or modifies said treatment if an outcome of said treatment is not a desired outcome of said treatment protocol.

Example 2. The device of example 1, further comprising an interface, wherein said interface delivers an alert to a patient and/or a caregiver based on said report.

Example 3. The device of example 2, further comprising a tubing shaped and sized to allow flow of fluid into a catheter, and wherein said control circuitry modifies said treatment based on said flow of said fluid and/or based on said fluid content within said tubing.

Example 4. The device of example 3, comprising:

a pump rotor in association with said tubing, wherein said pump rotor is configured to move said fluid, and wherein said control circuitry modifies said treatment by modifying the rotation of said pump rotor.

Example 5. The device of any one of examples 3 and 4, comprising at least one testing path fluidically connected to said tubing, wherein said testing path is shaped and sized to allow at least partial fluid flow from said tubing to said testing path.

Example 6. The device of any one of examples 3 to 5, comprising at least one light sensor connected to said control circuitry for measuring the properties of light passing through fluid within said tubing.

Example 7. The device of example 5, comprising at least one color scale proximally to said testing path for visually analyzing the color of fluid within said testing path, wherein said color scale comprises color or indications thereof of dialysate colors.

Example 8. The device of example 2, comprising at least one clinical sensor connected to said control circuitry for sensing at least one patient clinical parameter, and wherein said outcome of said treatment is a clinical outcome indicated by said patient clinical parameter.

Example 9. The device of example 8, wherein said patient clinical parameter is selected from a list consisting of heart rate, blood pressure, and/or body weight.

Example 10. The device of any one of examples 8 or 9, wherein said control circuitry signals said interface to generate an alert to a patient and/or to a caregiver if said patient clinical parameter is not in a desired range of values.

Example 11. The device of any one of examples 8 to 10, further comprising a communication circuitry for transmitting an indication to a physician if said patient clinical parameter is not in a desired range of values.

Example 12. The device of any one of examples 8 to 11, wherein said memory stores values of said patient clinical parameter.

Example 13. The device of any one of examples 8 to 12, wherein said control circuitry modifies said treatment or modifies at least one treatment parameter or selects a different treatment protocol stored in said memory if said patient clinical parameter is not in a desired range of values, wherein said at least one modified treatment parameter comprises dwelling time, treatment duration and/or composition of infused dialysate.

Example 14. The device of example 3, comprising at least one clinical sensor connected to said control circuitry for measuring a chemical composition of dialysate fluid within said tubing.

Example 15. The device of example 14, wherein said clinical sensor measures an ionic strength of said dialysate fluid and/or dextrose levels and/or urea levels and/or creatinine levels in said dialysate fluid.

Example 16. The device of any one of examples 14 or 15, wherein said control circuitry signals said interface to generate an alert indication if said chemical composition is not in a desired range of values.

Example 17. The device of any one of examples 14 to 16, wherein said control circuitry modifies said treatment or modifies at least one treatment parameter or selects a different treatment protocol if said chemical composition is not in a desired range of values, wherein said at least one modified parameter of said treatment comprises dwelling time, treatment duration and/or composition of infused dialysate.

Example 18. The device of example 1, further comprising at least one sensor for measuring biological properties and/or chemical properties and/or physical properties of a drained dialysate during a draining process; and wherein said control circuitry detects peritonitis based on said measured properties of said drained dialysate.

Example 19. The device of example 18, further comprising an interface for delivery of indications to a patient and/or a caregiver; wherein said control circuitry signals said interface to generate an alert indication if said peritonitis is detected.

Example 20. The device of example 19, further comprising a communication circuitry, wherein said communication circuitry transmits said alert indication to a physician.

Example 21. The device of any one of examples 18 to 20, wherein said control circuitry modifies at least one parameter of said treatment protocol or selects an alternative treatment protocol stored in said memory if said peritonitis is detected.

Example 22. The device of any one of examples 18 to 21, wherein said physical properties comprise the turbidity level of said drained dialysate.

Example 23. The device of any one of examples 18 to 22 wherein said at least one sensor is an optical sensor configured to measure at least one optical parameter of said drained dialysate in one or more wavelengths.

Example 24. The device of example 23, wherein said at least one sensor is configured to measure absorption and/or scattering of light passing through said drained dialysate in one or more wavelengths in a range of 500-650 nm and/or in a range of 150-350 nm.

Example 25. The device of example 18, wherein said at least one sensor comprises a first sensor configured to measure absorption and/or scattering of light passing through said drained dialysate in one or more wavelengths is a wavelength range of 500-650 nm and a second sensor configured to measure absorption and/or scattering of light passing through said drained dialysate in one or more wavelengths in a wavelength range of 150-350 nm.

Example 26. The device of example 18, wherein said at least one sensor comprises a first sensor configured to measure absorption and/or scattering of light passing through said drained dialysate in a wavelength range of 500-650 nm and a second sensor configured to measure absorption and/or scattering of light passing through said drained dialysate in visible light wavelengths.

Example 27. The device of any one of examples 24 to 26, wherein said control circuitry detects peritonitis based on said light absorption and/or scattering measurements.

Example 28. The device of any one of the previous examples, comprising a battery electrically connected to said control circuitry.

Example 29. A peritoneal dialysis system, comprising:

a durable unit comprising:

an electric motor;

a battery electrically connected to said electric motor and configured to provide electric power to said electric motor;

a detachable unit configured to be attached to said durable unit, comprising:

a rotor connectable to said motor;

a tubing at least partly in contact with said rotor;

wherein said system weight is below 4000 gr.

Example 30. The system of example 29, wherein said system does not comprise a dialysate heater.

Example 31. A method for detecting a physiological condition in a drained dialysate, comprising:

measuring at least one parameter related to said content of said drained dialysate, by at least one sensor or a manual indicator of a peritoneal dialysis device;

detecting a physiological condition based on said at least one parameter.

Example 32. The method of example 31, wherein said physiological condition comprises peritonitis, pre-peritonitis or post peritonitis.

Example 33. The method of example 31, comprising:

indicating a treatment for said physiological condition based on said detecting.

Example 34. The method of example 33, wherein said indicating comprises indicating a user of said device to add antibiotics to a dialysate bag.

Example 35. The method of any one of examples 33 or 34, wherein said indicating comprises indicating to switch between a dialysate bag to an antibiotic-containing bag.

Example 36. The method of any one of examples 32 to 35, wherein said at least one parameter is an inflammation-related parameter, and wherein said physiological condition comprises inflammation.

Example 37. The method of example 36, wherein said inflammation-related parameter comprises a turbidity level of said drained dialysate.

Example 38. The method of example 36, wherein said inflammation-related parameter comprises the level of white blood cells and/or bacteria in said drained dialysate.

Example 39. The method of anyone of examples 32 to 38, wherein said indicating comprises indicating to infuse an antibiotic solution into the peritoneal cavity.

Example 40. The method of any one of examples 31 to 39, comprising:

determining the efficacy of a peritoneal dialysis treatment based on a value of said at least one parameter of said measuring.

Example 41. The method of example 40, wherein said at least one parameter comprises dextrose levels of said drained dialysate.

Example 42. The method of any one of examples 40 or 41, wherein said at least one parameter comprises creatinine levels of said drained dialysate.

Example 43. The method of anyone of examples 40 to 42, wherein said at least one parameter comprises urea levels of said drained dialysate.

Example 44. The method of any one of examples 40 to 43, wherein said indicating comprises indicating to increase the dwelling time of a dialysate within a peritoneal cavity if said efficacy is lower than a desired efficacy.

Example 45. The method of any one of examples 40 to 44, wherein said indicating comprises indicating a patient and/or to a caregiver if said efficacy is not a desired efficacy or if peritonitis is detected.

Example 46. The method of any one of examples 40 to 45, comprising:

transmitting an indication to a physician if said efficacy is not a desired efficacy or if peritonitis is detected.

Example 47. A detachable unit of a peritoneal dialysis device, comprising:

a detachable housing encasing said detachable unit;

a tubing with two openings shaped and sized to be partly associated with a pump rotor within said housing;

at least two connectors, wherein each of said two connectors is connected to said tubing at one of said two openings, and wherein said two connectors are fixed in the same side of said housing.

Example 48. The unit of example 47, wherein at least one of said two connectors is a disinfecting connector, and wherein said tubing comprises disinfecting fluid proximally to said disinfecting connector.

Example 49. The unit of example 48, wherein said disinfecting connector comprises at least one foil shaped and sized to be teared by an external connector.

Example 50. The unit of any one of examples 47 to 49, comprising at least two flow regulators surrounding said tubing near said connectors, wherein said flow regulators are shaped and sized to allow fluid flow between said tubing and said connector.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof.

Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as monitoring a peritoneal dialysis treatment, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

and

Figure 1:
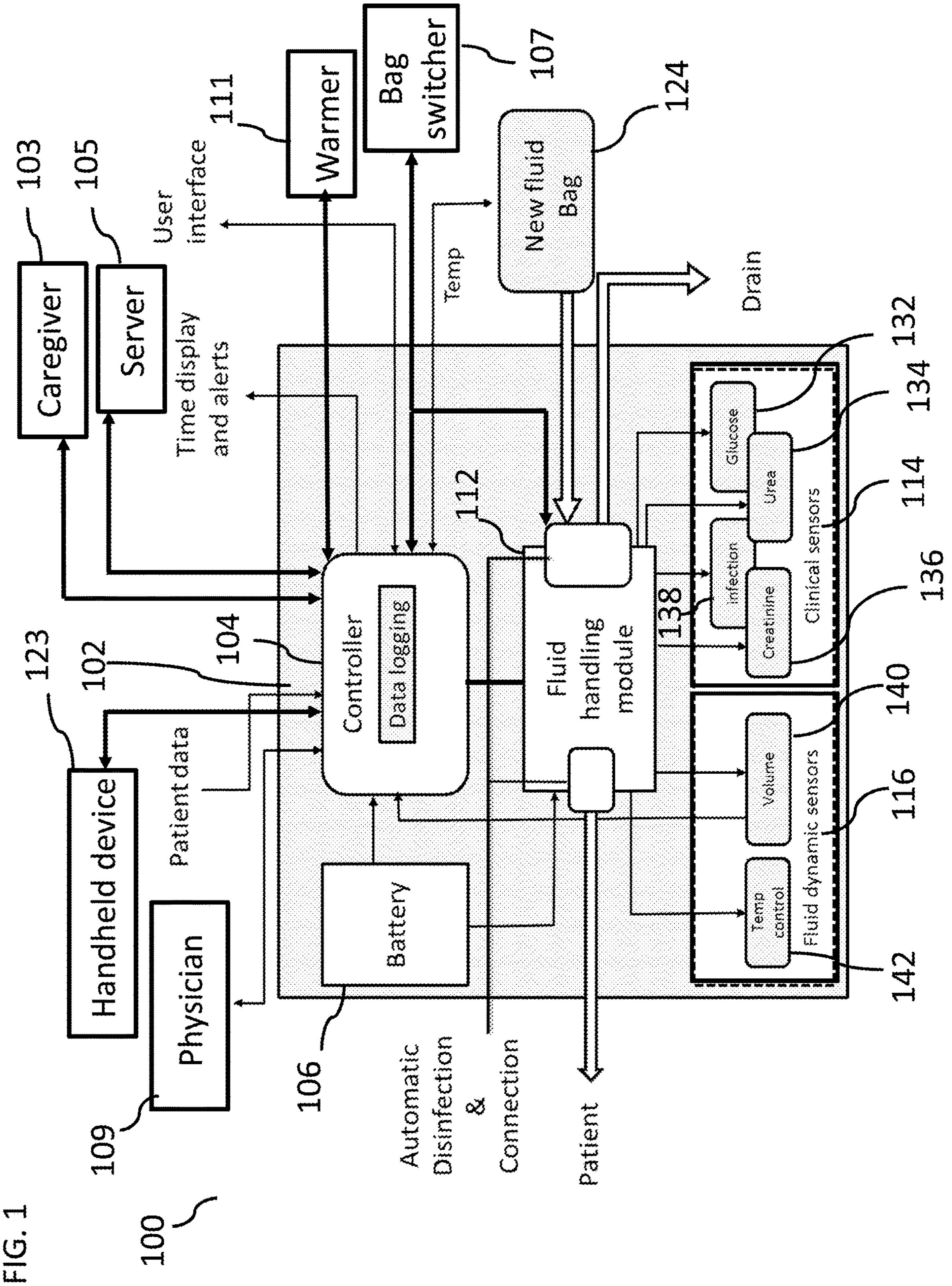
FIG. 1 is a block diagram of a system for monitoring and adjusting a dialysis treatment, according to some embodiments of the invention.

FIGS. 14A-14D are schematic illustrations of a peritoneal dialysis system with a detachable portable peritoneal dialysis device and a peritoneal dialysis cycler base, according to some embodiments of the invention.

DESCRIPTION OF SPECIFIC EMBODIMENTS OF THE INVENTION

The present invention, in some embodiments thereof, relates to a device for monitoring a treatment and, more particularly, but not exclusively, to a device for monitoring a peritoneal dialysis treatment.

A broad aspect of some embodiments relates to trading off various parameters of a peritoneal dialysis treatment based on at least one effect of the treatment. Optionally the treatment parameters modifications are applied by a peritoneal dialysis device. In some embodiments, the tradeoffs comprise modifying the duration of an infusion process and/or duration of a draining process and/or the dwelling time of a dialysate within the peritoneal cavity. In some embodiments, the tradeoffs comprise modifying the composition of the infused dialysate and/or selecting a different protocol plan, for example to treat peritonitis. In some embodiments, the tradeoffs comprise modifying at least one parameter of a treatment protocol following an undesired treatment efficacy. In some embodiments, the treatment is postponed or proponed. In some embodiments, the amount of dialysate per day is modified. In some embodiments, treatment schedule and/or or treatment type are modified.

An aspect of some embodiments relates to modifying a peritoneal dialysis treatment during a treatment session. In some embodiments, the treatment is modified automatically based on feedback or input from a user during the treatment session. In some embodiments, the input comprises changes in the treatment duration and/or treatment initiation timing. Alternatively or additionally, the treatment is modified based on measurements performed during the treatment session. In some embodiments, the treatment is modified based on measurements performed between treatment sessions, for example clinical measurements of the patient.

According to some exemplary embodiments, the treatment is modified if the treatment is not safe. In some embodiments, the treatment is modified if at least one parameter value results in an unsafe treatment. In some embodiments, the treatment is modified or is delayed when the content of the dialysate bag and/or the identification of the dialysate bag and/or the expiry date of the dialysate bag is not valid. Alternatively or additionally, the treatment is modified based on information received prior to the treatment session, for example regarding the validity of the dialysate bag content.

In some embodiments, the treatment is modified based on measurements of parameters indicating an inflammation, for example body temperature measurements and/or turbidity level of the drained dialysate. In some embodiments, parameters indicating an inflammation comprise the level of white blood cells (WBC) in the drained dialysate. In some embodiments, a white blood cells count higher than a determined level indicate an inflammation, for example a white blood cells count higher than 40 WBC\ml, for example 50, 55, 60, 65 WBC\ml or any intermediate or larger value. In some embodiments, the WBC count is relative to a base line or a reference count, for example prior to treatment. Alternatively, the WBC count is compared to known clinical standards, for example to detect clinical variations. or to a In some embodiments, the treatment is modified based on measurements that provide an indication regarding the general clinical condition of the patient, for example heart pulse, blood pressure, and/or body temperature and/or body weight or change in body weight. In some embodiments, the treatment is modified based on measurements that provide an indication regarding the treatment efficacy, for example dextrose levels, creatinine levels, urea levels, potassium levels, phosphorous levels or any chemical, mineral or biological substance in the drained dialysate. In some embodiments, the amount of fluid in the drained dialysate is also an indicator for the efficacy of the treatment. In some embodiments, following intake of food, the expected drained dialysate is calculated, and optionally the treatment efficacy is determined based on the relation between the actual volume and the expected volume of the drained dialysate.

In some embodiments, the measurements are relative to a baseline or a reference measurements. In some embodiments, the measured values are compared to known standards, for example to determine clinical variations. In some embodiments, the dextrose levels, creatinine levels, urea levels, potassium levels, phosphorous levels or any chemical, mineral or biological substance in the drained dialysate are related to a specific dwelling time of the dialysate inside the peritoneal cavity. In some embodiments, a memory of the device contains ranges of values for the measured chemical and/or biological parameters in specific dwelling times.

An aspect of some embodiments relates to compensating for variations in a planned peritoneal dialysis treatment during the treatment. In some embodiments, a peritoneal dialysis device alters a peritoneal dialysis treatment protocol following treatment modifications introduced by a patient and/or a caregiver or by the computer itself, for example when a dialysate bag is not a valid bag. In some embodiments, the treatment is modified by the device when for example, a treatment session is terminated prematurely, or when a catheter disconnection or is disconnected prematurely or any action that does not match a predetermined treatment protocol. Alternatively or additionally, the peritoneal dialysis treatment device alters a peritoneal dialysis treatment protocol following measurements of at least one clinical parameter.

An aspect of some embodiments relates to monitoring a peritoneal dialysis treatment during the treatment. In some embodiments, the device delivers indications and/or alerts to a patient based on the treatment monitoring. In some embodiments, a peritoneal dialysis device monitors different steps of the treatment, for example generation and/or disinfection of a fluid path to a patient catheter, pumping in and/or draining of dialysate. In some embodiments, the device measures clinical parameters of the patient, for example pulse, blood pressure and/or body temperature. In some embodiments, the device determines whether an actual treatment follows a pre-determined treatment plan.

An aspect of some embodiments relates to peritonitis detection and/or treatment and/or monitoring peritonitis progression. In some embodiments, peritonitis is detected and/or treated during a peritoneal dialysis treatment session. In some embodiments, peritonitis is detected by analyzing the drained dialysate during a treatment session. Optionally, the content of the drained dialysate is continuously analyzed during the treatment session. Alternatively, the content of the drained dialysate is analyzed at least twice during a draining procedure of the dialysis treatment. In some embodiments, the level of white blood cells and/or pro-inflammatory cytokines and/or live or dead bacteria level and/or fungi within the drained dialysate is measured, for example to allow detection of peritonitis. In some embodiments, following peritonitis detection the patients receives instructions to inject antibiotics into a fresh dialysate bag for a specific number of exchange cycles.

In some embodiments, peritonitis is detected based on clinical parameters measurements of the patient. In some embodiments, the clinical parameters are measured during the treatment session. Optionally, peritonitis is detected based on a combination of the clinical parameters measurements and the analysis of the drained dialysate content. In some embodiments, if peritonitis is detected based on the measured clinical parameters and/or the analysis of the drained dialysate then an indication is provided. In some embodiments, the indication is delivered to the patient and/or to a physician and/or to a caregiver.

In some embodiments, the measured values of the clinical parameters and/or the analysis results of the drained dialysate are delivered to a decision maker, for example a physician or a device or a remote computer for peritonitis detection. In some embodiments, the measured values of the clinical parameters and/or the analysis results of the drained dialysate are delivered to a decision maker for monitoring the progression of peritonitis.

In some embodiments, peritonitis or a peritonitis indication is determined based on a turbidity level or a change in turbidity of the drained dialysate. In some embodiments, the turbidity level of the drained dialysate is an indicator to the inflammation level. In some embodiments, the turbidity level of the drained dialysate is an indicator to the level of bacteria and/or fungi within the peritoneal space. In some embodiments, if the measured turbidity level exceeds a desired turbidity threshold then an indication is provided to the patient and/or to a physician and/or to a caregiver.

In some embodiments, if peritonitis is detected then the peritoneal dialysis treatment is terminated or modified. In some embodiments, is peritonitis is detected, a peritonitis treatment plan is suggested. In some embodiments, a peritonitis treatment plan comprises at least one wash of the peritoneal cavity with an antibiotic or an anti-inflammatory solution. Alternatively or additionally, a peritonitis treatment plan comprises infusion of dialysate solutions that include antibiotics and/or anti-inflammatory agents.

According to some embodiments, to reduce the risk of peritonitis, the peritoneal dialysis device connects and disinfects a flow path in and/or from the patient's catheter. In some embodiments, to detect, optionally early detect peritonitis the device measures detects particles in the drained dialysate solution. In some embodiments, a source of light, for example white or monochromatic is placed near the fluid flow path, where the drained dialysate flows. Optionally, a sensor, for example an optical sensor measures one or more optical parameters, for example light absorption, light scattering of light travelling through the drained dialysate in one or more wavelengths. Optionally, the optical sensor measures the reduction in light intensity while the light travels through the drained dialysate. In some embodiments, the device measures the absorption and/or scattering of light traveling through the drained dialysate. In some embodiments, a spectrophotometer of the device identifies the presence of particles in the drained dialysate.

According to some embodiments, peritonitis is detected by measuring in a diverted portion some of the drained dialysate. In some embodiments, the drained dialysate is diverted to a testing path, for example a testing tube. In some embodiments, in the testing tube the drained dialysate reacts with reagents stored in the device, for example to create a chemical reaction that will generate a human detectable indication for the presence of bacteria or WBC or particles in the drain dialysate. In some embodiments, the human detectable indication is a color indication that optionally is detected by measuring the absorbance in a specific wavelength or in a range of wave lengths. In some embodiments, the change in color is detected by a colorimeter of the device. Optionally, the tube is removable or is part of a detachable unit of a PPDD device, also termed herein as a disposable unit. In some embodiments, the tube comprises a testing paper or a reagent. In some embodiments, the peritoneal dialysis device comprises a mechanism that prevents for example, backflow if the testing tube is reused.

An aspect of some embodiments relates to optimizing a peritoneal dialysis treatment during the treatment. In some embodiments, the treatment is optimized during the treatment based on an analysis of the drained dialysate. In some embodiments, the drained dialysate is an indicator to the functionality level of the peritoneum membrane. In some embodiments, if the functionality of the peritoneum membrane is below a desired threshold, then at least one parameter of the dialysis treatment and/or the content of the dialysate solution is modified.

In some embodiments, the levels of chemicals and/or biological compounds within the drained dialysate, for example dextrose, creatinine and/or urea are measured. In some embodiments, the dextrose levels within the drained dialysate are compared to the dextrose levels in the fresh dialysate. In some embodiments, if the functionality level of the peritoneal membrane is lower than a threshold level, then the dwell time of the dialysate within the peritoneal cavity is increases. In some embodiments, if the functionality level of the peritoneal membrane is higher than the threshold level, then the dwell time is reduced.

In some embodiments, the levels of dextrose in the drained dialysate are an indicator to the deterioration level of the peritoneal membrane. In some embodiments, high levels of dextrose in the drained dialysate indicate that the peritoneal membrane undergoes apoptosis or sclerosis. In some embodiments, the peritoneal membrane is deteriorated due to collagen blockade, which is optionally driven by an infection and/or an inflammation process of the membrane.

According to some embodiments, the levels of creatinine in the drained dialysate are measured. In some embodiments, the creatinine levels provide an indication regarding the efficacy of the peritoneal dialysis treatment. In some embodiments, lower creatinine levels, for example creatinine levels in a range of 0-7 mg/dcl indicate that the treatment has a low efficacy.

In some embodiments, the creatinine levels are measured by diverting the flow of the drained dialysate to a specific area in the device, outside the drained dialysate flow path. In some embodiments, in this area the drained dialysate fluid reacts with at least one reagent stored in the device. In some embodiments, the reaction produces a color, the intensity of produced colored is proportional to the amount of creatinine in the drained dialysate. In some embodiments, a source of light, white or monochromatic and at least one light sensor arrangement of the device, are positioned near the drained dialysate flow path. In some embodiments, the light sensor senses the intensity of light travelling from the light source and through the drained dialysate. In some embodiments, the device measures the loss in the light intensity.

In some embodiments, measuring a color reaction indicates the amount of creatinine removed during the last dialysis session. For example: Jaffe reaction, a calorimetric procedure in which creatinine forms a yellow orange complex in alkaline solution with picric acid. This colored complex is determined photometrically. In some embodiments, the intensity of the produced color is directly proportional to the amount of creatinine in the sample. Alternatively an enzyme stored in the device generates a colorimetric reaction that is an indicator to the creatinine levels.

According to some embodiments, the levels of urea in the drained dialysate are measured. In some embodiments, the urea levels provide an indication regarding the efficacy of the peritoneal dialysis treatment. In some embodiments, lower urea levels, for example urea levels in a range of 0-15 mg/dcl indicate that the treatment has a low efficacy.

In some embodiments, the urea levels are measured by diverting the flow of the drained dialysate to a specific area in the device, outside the drained dialysate flow path. In some embodiments, in this area the drained dialysate fluid reacts with at least one reagent stored in the device. In some embodiments, the reaction produces a color, the intensity of produced colored is proportional to the amount of creatinine in the drained dialysate.

In some embodiments, the diacetyl monoxime colorimetric method and Berthelot reaction are used to measure the urea levels. In some embodiments, in this method, the urea is converted to ammonia by an enzyme called urease. The ammonia produced is combined with 2-oxoglutarate and NADH in the presence of glutamate dehydrogenase (GDH), which yields L-Glutamate and NAD. The decrease in NADH absorbance is proportional to the urea concentration.

According to some embodiments, the levels of dextrose in the drained dialysate are measured. In some embodiments, the dextrose levels provide an indication regarding the efficacy of the peritoneal dialysis treatment. In some embodiments, high dextrose levels, for example dextrose levels above 30% of the original concentration in the "fresh" dialysate solution indicate that the treatment has a low efficacy.

In some embodiments, the dextrose levels are measured by diverting the flow of the drained dialysate to a specific area in the device, outside the drained dialysate flow path. In some embodiments, in this area the drained dialysate fluid reacts with at least one reagent stored in the device. In some embodiments, the reaction produces a color, the intensity of produced colored is proportional to the amount of dextrose in the drained dialysate.

In some embodiments, a source of light, white or monochromatic and at least one light sensor arrangement of the device, are positioned near the drained dialysate flow path. In some embodiments, the light sensor senses the intensity of light travelling from the light source and through the drained dialysate. In some embodiments, the device measures the loss in the light intensity. In some embodiments, measuring a color reaction indicates the amount of dextrose in the drained dialysate. In some embodiments, the levels of dextrose in the drained dialysate are compared to the dextrose levels in the fresh dialysate, for example to determine the treatment efficacy and/or the absorption of dextrose by the peritoneal membrane.

An aspect of some embodiments relates to automatically determining a patient compliance with a peritoneal dialysis treatment. In some embodiments, the patient is treated at home. In some embodiments, the patient compliance with the treatment is measured during a treatment session. In some embodiments, a compliance report is generated following each treatment session, and optionally stored in a memory. In some embodiments, a compliance indication is delivered to the patient upon request or in specific time periods. In some embodiments, a compliance indication is delivered to a physician or a caregiver. Optionally, the compliance report is transmitted to a remote computer of a physician.

According to some embodiments, a peritoneal dialysis device increases the compliance of the patient with the treatment by providing exchange reminders, reducing patient errors, automatically disinfects a flow path in and out from a patient catheter. In some embodiments, the exchange reminders include reminders regarding an infusion process and/or a draining process. In some embodiments, the exchange treatments are performed in a pre-determined time during the day. In some embodiments, the reminders are provided by a timer of the device. In some embodiments, a predefined exchange schedule is entered to the device, for example by the medical staff, or the patient. In some embodiments, based on this schedule the device alerts the patient on a scheduled exchange, and/or on delayed exchanges (as predefined) and/or on missed exchanges. In some embodiments, the device alerts medical staff by communication regarding delayed and/or missed exchanges. Optionally, the alerts delivered to the medical staff include patient identity as well as missed exchange information. (e.g.) John Smith, ID, date, no. exchange of the day—delayed & time. Optionally, additional information is displayed upon request from the medical staff or other requirements. In some embodiments, if an exchange cycle is missed, an alternative treatment plan is selected or at least one treatment parameter is modified, for example to compensate for the incompliance.

According to some embodiments, a peritoneal dialysis device increases the compliance and safety of the patient with the treatment by reducing patient errors. In some embodiments, the device guides the patient through the correct procedure. In some embodiments, the patient interacts with the device, for example to confirm step by step process adherence. In some embodiments, the device activates an automatic cycle control. In some embodiments, the device activates a treatment protocol that includes for example, the type of dialysate solution the patient is instructed to use. In some embodiments, if a different type of solution is used for example, a solution with wrong dextrose levels, the device delivers an alert and/or terminates the process or prevents the initiation of the process. In some embodiments, the dextrose levels are measured by using a spectrophotometer or by using reagents stored in the device that interact with the solution and change the light absorption in at least one wavelength or by reading a label, for example a barcode on the bag.

According to some embodiments, the peritoneal dialysis device automatically connects and disinfects a flow path. Additionally, the device use a controller and a pump to automatically perform draining, flushing and dialysate filling processes. In some embodiments, the device monitors the progress of the exchange process. In some embodiments, a predetermined exchange volume is entered to the device memory by the medical staff. In some embodiments, the device based on a measured flow rate calculates the volume of the drained dialysate and/or the volume of the infused dialysate and/or the remaining time for completion of the process. In some embodiments, the device delivers an indication to the patient or to a caregiver regarding the expected time to complete the process and/or volume and optionally displays a status, for example percentage of completed process and/or remaining time.

According to some embodiments, the device measures the dialysate flow using sensors positioned outside of the flow path, for example using the ultrasonic transit time principle. In some embodiments, the principle is that an ultrasonic pulse travelling in the flow direction of a fluid is accelerated, whereas an ultrasonic pulse moving in the opposite direction to the flow direction decelerated. In some embodiments, at last 4 piezo elements are arranged in an x-pattern near the flow path. In some embodiments, at least one transmitter sends pulsating ultrasonic waves through the dialysate fluid, flowing through the dialysate flow path in a predefined frequency from one side to another. In some embodiments, the difference in transit time is proportional to the average fluid velocity. In some embodiments, using this technique a sensor accuracy of +/−2% or higher, for example +/−1% is achieved. Alternatively, the fluid flow is measured by counting the revolutions of the pump during fluid infusion, and optionally subtracting air bubbles volume.

According to some exemplary embodiments, the device measures the temperature of the infused dialysate solution before the solution is infused into the patient's catheter. In some embodiments, if the measured temperature is not in a desired range of temperatures, for example 37+/−2° C. then an indication is delivered and/or the treatment is terminated. In some embodiments, the temperature sensor is positioned outside of the fluid flow path, for example by an IR sensor. Alternatively, the sensor is in contact with an external wall of the fluid flow path tubing. In some embodiments, the device communicates with a heating apparatus and/or with external temperature sensors, for example to allow a close loop control of the dialysate solution temperature.

According to some embodiments, the device comprises a scale for measuring the drained dialysate quantity. In some embodiments, the device comprises a tilting mechanism, for example to allow release of air bubbles from the fluid flow path. In some embodiments, the device comprises a heat preserving container, for example to preserve the heat of the dialysate bags when travelling.

An aspect of some embodiments relates to automatically switching between different fluids. In some embodiments, different fluid bags are connected through a fluid switching device to the patient catheter. In some embodiments, the fluid switching device switches between different fluid bags without the need to connect or disconnect the bags from the patient catheter. In some embodiments, the fluid switching device switches between different fluids according to a treatment plan, or following a modification of an existing treatment plan. In some embodiments, the peritoneal dialysis device activates at least one fluid bag for example, for later use.

In some embodiments, when detecting peritonitis, the dialysate fluid is switched with an antibiotic or an anti-inflammatory solution. Alternatively, the dialysate bag is switched with a dialysate bag that contains dialysate and an antibiotic solution. In some embodiments, the fluid switching device switched between dialysate fluids with varying dextrose concentration following an analysis of the peritoneal membrane functionality. In some embodiments, the fluid switching device switched between a dialysate fluid and a drained dialysate storage bag during a treatment session. In some embodiments, when peritonitis is detected, and optionally dialysate bags are switched at least one protocol parameter is modified based on the disease state and the applied treatment. In some embodiments, the modified protocol parameter comprises duration of treatment or infusion duration and/or number of exchanges per day.

An aspect of some embodiments relates to a detachable unit, also termed herein in some embodiments as a disposable unit, of a peritoneal dialysis device or system with at least two connectors at the same side. In some embodiments, the at least two connectors comprise a catheter connector and a dialysate bag connector. Optionally, the dialysate bag connector is a Y-connector. In some embodiments, the two connectors are disinfecting connectors, having a disinfecting fluid near each of the connectors. In some embodiments, each of the connectors comprise a foil, that is shaped and size to allow penetration of an external connector and/or release of the disinfecting fluid. In some embodiments, each of the connectors comprise a flow regulator, for example a removable clip to control the flow between the disinfecting connector and the external connector.

Possible advantages of using a device for monitoring and/or modifying a peritoneal dialysis treatment include, early detection of peritonitis, better compliance and educated flexibility, monitoring fluid extraction in relation to fluid intake into peritoneal cavity and expected additional fluid based on dietary information. Additional advantages include, optimizing treatment based on actual measurement (in line), optionally based on urea, creatinine and dextrose levels in drained solution, and preserving (increasing) peritoneal membrane functionality for longer period of time. The device allows to detect and optionally treat process that lower the efficacy of the treatment, for example by early detection of peritonitis inflammation and/or early detection of peritoneal membrane dysfunctionality.

As described above, a possible advantage of the device is that it allows to early detect and optionally treat peritonitis. The goals of treatment of peritonitis include rapid resolution of inflammation by eradication of causative organism and preservation of peritoneal membrane function. Early detection and rapid resolution is important as it had been demonstrated that a single, isolated episode of peritonitis had no significant effect on longitudinal peritoneal function, whereas recurrences or clusters of infection caused increases in dialysate/plasma ratio of creatinine and reductions in ultrafiltration, the significance of which increased with the number of episodes. Further it was demonstrated that solute transfer increases and ultrafiltration declines with time on PD. This process is exacerbated and accelerated by peritonitis, and appears to be proportional to the degree of associated inflammation and number of infections in close proximity.

Catheter survival Severe and prolonged PD peritonitis can lead to peritoneal membrane failure and is the most common cause of technique failure (move to HD) in PD. Using the peritoneal dialysis device discussed herein, peritonitis due to PD is not treated empirically while waiting for the results of dialysate culture, but can be detected and optionally treated during the treatment. Antibiotics are preferentially delivered via the peritoneal route to ensure maximal concentrations are delivered at the site of infection. It must be borne in mind however, that drugs administered intraperitoneally can be absorbed into the systemic circulation.

As described above, a possible advantage of the device is that in increases the treatment efficiency (efficacy). Treatment efficiency is related to the (1) wellbeing of the patient—among other indications, vital signs; pulse, BP and weight (2) waste extracted from the blood—urea, creatinine (3) access water removal from the blood.

According to some embodiments, a patient is connected to the dialysis system for example a portable peritoneal dialysis system (PPDS) during a one or more treatment cycles. In some embodiments, a treatment cycle comprising infusing fresh dialysate, dwelling of the dialysate inside the peritoneum cavity of the patient and draining the dialysate or draining of dialysate, infusion of fresh dialysate and dwelling of dialysate within the peritoneal cavity. Alternatively the PPDS is disconnected from the patent during the dwelling time. In some embodiments, when the PPDS is connected to the patient some of the dialysate is drained, for example to monitor a physiological condition of the patient and/or the efficacy of the treatment. In some embodiments, partial replacements of the dialysate are performed during the dwelling time, for example 10%, 20%, 30% 50%, 60% 70% or any intermediate smaller or larger percentage of the dialysate within the peritoneum is drained and optionally replaced with fresh dialysate.

According to some embodiments, the dialysis system is portable and is configured to be secured to a body part of the patient by a belt, a harness or any adaptor. In some embodiments, the dialysis system comprises a durable unit which comprises a motor, for example an electric motor and a battery, optionally a rechargeable battery electrically connected to the rotor. In some embodiments, the durable unit comprises a control circuitry electrically connected to the motor and to the battery. In some embodiments, the control unit controls the activation of the motor according to the power level in the battery. In some embodiments, the durable unit comprises an interface connected to the control circuitry, configured to provide at least one human detectable indication, for example an alert signal by a light indication and/or a sound indication. In some embodiments, when the power level in the battery is lower than a predetermined value, then the control circuitry signals the interface to generate an alert signal, for example a signal indicating to charge the battery or to replace the battery. Alternatively or additionally, when the power level in the battery is lower than a predetermined value, the control circuitry stops the operation of the motor.

According to some embodiments, the control circuitry activates the motor in a power saving mode, for example when the power level in the battery is lower than a predetermined value. In some embodiments, the control circuitry modifies at least one activation parameter of the motor, for example rotation speed and/or rotation duration, optionally when activating the motor in a power saving mode. In some embodiments, the control circuitry prevents the activation of the motor when the battery power level is lower than a predetermined value.

According to some embodiments, the power level in the battery when the battery is fully charged is sufficient for at least one dialysis treatment session, for example 2 treatment sessions, 3 treatment sessions, 4 treatment sessions or any smaller, intermediate or larger number of treatment sessions. In some embodiments, a treatment session includes at least partly draining of dialysate from the peritoneal cavity and at least partly infusion of fresh dialysate into the peritoneal cavity. Alternatively, a treatment session includes at least partly draining of dialysate from the peritoneal cavity, at least partly infusion of fresh dialysate into the peritoneal cavity and the dwelling time of the dialysate within the peritoneal cavity.

Optionally, the dialysis system does not include a heater, for example a dialysate heater. In some embodiments, the dialysis system does not include the heater, for example to save battery power and/or to lower the overall weight of the dialysis system.

According to some embodiments the weight of the dialysis system is in a range of 500 gr to 5 kg (5000 gr), for example 1 kg, 1.5 kg, 2 kg, 2.5 kg or any intermediate smaller or larger weight. Optionally the weight of the dialysis system is below 4000 gr. In some embodiments, the length of the device is in a range of 100 mm to 450 mm, for example 100 mm, 150 mm, 170 mm, 200 mm or any intermediate, smaller or larger value. In some embodiments, the width of the device is in a range of 80 mm to 300 mm, for example 100 mm, 130 mm, 150 mm or any intermediate, smaller or larger value.

According to some embodiments, the dialysis system comprises at least one connecting member, for example a harness, a belt or an adaptor, configured to secure the system to at least one body part of the patient, for example to the hips, leg, shoulder or thigh.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Device

Reference is now made to FIG. 1, describing a system or a device for a peritoneal dialysis treatment, according to some embodiments of the invention.

According to some exemplary embodiments, system 100 comprises a device 102, a dialysate bag 124 or a draining bag, and a patient catheter connected to a patient 130. In some embodiments, the device 102 is connectable to the dialysate bag 124 and/or to the draining bag, and optionally to form a disinfected flow path between the bags and the patient 130.

According to some exemplary embodiments, the device 102 comprises a controller 104 a fluid handling module 112, which optionally comprises a pump. In some embodiments, the controller 104 controls the operation of the fluid handling module, for example when the fluid handling module is activated to infuse dialysate into the peritoneal cavity, or when the fluid handling module is activated to drain the peritoneal cavity. In some embodiments, the controller 104 controls the connection of the dialysate bag 124 and/or the draining bag to the device 102. Additionally, the controller 104 controls the connection of a patient catheter to the device 102.

According to some exemplary embodiments, the controller 104 monitors and controls the automatic connection and disinfection of different components connected to the flow path. In some embodiments, the delivers an indication, for example a human detectable indication when a component is connected to the flow path and/or when the flow path is disinfected. Alternatively or additionally, the controller stores the indication in a memory.

According to some exemplary embodiments, the controller 104 monitors the flow within the flow path by different sensors of the device 102, for example fluid dynamic sensors 116. In some embodiments, the fluid dynamic sensors comprise at least one volume sensor, for example for monitoring the volume of fluid padding through the flow path. Additionally, the fluid dynamic sensors comprise at least one temperature control sensor, for example for monitoring and controlling the temperature of fluid passing through the flow path.

According to some exemplary embodiments, the device 102 comprises at least one clinical sensor 114 for example for sensing changes in clinical parameters. In some embodiments, the at least one clinical sensor senses the chemical and/or biological content of the drained dialysate, for example using a creatinine sensor, and/or a urea sensor. In some embodiments, the at least one clinical sensor 114 comprises a dextrose sensor 132, for example for sensing the dextrose levels in the drained dialysate. Optionally, the dextrose sensor 132 senses the dextrose levels in the infused dialysate. In some embodiments, a clinical condition of the subject is based on a comparison between the dextrose levels in the drained dialysate and the dextrose levels in the infused dialysate in addition to the measuring time and/or body mass of the subject.

According to some exemplary embodiments, the device 102 comprises at least one sensor for detection of Urea levels, for example Urea sensor 134. In some embodiments, a clinical condition of a patient is determined based on the measured urea levels in combination with the measuring time and/or the body mass of the subject.

According to some exemplary embodiments, the device 102 comprises at least one glucose sensor 132 configured to measure glucose levels in the dialysate. In some embodiments, a clinical condition of a patient is determined based on comparison between the levels of glucose in the drained dialysate and the glucose levels in the fresh dialysate in addition to the measuring time and/or body mass of the patient. Alternatively, the glucose levels in the drained dialysate and optionally compared to the infused dialysate or stored values indicate the dialysis efficacy and/or are indicative of the condition of the peritoneum membrane. In some embodiments, the device 102 comprises at least one sensor for detection of creatinine levels in the dialysate. In some embodiments, the levels of creatinine in the drained dialysate optionally, compared to the creatinine levels in the fresh dialysate, are indicative of the clinical condition of the subject. Alternatively, the creatinine levels are indicative of the dialysis efficacy and/or indicative of the condition of the peritoneum membrane. In some embodiments, the clinical sensors 114 are activated during a treatment session, for example during the infusion and/or draining of the dialysate.

According to some exemplary embodiments, the controller delivers indications and/or alerts to a patient or to a caregiver in the vicinity of the device 102. Alternatively or additionally, the controller transmits indications and alerts to a remote computer, for example a computer of a physician. In some embodiments, the physician transmits information to the device 102, for example to modify at least one treatment parameter or to select a different treatment plan.

According to some exemplary embodiments, the device 102 delivers time reminders to a patient and/or indications to perform a treatment step. In some embodiments, the user of the device, for example the patient or a caregiver provides user input through a user interface, which is optionally comprises at least one button, for example an activation or a treatment termination button. In some embodiments, the input received from the user and additional user data are stored in the device 102. In some embodiments, the stored user data is transmitted to a physician, for example to allow remote monitoring of the user condition throughout the treatment process. Additionally, the device 102 activation log files are also stored, and are optionally used to generate a patient compliance report following a treatment session.

According to some exemplary embodiments, the device 102 further comprising a battery 106, for example a rechargeable battery, to allow the activation of the controller 104 and/or an electric pump optionally connected to the fluid handling module 112. Alternatively the battery is electrically connected to an electric motor optionally connected to the fluid handling module 112. In some embodiments, the device 102 comprises a charging socket or plug electrically connected to the battery, for example to allow electrical charging of the battery by an external power source. Alternatively, the battery is a replaceable battery.

According to some exemplary embodiments, device 102 is connected to a computer server, for example server 105. In some embodiments server 105 stores treatment protocols and/or device activation log files. In some embodiments, controller 104 writes into server 105 measured values of parameters related to the device operation and/or parameters related to the clinical condition of the patient. Optionally, a physician communicates with the server 105, for example to receive log files of the device and/or to deliver treatment instructions or modifications. In some embodiments, the server 105 transmits information to a caregiver, for example a nurse or a warehouse, for example to supply new dialysate bags.

According to some exemplary embodiments, the device 102 communicates with a caregiver 103, for example to provide the caregiver clinical information of the patient and/or other information related to the treatment. In some embodiments, the device 102 communicates with a physician 109. In some embodiments, the device 102 delivers alerts to the physician 109 if actual treatment is different from a pre-determined treatment. Alternatively or additionally, the device 102 delivers alerts to the physician 109, if a desired outcome of the treatment is not reached. In some embodiments, the physician 109 communicates with the patient through the device 102, for example to deliver instructions and/or to receive more information from the patient.

According to some exemplary embodiments, the device 102 is connected to or comprises a bag switcher 107. In some embodiments, the device 102, optionally a detachable and/or portable device is attached to the bag switcher 107 during a peritoneal dialysis treatment, for example an exchange process. In some embodiments, at least one dialysate bag, for example bag 124 is connected to the bag switcher 107. In some embodiments, the bag switcher 107 validates that the correct bag is connected, optionally using a barcode or a different ID of the bag. In some embodiments, the bag switcher 107 monitors the temperature of the bag, and optionally heats the bag using a heating mechanism. In some embodiments, when the exchange session is over the detachable device is disconnected from the bag switcher 107.

According to some exemplary embodiments, the device comprises a warmer, for example warmer 111. Alternatively, the warmer is part of system 100 and/or is part of bag switcher 107. In some embodiments, the warmer is used to monitor and/or control the temperature of the dialysate bags. In some embodiments, the controller 104 receives signals from the warmer 111 or from a temperature sensor regarding the temperature of the dialysate. In some embodiments, the controller 104 signals the warmer 111 to heat the dialysate fluid, for example by heating the dialysate bag. Alternatively, the controller 104 signals the bag switcher 107 to switch the dialysate bag to a bag with a desired dialysate temperature.

According to some exemplary embodiments, the device 102 communicates with a handheld device 123, for example a cellular phone. In some embodiments, the device 102 transmits alerts and/or indications and/or information to the handheld device 123. Optionally, the device 102 communicates with the handheld device 123 using an application program installed in the device. In some embodiments, the device 102 delivers time alerts prior to initiation of a treatment or any time alert to the handheld device 123. In some embodiments, the handheld device controls at least partially the activation of device 102, optionally using the application program. In some embodiments, the device 102 receives information from devices connected to the handheld device 123, for example a smart watch or any other wearable sensor.

Figure 2:
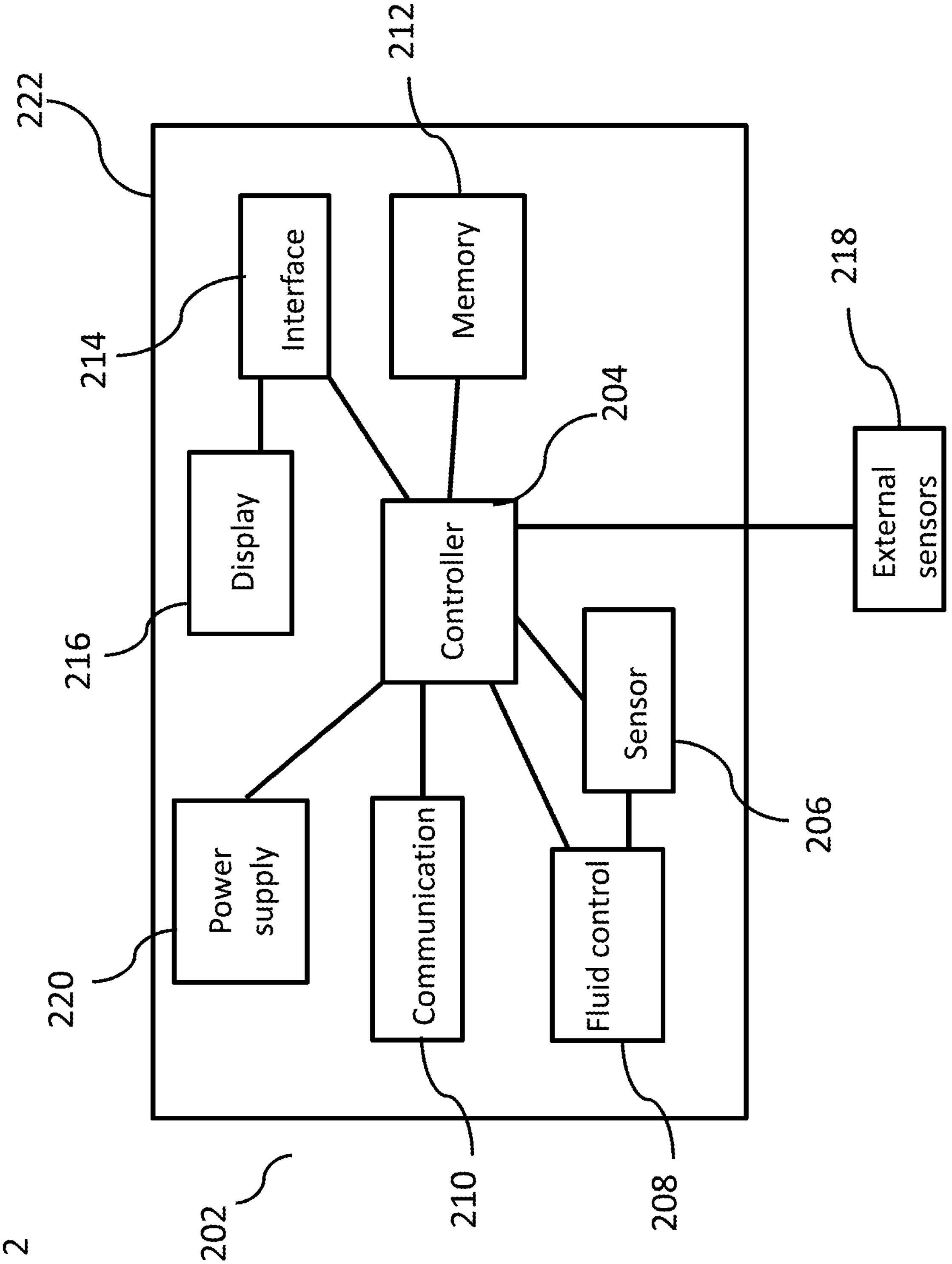
FIG. 2 is a block diagram of a device for monitoring and adjusting a dialysis treatment, according to some embodiments of the invention.

Reference is now made to FIG. 2 depicting the components of a device for monitoring and modifying a peritoneal dialysis treatment, according to some embodiments of the invention.

According to some exemplary embodiments, device 202 comprises a controller 204, which optionally functions as controller 104. In some embodiments, controller 204 is connected to a fluid control 208, which monitors and/or controls the fluid flow through the device 202. In some embodiments, the fluid control 208 monitors the connection of different bags, for example a dialysate bag or a draining bag to a flow path into a patient catheter. Optionally, the fluid control 208 monitors the connection of the patient catheter to the flow path. In some embodiments, the fluid control monitors and/or controls a disinfection of the flow path to and from the patient catheter.

According to some exemplary embodiments, the device 202 comprises at least one sensor 206 connected to the controller 204 and/or to the fluid control 208. In some embodiments, sensor 206 monitors fluid flow parameters within the flow path, for example temperature of the fluid, pressure and/or volume of the fluid that passes through the flow path in a selected time period. Alternatively, sensor 206 senses the content of the drained dialysate during the draining process. In some embodiments, sensor 206 senses the chemical and/or mineral and/or the biological content of the drained dialysate, for example creatinine levels, dextrose levels, and/or urea levels.

According to some exemplary embodiments, sensor 206 senses at least one parameter associated with an inflammation process. In some embodiments, the sensor 206 senses the turbidity level of the drained dialysate. In some embodiments, the turbidity level is an indicator to the bacteria and inflammation levels inside the drained dialysate and the peritoneal cavity. Alternatively or additionally, the sensor 206 senses at least one biological parameter, for example the level of white blood cells like neutrophils and/or the level of pro-inflammatory cytokines.

According to some exemplary embodiments, the at least one sensor, for example sensor 206 comprises an optical sensor for measuring one or more optical parameters, for example light absorption and/or light scattering of light passing through fresh dialysate and/or drained dialysate. In some embodiments, the at least one optical sensor is configured to measure light absorption and/or scattering in one or more wavelengths in a range of 500-650 nm, for example in a range of 500-600 nm, in a range of 550-620 nm, in a range 530-630 nm or any intermediate, smaller or larger wavelength range. Additionally or alternatively, at least one additional sensor measures at least one optical parameter, for example absorption and/or scattering of light passing through the fresh and/or drained dialysate in one or more wavelengths in a wavelength range of 150-350 nm, for example 150-250 nm, 200-300 nm, 250-350 nm or any intermediate smaller or larger range of wavelengths. In some embodiments, the at least one sensor comprises a sensor for measuring absorption and/or scattering in the visible light spectrum. In some embodiments, a combination of at least two sensors is used, for example to determine levels of white blood cells and/or for detecting peritonitis. In some embodiments, the at least one sensor configured to measure light absorption and/or light scattering is used for detect bubbles in the dialysate fluid and/or to determine fluid quantity and/or flow velocity.

According to some exemplary embodiments, the controller is connected via a wired or a wireless connection to at least one external sensor 218. In some embodiments, external sensor 218 measures at least one clinical parameter of the patient, for example blood pressure, body temperature, heart rate or other clinical parameters of the patient. In some embodiments, external sensor 218 is a wearable sensor, for example a sensor that is connected to the hand wrist of the patient. In some embodiments, sensor 206 is configured to measure similar clinical parameters of the patient as external sensor 218.

According to some exemplary embodiments, controller 204 is connected to interface 214, for example to receive input from a patient or a caregiver. In some embodiments, interface 214 comprises at least one button, for example an activation button or a treatment termination button. In some embodiments, the device 202 delivers indications and alerts using interface 214 to the patient and/or to the caregiver located in the vicinity of the device. In some embodiments, the interface 214 delivers a human detectable indication, for example a light indication. In some embodiments, the interface comprises a display 216, for example to visually deliver information to the patient. In some embodiments, the indications and/or the data delivered by the interface 214 include treatment-related reminders, treatment-related instructions, and alerts, for example safety alerts.

According to some exemplary embodiments, the device 202 comprises a communication module 210, for example to deliver and receive information to and from remote devices. In some embodiments, the communication module 210 comprises a wireless receiver and a wireless transmitter. In some embodiments, the communication module 210 wirelessly transmits indications, alerts, and treatment-related information to a remote computer or a remote handheld device. In some embodiments, the communication module receives wireless transmission from different device, for example a remote computer, at least one sensor optionally attached to the patient, or a remote handheld device. In some embodiments, the communication module 210 is configured to receive and transmit Wi-Fi signals, infrared signals and/or Bluetooth signals.

According to some exemplary embodiments, the device 202 comprises a power supply 220, for example an electrical power supply. In some embodiments, power supply 220 comprises at least one rechargeable battery, for example a lithium ion battery that is optionally detachable from the device 202. In some embodiments, the device 202 is connected to a base unit or placed inside a cradle between treatment sessions, for example to charge the battery and/or to download or upload information from memory storage inside the base unit. In some embodiments, the device 202 comprises a charging socket or a charging plug for example to allow electrical charging of the battery by an external power source.

According to some exemplary embodiments, the device 202 comprises a memory 212, for storing treatment plans, patient-related information, log files of the device or any other information related to the patient, the treatment and/or the device. In some embodiments, controller 204 writes information into the memory 212 or reads information from the memory 212 during a treatment session and/or between treatment sessions.

Exemplary Process for Modifying a Treatment During a Treatment Session

Figure 3:
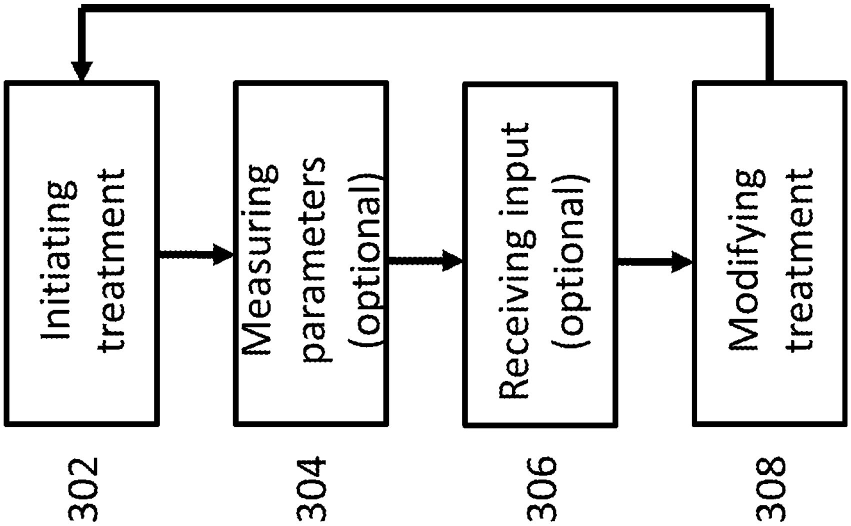
FIG. 3 is a flow chart of a general process for modifying a dialysis treatment during a treatment session, according to some embodiments of the invention.

According to some exemplary embodiments, a peritoneal dialysis treatment is modified during a treatment session, for example during the infusion of dialysate into the peritoneal cavity or during the draining of the dialysate. In some embodiments, the treatment is modified following measurements and/or input received during the treatment session. A possible advantage of modifying a treatment during a treatment session is the ability to adjust a pre-determined treatment to the clinical condition of the patient during the treatment session itself, for example to allow a more personalized treatment. Reference is now made to FIG. 3, depicting a process for modifying a treatment during a treatment session, according to some embodiments of the invention. In some embodiments, the treatment is modified during a peritoneal dialysis exchange cycle that is used for example to refresh the fluid in the peritoneal cavity. In some embodiment, the treatment is modified during the dwelling time of the dialysate within the peritoneal cavity. In some embodiments, the peritoneal dialysis filtration process takes place during the dwelling time of the dialysate, where waste and excess water are extracted from the blood.

According to some exemplary embodiments, a peritoneal dialysis treatment is initiated at 302. In some embodiments, the treatment is a pre-determined treatment, for example a treatment that was selected by a physician based on a previous clinical condition of a patient. In some embodiments, a dialysate infusion process or a dialysate draining process is initiated at 302.

According to some exemplary embodiments, different parameters are measured at step 304 during the treatment session. In some embodiments, the parameters are measured by a peritoneal dialysis device, for example device 202. In some embodiments, the device measures treatment related parameters, for example fluid flow duration, fluid pressure, and/or fluid volume at 304. Optionally, the device measures the content of fluid, for example the chemical, mineral and/or biological content of the fluid. Alternatively or additionally, the device measures clinical parameters of the patient, for example heart rate, body temperature, blood pressure, body weight or any other clinical parameter relevant to the treatment.

According to some exemplary embodiments, input is received at 306. In some embodiments, the input comprises input received from a user, for example when the user wants to terminate the current treatment session and/or when the user is not feeling well during the treatment session. Alternatively or additionally, the input received at 306 comprises input from a physician or a remote expert.

According to some exemplary embodiments, the treatment is modified at 308. In some embodiments, the treatment is modified based on the parameters measured at 304 and/or based on the input received at 306. In some embodiments, the treatment is modified by modifying the treatment parameters or by selecting a different treatment plan. In some embodiments, the treatment, which is a pre-determined treatment, is modified to adhere to the current clinical condition of the patient. Alternatively or additionally, the pre-determined treatment is modified to adapt to the current treatment status. In some embodiments, after the treatment is modified at 308, the modified treatment initiates at 302.

Exemplary Process for Modifying a Treatment Between Treatment Sessions

Figure 4:
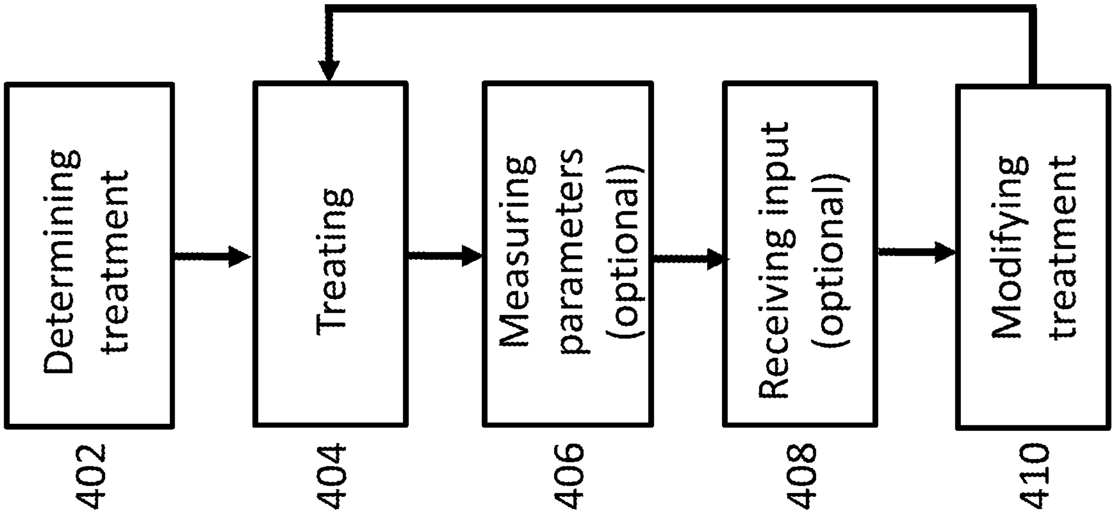
FIG. 4 is a flow chart of a general process for modifying a dialysis treatment before treatment sessions, according to some embodiments of the invention.

According to some exemplary embodiments, a peritoneal dialysis treatment is modified between treatment sessions, for example between an infusion of dialysate into the peritoneal cavity to the draining of the dialysate. Alternatively or additionally, the treatment is modified between cycles of infusion and draining. In some embodiments, the treatment is modified following measurements and/or input received between the treatment sessions. A possible advantage of modifying a treatment between treatment sessions is the ability to adjust a pre-determined treatment to the clinical condition of the patient during the actual treatment, for example to allow a more personalized treatment. Reference is now made to FIG. 4, depicting a process for modifying a treatment between treatment sessions, according to some embodiments of the invention.

According to some exemplary embodiments, a peritoneal dialysis treatment is determined at 402. In some embodiments, the treatment and/or the treatment parameters are determined based on the clinical condition of the patient during pre-treatment examinations.

According to some exemplary embodiments, the patient is treated at 404, according to the pre-determined treatment parameters. In some embodiments, a dialysate is infused into the peritoneal cavity at 404. Alternatively or additionally, the dialysate is drained at 404.

According to some exemplary embodiments, when the treatment is over, parameters are measured at 406. In some embodiments, the parameters are measured by a peritoneal dialysis device, for example device 202. In some embodiments, the device measures treatment related parameters, for example fluid flow duration, fluid pressure, and/or fluid volume at 406. Optionally, the device measures the content of fluid, for example the chemical, mineral and/or biological content of the fluid. Alternatively or additionally, the device measures clinical parameters of the patient, for example heart rate, body temperature, blood pressure, body weight or any other clinical parameter relevant to the treatment.

According to some exemplary embodiments, input is received at 408. In some embodiments, the input comprises input received from a user following the treatment, for example when the user wants to reschedule the next treatment session or other treatment-related events and/or when the user is not feeling well following the treatment session. Alternatively or additionally, the input received at 406 comprises input from a physician or a remote expert. In some embodiments, the physician or experts transmits input based on the treatment compliance of the patient or the parameter measurements at 406.

According to some exemplary embodiments, the treatment is modified at 410. In some embodiments, the treatment is modified based on the measurements at 406 and/or based on the input received at 408. In some embodiments, at least one treatment session, for example a dialysate infusion session or a dialysate draining session is modified. In some embodiments, a treatment session following the measurements is modified. Alternatively, an alternative treatment or a different treatment plan is selected. In some embodiments, the modified treatment initiates at 404.

Exemplary Process for Modifying a Treatment Due to Treatment Variations

Figure 5:
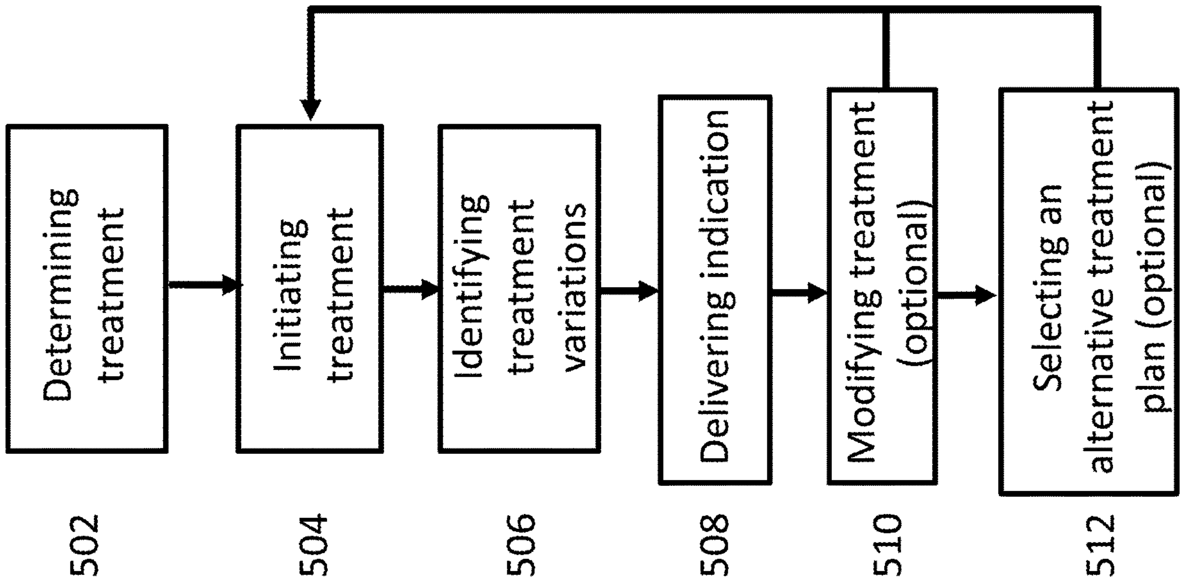
FIG. 5 is a flow chart of a general process for modifying a dialysis treatment following variations in actual treatment, according to some embodiments of the invention.

According to some exemplary embodiments, a peritoneal dialysis device, for example device 202 monitors and controls a peritoneal dialysis treatment. In some embodiments, pre-determined treatment parameters are automatically modified by the device during the treatment. In some embodiments, the pre-determined treatment parameters are modified when variations between the actual treatments and the pre-determined treatment are identified. Reference is now made to FIG. 5, depicting a process for modifying a treatment due to treatment variations. In some embodiments, the pre-determined treatment is modified based on variations detected in a peritoneal dialysis exchange cycle that is used for example to refresh the fluid in the peritoneal cavity. In some embodiment, the pre-determined treatment is modified based on variations detected during the dwelling time of the dialysate within the peritoneal cavity. As described herein, the peritoneal dialysis filtration process takes place during the dwelling time of the dialysate, where waste and excess water are extracted from the blood.

According to some exemplary embodiments, a treatment plan is determined at 502. In some embodiments, the treatment parameters are determined, for example the duration of dialysate infusion and/or the duration of dialysate draining. Additionally, the volume of the infused dialysate and the dialysate content are determined. In some embodiments, the time interval between dialysate infusion and dialysate is also determined at 502.

According to some exemplary embodiments, the treatment is initiated at 504. In some embodiments, the treatment is initiated according to the treatment parameter that were determined at 502.

According to some exemplary embodiments, treatment variations are identified at 506. In some embodiments, the peritoneal dialysis device, for example device 202 identifies variations between the pre-determined treatment and the actual treatment.

According to some exemplary embodiments, an indication is delivered at 508. In some embodiments, an indication is delivered at 508 if treatment variations are identified at 506. In some embodiments, the indications are delivered to a user of the device, for example to a patient or to a caregiver. Alternatively, the indications are delivered to a physician or an expert.

According to some exemplary embodiments, the treatment is modified at 510. In some embodiments, the pre-determined treatment and/or the predetermined treatment parameters are modified at 510. In some embodiments, timing parameters of the treatment, for example the duration of the dialysate infusion or the dialysate draining are modified. In some embodiments, the volume of the infused dialysate and/or the drain dialysate is modified. In some embodiments, the treatment and/or the treatment parameters are automatically or semi-automatically modified by the device.

According to some exemplary embodiments, an alternative treatment plan is selected at 512. In some embodiments, the alternative treatment plan is stored in a memory of the device, for example memory 212. In some embodiments, the alternative treatment plan is selected using an algorithm stored in a memory of the device, for example memory 212. In some embodiments, once the treatment is modified at 510, the modified treatment initiates at 504. In some embodiments, once an alternative treatment plan is selected at 512, the alternative treatment plan initiates at 504.

Exemplary Process for Monitoring Treatment Compliance

Figure 6:
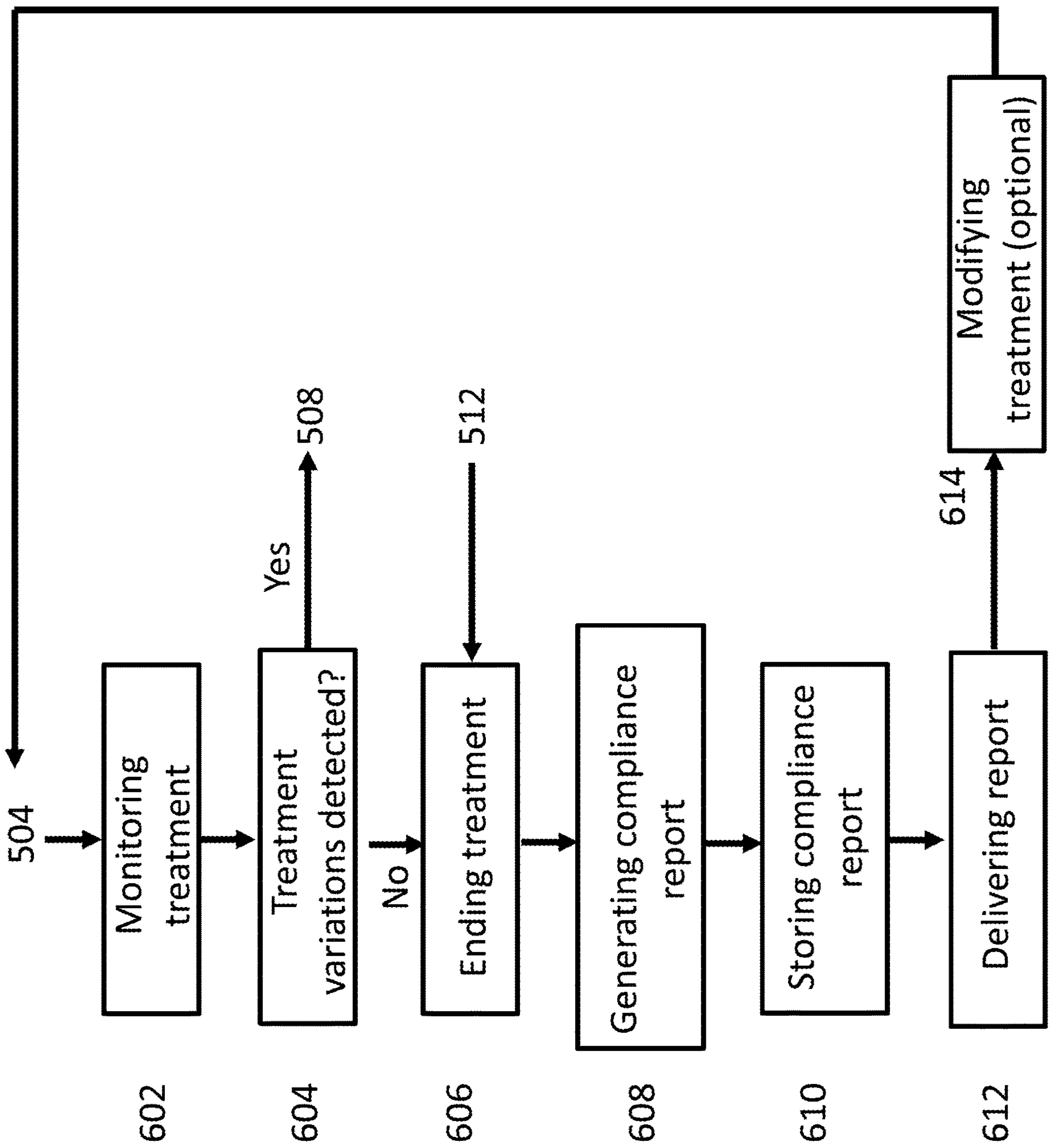
FIG. 6 is a flow chart of a process for monitoring a patient compliance with a dialysis treatment, according to some embodiments of the invention.

According to some exemplary embodiments, the patient's compliance to the peritoneal dialysis treatment is monitored, for example to allow better disease and treatment management. In some embodiments, the treatment compliance is monitored by a peritoneal dialysis device, for example device 202. Reference is now made to FIG. 6, depicting a process for monitoring treatment compliance according to some embodiments of the invention.

According to some exemplary embodiments, a treatment is monitored at 602, after it was initiated as previously described at 504. In some embodiments, the treatment is monitored by at a peritoneal dialysis device, for example device 202. In some embodiments, the device monitors the treatment using at least one sensor for example a fluid flow related sensor or a clinical sensor. Alternatively or additionally, the device monitors the connection of a dialysate bag and/or a draining bag to a patient's catheter through at least one connector of the device. In some embodiments, the device monitors the formation of a disinfected flow path into the patient's catheter. In some embodiments, the device monitors the interaction of a user with the device, for example activation of the device, activation and/or termination of the device. In some embodiments, the device monitors the disconnection of the dialysate bag and/or the draining bag and/or the draining catheter from the device. Optionally, the device monitors connection and disconnection to the fluid handling module 112.

According to some exemplary embodiments, the device monitors the duration of the treatment and/or the duration of each treatment session and the interval between consecutive treatment sessions. In some embodiments, the device records and stores at least some of the monitored data in a memory of the device, for example memory 212.

According to some exemplary embodiments, the device monitors and records any variation from the pre-determined treatment parameters, if such variations are detected at 604. Optionally, if variations are detected the device delivers an indication and/or a report to the user and/or to a physician.

According to some exemplary embodiments, the treatment, for example a treatment session ends at 606. In some embodiments, a compliance report is generated at 608. In some embodiments, the compliance report comprises a summary of at least some of the events that were monitored during the treatment. Alternatively or additionally, the compliance report comprises events that were monitored before and/or after the treatment, for example the delivery of treatment indications to the patient and the response of the patient to these indications.

According to some exemplary embodiments, the compliance report is stored at 610. In some embodiments, the compliance report is stored in a memory of the device. Alternatively, the compliance report is stored in an external memory, for example in a detachable memory or in an internet network remote memory.

According to some exemplary embodiments, the compliance report is delivered at 612. In some embodiments, the compliance report is delivered to the patient or to a caregiver. Alternatively or additionally, the compliance report is delivered to the physician or to an expert. In some embodiments, the compliance report is delivered during a scheduled update. Alternatively, the compliance report is delivered upon request.

According to some exemplary embodiments, the treatment and/or at least one treatment parameter is modified at 614. In some embodiments, the treatment is modified when the patient does not adhere to the treatment and/or treatment parameters. In some embodiments, the treatment is modified if according to the compliance report the delivered treatment or treatment session is different from the pre-determined treatment. In some embodiments, the modified treatment initiates at 504.

Exemplary Process for Determining a Clinical Condition Based on Drained Dialysate Content According to some exemplary embodiments, dialysate is drained from the peritoneum of a subject after a determined dwelling time. In some embodiments, the drained dialysate content is measured and optionally analyzed, for example to determine a clinical condition of the subject. In some embodiments, the clinical condition of the subject is determined based on the analysis of the drained dialysate content, the body mass of the subject and optionally the measuring time period.

Figure 7A:
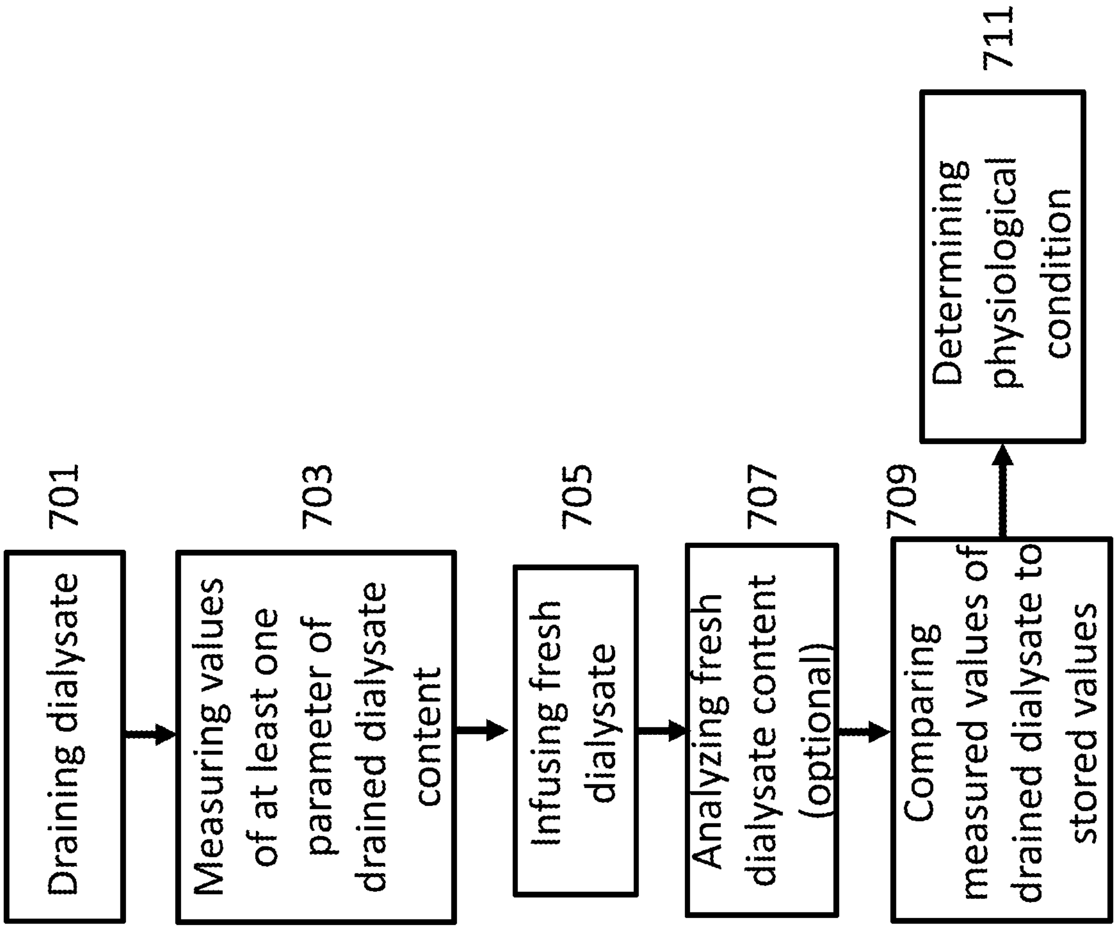
FIG. 7A is a flow chart of a process for determining a clinical condition based on the content of the drained dialysate, according to some embodiments of the invention.

Reference is now made to FIG. 7A depicting a general process for determining the clinical condition of a subject based on the drained dialysate, according to some exemplary embodiments of the invention.

According to some exemplary embodiments, dialysate is drained at 701. In some embodiments, the dialysate is drained from the peritoneum cavity of the subject, optionally after a desired dwelling time. In some embodiments, the dialysate is drained from the peritoneum through a catheter and into the tubing of a peritoneal dialysis system.

According to some exemplary embodiments, the drained dialysate content is analyzed at 703. In some embodiments, the content of the drained dialysate is measured by at least one sensor, for example an optic sensor, an electrical sensor or any other sensor capable of measuring at least one parameter related to the content of the drained dialysate. In some embodiments, the content of the drained dialysate is measured during a pre-determined time period. In some embodiments, the at least one parameter comprises turbidity level of the drained dialysate, light absorption and/or light scattering at selected wavelengths, white blood cells number, levels of cytokines, levels of metal ions, levels of chemical or biological compounds, for example dextrose or Urea, and/or levels of bioactive compounds in the drained dialysate. In some embodiments, the measured values are analyzed by a controller of the dialysis system.

According to some exemplary embodiments, fresh dialysate is infused into a subject body lumen, for example into the peritoneum at 705. In some embodiments, the fresh dialysate is infused by connecting a fresh dialysate bag to a peritoneal dialysis system that infuses the fresh dialysate through a catheter into the peritoneum.

According to some exemplary embodiments, the fresh dialysate content is analyzed at 707. In some embodiments, the fresh dialysate content passing through a tubing of the peritoneal dialysis tubing is analyzed. Alternatively or additionally, the fresh dialysate within the fresh dialysate bag is analyzed. In some embodiments, at least some of the data related to the content of the fresh dialysate is downloaded from a website, cloud memory storage, a remote server to a memory of the dialysis system. Optionally, the data is downloaded to the memory by scanning a code, for example a barcode, a QR code or any other code printed on the fresh dialysate bag, bag package or any document received with the fresh dialysate bag.

According to some exemplary embodiments, the content of the fresh dialysate is measured by at least one sensor, for example an optic sensor, an electrical sensor or any other sensor capable of measuring at least one parameter related to the content of the fresh dialysate. In some embodiments, the at least one parameter comprises turbidity of the dialysate solution, light absorption and/or light scattering at selected wavelengths, white blood cells number, levels of cytokines, levels of metal ions, levels of chemical or biological compounds, for example dextrose or Urea, and/or levels of bioactive compounds.

According to some exemplary embodiments, the analysis results and/or measured values of the drained dialysate content are compared to values or indications stored in the memory of the dialysis system at 709. In some embodiments, the analysis results and/or measured values of the drained dialysate content are compared to stored values of at least one parameter of the infused dialysate content. Alternatively, the analysis results and/or measured values of the drained dialysate content are compared to stored analysis results and/or measured values of a previously drained dialysate, for example for determining progress of a body condition According to some exemplary embodiments, a physiological condition of the subject is determined at 711. In some embodiments, the physiological condition of the subject is determined based on the analysis results. In some embodiments, the analysis results and/or measured values of the drained dialysate content are compared to the analysis results and/or measured values of the fresh dialysate. In some embodiments, the physiological condition of the subject is determined based on the comparison results. In some embodiments, the physiological condition of the subject is determined based on the comparison to the stored indications, optionally indications related to different clinical conditions. Alternatively, the physiological condition of the subject is determined based on identified variations in the analysis results and/or measured values of the drained dialysate. In some embodiments, the variations are between the analysis results and/or measured values to a previously determined baseline, and/or at least one reference value or indications thereof stored in the memory of the dialysis system. Additionally, the physiological condition is determined based on the body mass or weight of the subject and/or the time period in which the measured values were performed.

According to some exemplary embodiments, the physiological condition comprises one or more of peritonitis, pre-peritonitis, post-peritonitis, inflammation, pre-inflammation, diabetes, pre-diabetes, pathological condition caused by deficiency in a chemical and/or a biological compound.

Exemplary Process for Peritonitis Detection

Figure 7B:
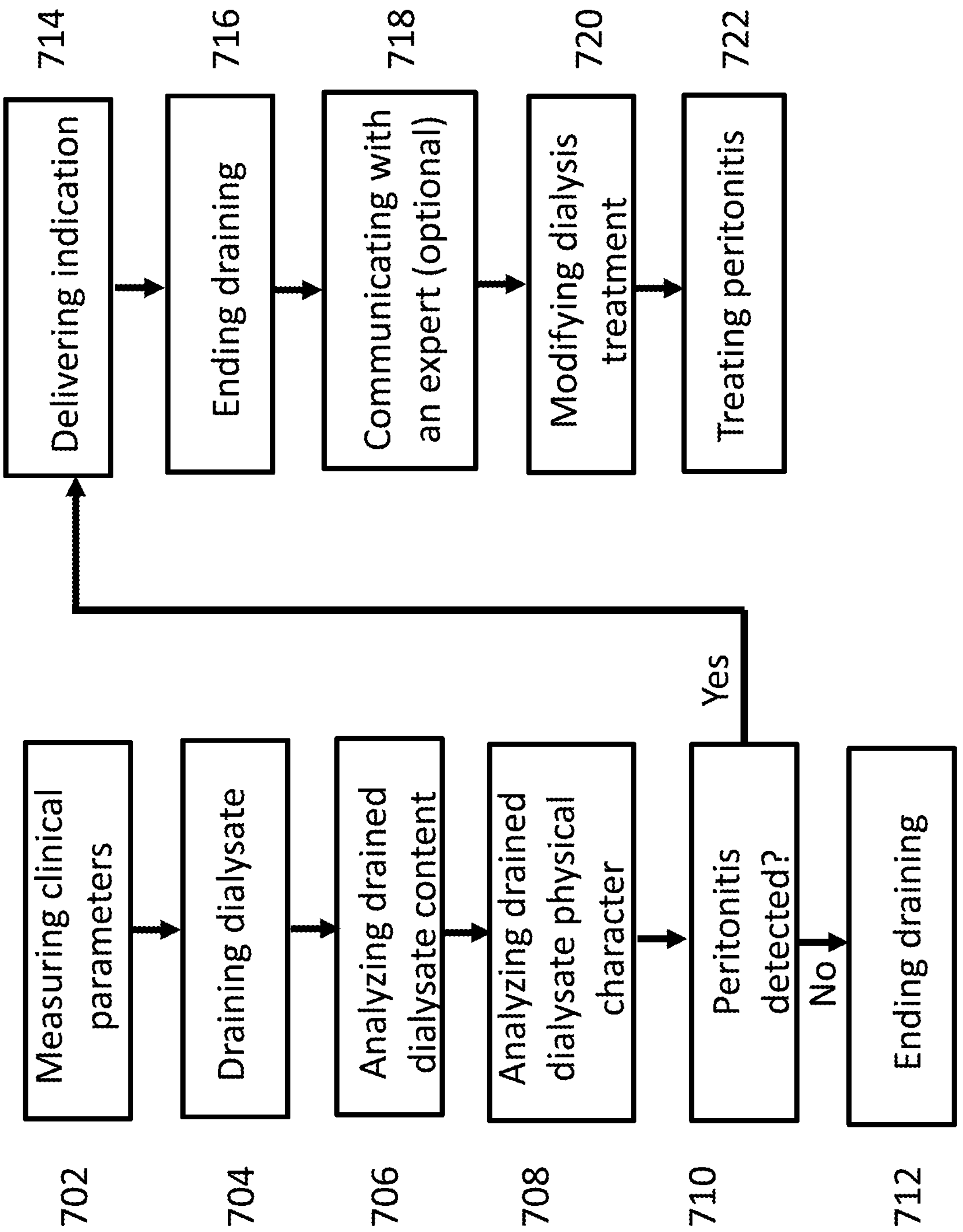
FIG. 7B is a flow chart of a process for detecting peritonitis, according to some embodiments of the invention.

According to some exemplary embodiments, one of the risks of a peritoneal dialysis treatment is an inflammation process also termed as peritonitis. In some embodiments, peritonitis is caused by the entry of bacteria from outside of the body, through the patient's catheter and into the peritoneal cavity. Since peritonitis affects the peritoneal dialysis treatment, it is important to try and detect peritonitis as early as possible to allow for example, a more efficient peritonitis treatment. Reference is now made to FIG. 7B depicting a process for peritonitis detection and optionally peritonitis treatment, according to some embodiments of the invention.

According to some exemplary embodiments, clinical parameters of a patient are measured at 702. In some embodiments the clinical parameters comprise body temperature, and/or white blood cell count or any clinical parameter indicative of an inflammation process. In some embodiments, the clinical parameters of the patient are measured between or during treatment sessions or before a dialysate draining process.

According to some exemplary embodiments, the dialysate is drained at 704. In some embodiments, some of the dialysate is drained during the dwelling time, for example to monitor the progression of the filtration process. In some embodiments, some of the dialysate is drained at least twice during the dwelling time. Optionally, some of the dialysate is drained during the dwelling time in pre-determined time points.

According to some exemplary embodiments, the dialysate content is analyzed at 706. In some embodiments, the dialysate content is analyzed while draining the dialysate. In some embodiments, the dialysate content is continuously analyzed or is analyzed in at least two type points while draining the dialysate. In some embodiments, the dialysate content is analyzed by directing some of the dialysate to a testing tube or to a testing channel.

According to some exemplary embodiments, the chemical and/or the biological composition of the drained dialysate is analyzed at 706. In some embodiments, the drained dialysate is analyzed for an amount of white blood cells which is above a pre-determined threshold. Alternatively or additionally, the number of neutrophils or any other white blood cell which is an indicator for peritonitis is analyzed. Optionally, the presence and/or the amount of pro-inflammatory cytokines in the drained dialysate is analyzed.

According to some exemplary embodiments, a physical character of the drained dialysate, for example the turbidity of the drained dialysate is analyzed at 708. In some embodiments, an increase in the cloudiness or haziness of the drained dialysate is an indication to the presence of bacteria and peritonitis. In some embodiments, the turbidity level is measured by a turbidity sensor which measures for example, the amount of light that is scattered by suspended solids in the fluid. Optionally, light absorption, light scattering and/or color of the drained dialysate are analyzed at 708.

According to some exemplary embodiments, if peritonitis is not detected at 710, the draining process ends at 712. According to some exemplary embodiments, if peritonitis is detected at 710, then an indication is delivered at 714 to the patient and/or to a caregiver and/or to a physician.

According to some exemplary embodiments, the draining process ends at 716. In some embodiments, an expert receives an indication at 718. In some embodiments, the expert transmits instructions for treating the peritonitis and/or for modifying the dialysis treatment.

According to some exemplary embodiments, the dialysis treatment is modified at 720. In some embodiments, the dialysis treatment is terminated or postponed following the detection of peritonitis. Alternatively, at least one treatment parameter is modified. In some embodiments, the dwelling time of the dialysate within the peritoneal cavity is modified. In some embodiments, the patient is instructed to bring a sample of the infected drained dialysate to a clinic or a laboratory for analysis, for example by a microbial culture. In some embodiments, the dialysis treatment is automatically terminated, or automatically postponed by the dialysis device following the detection of peritonitis. Alternatively, at least one treatment parameter is automatically modified by the dialysis device.

According to some exemplary embodiments, peritonitis is treated at 722. In some embodiments, peritonitis is treated by infusion of antibiotic-containing solutions into the peritoneal cavity. Optionally, an antibiotic is injected into the dialysate solution, prior to infusion. In some embodiments, peritonitis is treated by flushing the peritoneal cavity at least one time, for example with a washing solution prior to dialysate infusion. In some embodiments, peritonitis is automatically treated by the dialysis device, for example by automatically flushing the peritoneal cavity and/or automatically infusing antibiotics into the peritoneal cavity.

Figure 7C:
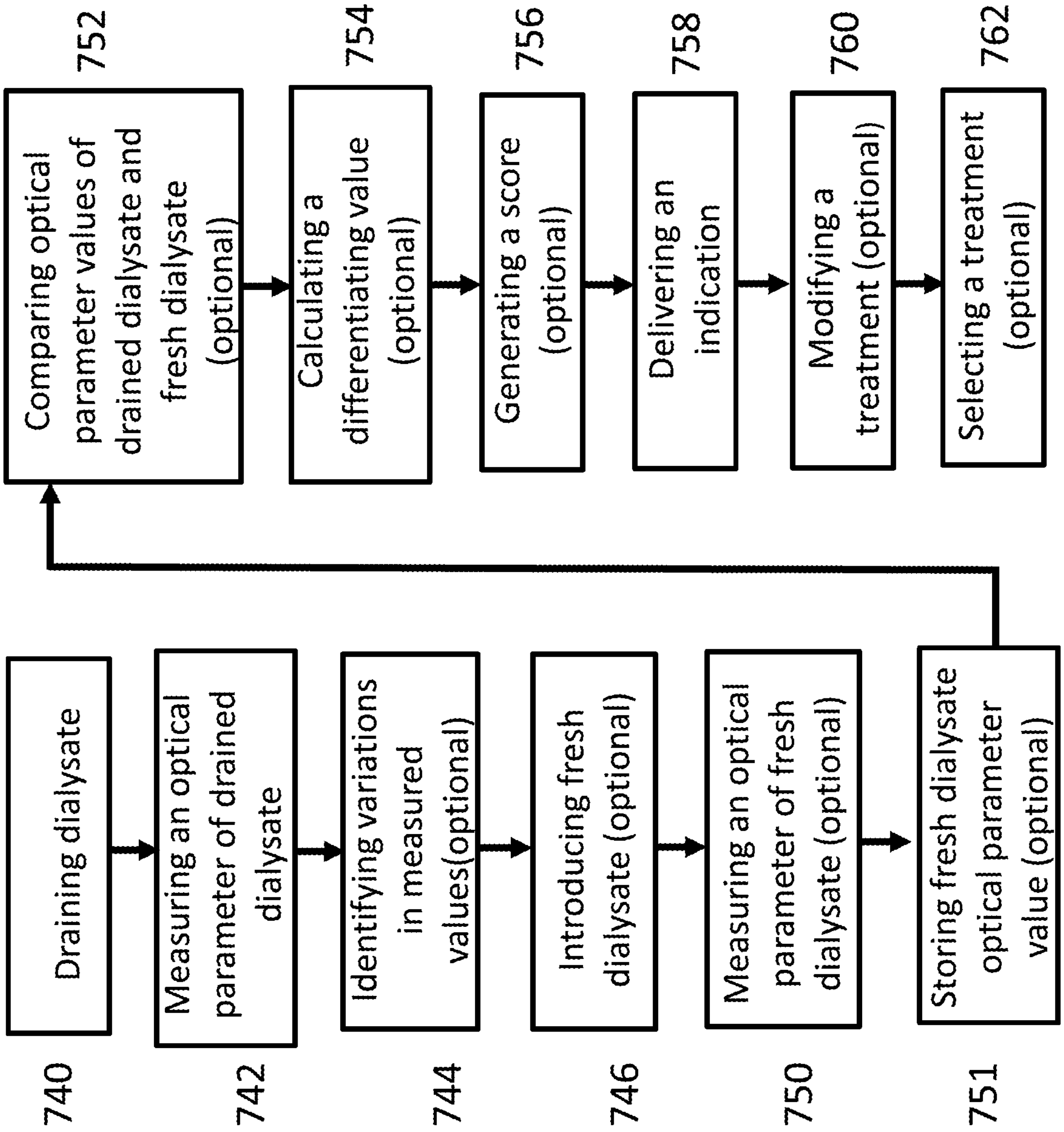
FIG. 7C is a flow chart of a process for detecting peritonitis by measuring absorption and/or scattering, according to some embodiments of the invention.

Reference is now made to FIG. 7C depicting a process for detection of peritonitis by measuring an optical parameter, for example absorption and/or scattering of light, according to some exemplary embodiments of the invention.

According to some exemplary embodiments, dialysate is drained from the peritoneal cavity at 740. In some embodiments, the dialysate is drained through a tubing of the dialysis device.

According to some exemplary embodiments, the absorption and/or scattering of light passing through the drained dialysate are measured at 742. In some embodiments, the absorption and/or scattering of light passing through the drained dialysate in the tube are measured. Alternatively, the absorption and/or scattering of light passing through the drained dialysate in a drained dialysate storage compartment are measured. Optionally, the measured absorption and/or scattering values or indications of the values, of the drained dialysate are stored in the memory, for example memory 212. In some embodiments, the light absorption and/or scattering is measured by at least one sensor positioned in the PPDS. Optionally, the at least one sensor is part of a durable unit. Alternatively, the at least one sensor is part of a disposable unit. In some embodiments, the at least one sensor measures absorption and/or scattering of light passing through the drained dialysate in a wavelength range of 500-650 nm, for example in a range of 500-600 nm, in a range of 550-620 nm, in a range 530-630 nm or any intermediate, smaller or larger wavelength range. Additionally or alternatively, at least one additional sensor measures absorption and/or scattering of light passing through the drained dialysate in a wavelength range of 150-350 nm, for example 150-250 nm, 200-300 nm, 250-350 nm or any intermediate smaller or larger range of wavelengths. In some embodiments, the additional sensor is configured to measure absorption and/or scattering of light in the visible light spectrum. In some embodiments, the light absorption and/or scattering is measured for each wavelength in the range of the wavelengths or for at least one selected wavelength in the range of wavelengths. In some embodiments, the absorption and/or scattering of light passing through the drained dialysate waste bag is measured According to some exemplary embodiments, variations in the measured values are identified at 744. In some embodiments, the identified variations are variations between the measured values and a predetermined baseline, at least one reference value or indications thereof, optionally stored in a memory of the dialysis system or device.

According to some exemplary embodiments, fresh dialysate is introduced into the peritoneum at 746. In some embodiments, the fresh dialysate passes through a tube of a peritoneal dialysis system, optionally a portable peritoneal dialysis system (PPDS).

According to some exemplary embodiments, an optical parameter, for example light absorption and/or scattering passing through the fresh dialysate is measured at 750. In some embodiments, the light absorption and/or scattering is measured by at least one sensor positioned in the PPDS. Optionally, the at least one sensor is part of a durable unit of the PPDS. Alternatively, the at least one sensor is part of a disposable unit of the PPDS. In some embodiments, the at least one sensor measures absorption and/or scattering of light passing through the fresh dialysate in a wavelength range of 500-650 nm, for example in a range of 500-600 nm, in a range of 550-620 nm, in a range 530-630 nm or any intermediate, smaller or larger wavelength range. Additionally or alternatively, at least one additional sensor measures absorption and/or scattering of light passing through the fresh dialysate in a wavelength range of 150-350 nm, for example 150-250 nm, 200-300 nm, 250-350 nm or any intermediate smaller or larger range of wavelengths. In some embodiments, the additional sensor is configured to measure absorption and/or scattering of light in the visible light spectrum. In some embodiments, the light absorption and/or scattering is measured for each wavelength in the range of the wavelengths or for at least one selected wavelength in the range of wavelengths. In some embodiments, the absorption and/or scattering of light passing through the fresh dialysate bag is measured.

According to some exemplary embodiments, the absorption and/or scattering values measured at 751 are stored in a memory at 744. Alternatively or additionally, indications of the values are stored in the memory. In some embodiments, the memory is part of the PPDS, for example memory 212 of the device 202 shown in FIG. 2. In some embodiments, the light absorption and/or scattering values are provided by the manufacture of the fresh dialysate solution. Optionally, the values are downloaded to the memory from a website of the manufacturer, for example by scanning a code on the fresh dialysate bag/box or a code in the package.

According to some exemplary embodiments, the measured light absorption and/or scattering values or indication of the drained dialysate and the fresh dialysate are compared at 752. Alternatively or additionally, the measured light absorption and/or scattering values or values indications of the drained dialysate are compared to stored indications and/or to a table in the memory. Optionally, the measured values or indications of the drained dialysate are compared to stored values or indication of a previously drained dialysate. Comparing drained dialysate measured parameter values to fresh dialysate measured parameter values, allows for example self-calibration, for example minimize variations due to different batches of fresh dialysate.

According to some exemplary embodiments, at least one differentiating parameter value is calculated based on the comparison results at 754. In some embodiments, the differentiating parameter comprises deviation and/or average deviation between the fresh dialysate absorption and/or scattering values and the drained dialysate absorption and/or scattering values.

According to some exemplary embodiments, a score is generated at 756. In some embodiments, the score is generated based on the at least one differentiating parameter value. Alternatively or additionally, the score is generated based on the measured light absorption and/or scattering values of the drained dialysate. In some embodiments, the score is generated based on a combination between the differentiating parameter value or the measured light absorption and/or scattering values and at least one clinical parameter of a subject, for example body temperature, treatment regime, administered drugs, age, blood pressure, background diseases, and/or indications related to white blood cells count. In some embodiments, the generated score is indicative of a contamination level of the dialysate fluid. Alternatively or additionally, the generated score is indicative of the number of white blood cells found in the drained dialysate or in a selected volume of the draineddialysate, for example in 1 ml, 10 ml, 100 ml, 1 liter of the drained dialysate or in any intermediate, smaller or larger volume of the drained dialysate. In some embodiments, the score is generated for each wavelength or for each range of wavelengths separately According to some exemplary embodiments, an indication is delivered at 758. In some embodiments the indication, for example a human detectable indication, is delivered to a user of the PPDS. Alternatively or additionally, the indication is delivered to a caregiver or an expert, for example a physician. Optionally, the indication is delivered by wireless signals to a remote computer or a handheld device. In some embodiments, the indication is based on the score generated at 756 and/or on the differentiating value calculated at 754. In some embodiments, the indication is based on the measured light absorption and/or scattering values of the drained dialysate, or on the indications of the values.

According to some exemplary embodiments, the indication is delivered at 758 if the generated score or the calculated differentiating value is higher than a predetermined value or not in a range of predetermined values, optionally stored in memory 212.

According to some exemplary embodiments, at least one parameter value of the treatment is modified at 760. Alternatively, at least part of the treatment protocol is modified at 760. In some embodiments, the parameter value and/or the treatment protocol are modified based on the generated score. Alternatively or additionally, the parameter value and/or the treatment protocol are modified based on the calculated differentiating value. In some embodiments, the treatment is modified, for example by including a wash step of the peritoneum cavity. Alternatively or additionally, the treatment is modified by shortening or lengthening the dwelling time of the dialysate within the peritoneal cavity. In some embodiments, the treatment is modified by changing the composition of the fresh dialysate used in the process, for example to an antibiotics-containing dialysate or to a dialysate that contains an antimicrobial or an antiviral bioactive component or drug.

According to some exemplary embodiments, a treatment is selected at 762. In some embodiments, the treatment is selected based on the generated score or based on the calculated differentiating value. In some embodiments, an antimicrobial and/or an antiviral treatment is selected. In some embodiment, the treatment is provided without changing the dialysis treatment regime, for example by administering antibiotic bioactive agents.

According to some exemplary embodiments, for selecting a treatment at 762 and/or for modifying a treatment at 760 light absorption and/or scattering values are measured in the two wavelength ranges of 500-650 nm and in the range of 150-350 nm, as indicated above. Alternatively, for selecting a treatment at 762 and/or for modifying a treatment at 760, light absorption and/or scattering values are measured in the two wavelength ranges of 500-650 nm and in the visible light spectrum. In some embodiments, the absorption and/or scattering values in the two wavelength ranges are measured by one, two or more sensors.

Exemplary Process for Optimizing Dialysis

Figure 8:
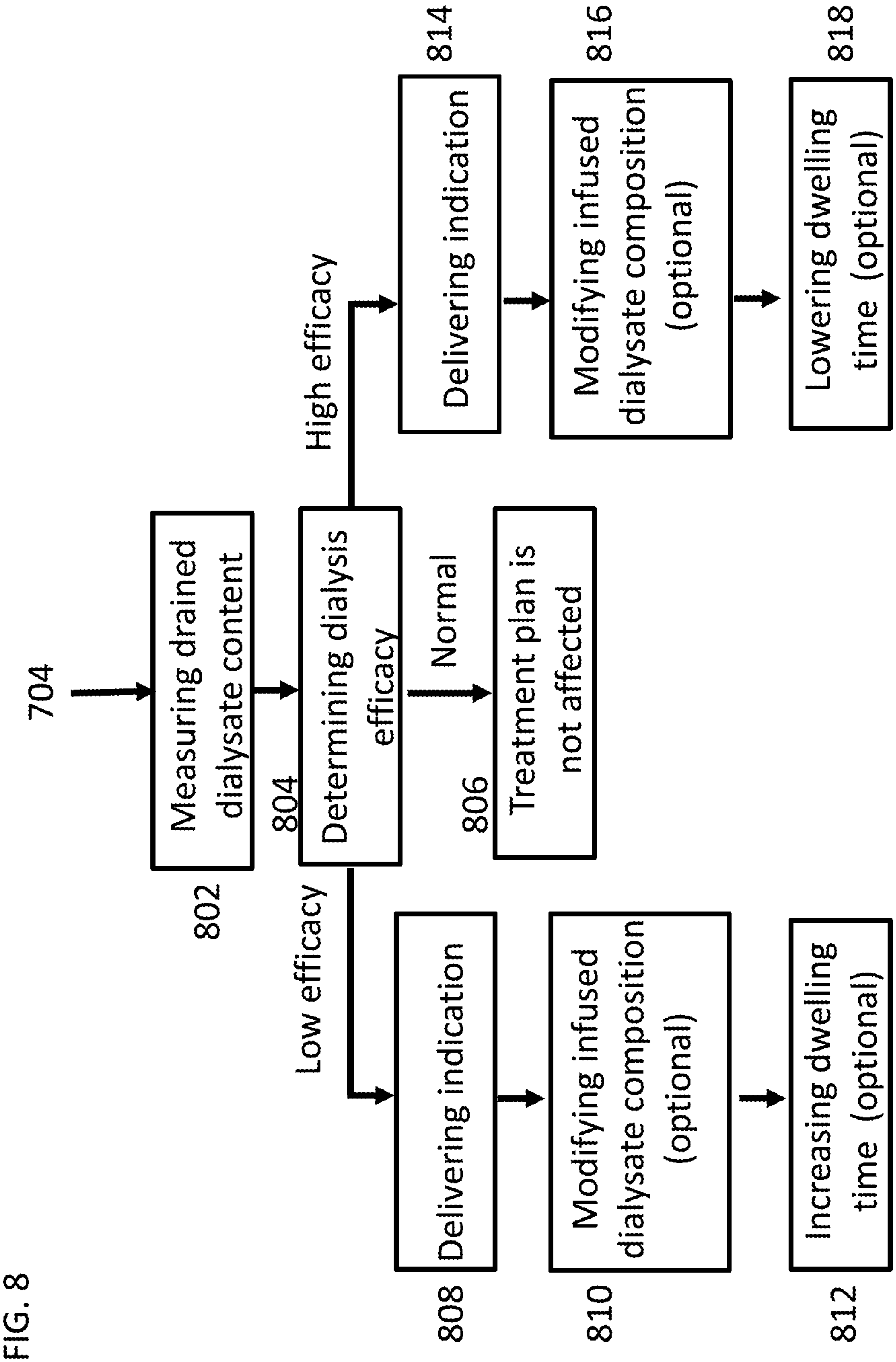
FIG. 8 is a flow chart of a process for optimizing a peritoneal dialysis treatment, according to some embodiments of the invention.

According to some exemplary embodiments, by measuring the chemical and/or biological composition of the drained dialysate it is possible to determine the efficacy of the dialysis treatment. In some embodiments, if the dialysis treatment is not efficacious, then at least one treatment parameter is modified, for example the content of the infused dialysate. Reference is now made to FIG. 8 depicting a process for optimizing a dialysis treatment, according to some embodiments of the invention.

According to some exemplary embodiments, the dialysate is drained from the peritoneal cavity at 704. According to some exemplary embodiments, the drained dialysate content is measured at 802. In some embodiments, the chemical and/or mineral and/or biological properties of the drained dialysate are measured at 802, for example the creatinine levels, the urea levels and the ionic strength of the drained dialysate. In some embodiments, the ionic strength of the drained dialysate is a measure of the concentration of ions in the drained solution. In some embodiments, the level or concentration of dextrose in the drained dialysate, optionally in comparison to the infused dialysate, is an indicator of the ionic strength.

According to some exemplary embodiments, the drained dialysate content is measured by at least one sensor of a peritoneal dialysis device, for example device 202. In some embodiments, the drained dialysate content is measured during the draining procedure or in at least two time points during the procedure.

According to some exemplary embodiments, the dialysis efficacy is determined at 804. In some embodiments, the dialysis efficacy is determined based on the drained dialysis content measurement results. In some embodiments, if the levels of creatinine and/or urea in the drained dialysate are below a desired threshold, the dialysis treatment is not efficacious. Alternatively or additionally, if the dextrose concentration in the drained dialysate is above a desired threshold, optionally compared to the concentration in the infused dialysate, then the dialysis treatment has a low efficacy. In some embodiments, if the levels of creatinine and/or urea in the drained dialysate are higher than a desired threshold, then the dialysis treatment is efficacious. Alternatively or additionally, the dialysis treatment is efficacious if the dextrose concentration in the drained dialysate is lower than a desired threshold, optionally compared to the concentration in the infused dialysate.

According to some exemplary embodiments, if the efficacy of the treatment is low, then an indication is delivered at 808. In some embodiments, the indication is delivered to the patient and/or to a caregiver. Alternatively or additionally, the indication is delivered to a physician.

According to some exemplary embodiments, in order to increase the efficacy of the dialysis treatment, the infused dialysate composition is modified, for example by increasing the ionic concentration of the infused dialysate. Optionally, the ionic concentration is increased by using a dialysate with a higher dextrose concentration. In some embodiments, the number of dialysate exchanges per day for patients treated with Continuous Ambulatory Peritoneal Dialysis (CAPD), or per night for patients treated with Automated Peritoneal Dialysis (APD) is increased. In some embodiments, the dialysate volume in each exchange in CAPD is increased. In some embodiments, to increase the efficacy, an additional dialysate exchange during the night is added to a CAPD treatment schedule. In some embodiments, to increase efficacy, an additional dialysate exchange is added during the day to an APD treatment schedule.

According to some exemplary embodiments, in order to increase the efficacy of the dialysis treatment, the dwelling time is increased. In some embodiments, the dwelling time is the time period in which the infused dialysate remains inside the peritoneal cavity until draining. In some embodiments, if the filtration rate through the peritoneal membrane is low, increasing the dwelling time allows to prolong the filtration process, for example to increase the concentration of creatinine or urea in the drained dialysate.

According to some exemplary embodiments, if the efficacy of the treatment is higher than a desired efficacy, then an indication is delivered at 814. In some embodiments, the indication is delivered to the patient and/or to a caregiver. Alternatively or additionally, the indication is delivered to a physician.

According to some exemplary embodiments, in order to reach a desired efficacy, the infused dialysate composition is modified, for example by lowering the ionic concentration of the infused dialysate. In some embodiments, removing access water from the body of an end-stage renal disease (ESRD) patient is done by ultrafiltration. In some embodiments, the high glucose (dextrose) concentration in the dialysate creates osmotic pressure that allows, for example water to go from the blood into the dialysate fluid. Optionally, during this process, the glucose concentration in the dialysate decreases and increases in the blood.

According to some exemplary embodiments, in order to reach a desired efficacy of the dialysis treatment, the dwelling time is lowered. In some embodiments, the dwelling time is the time period in which the infused dialysate remains inside the peritoneal cavity until draining.

According to some exemplary embodiments, if the dialysis efficacy is in a desired range, for example when the concentration of creatinine and/or urea is in a desired range, then an indication is delivered at 806 to a patient and/or a caregiver and/or to a physician.

According to some exemplary embodiments, the changes in the infused dialysate composition and/or in the dwelling time are based on alternative treatment plans stored in a memory of device 202. In some embodiments, the device automatically determines a modification in at least one treatment parameter and/or in the treatment plan to optimize the dialysis treatment. Alternatively, the device suggests modifications of at least one parameter or an alternative treatment plan to the patient and/or to the caregiver.

According to some exemplary embodiments, the peritoneal dialysis efficacy is determined based on the functions of Kt/V, where K is the dialyzer clearance of urea, t is the dialysis time and V is the volume of distribution of urea. Optionally, the volume distribution of urea is equal to the patient's total body water. In some embodiments, the function and/or values or ranges of values of the different function variables are stored in a memory of the device, for example memory 212 in FIG. 2. In some embodiments, the dialysis efficacy is determined, optionally by a controller of the device using a table, or different thresholds of the function variables or a machine learning which is based on the Kt/V function or on the function results.

According to some exemplary embodiments, the dialysis efficacy is determined using software programming and/or device programming and/or device circuitry and/or using neuronal networks. Alternatively or additionally, the dialysis efficacy is determined based on tables and/or functions and/or rules which are optionally stored in the memory of the device.

Exemplary Dialysis Treatment Device Activation Process

Figure 9A:
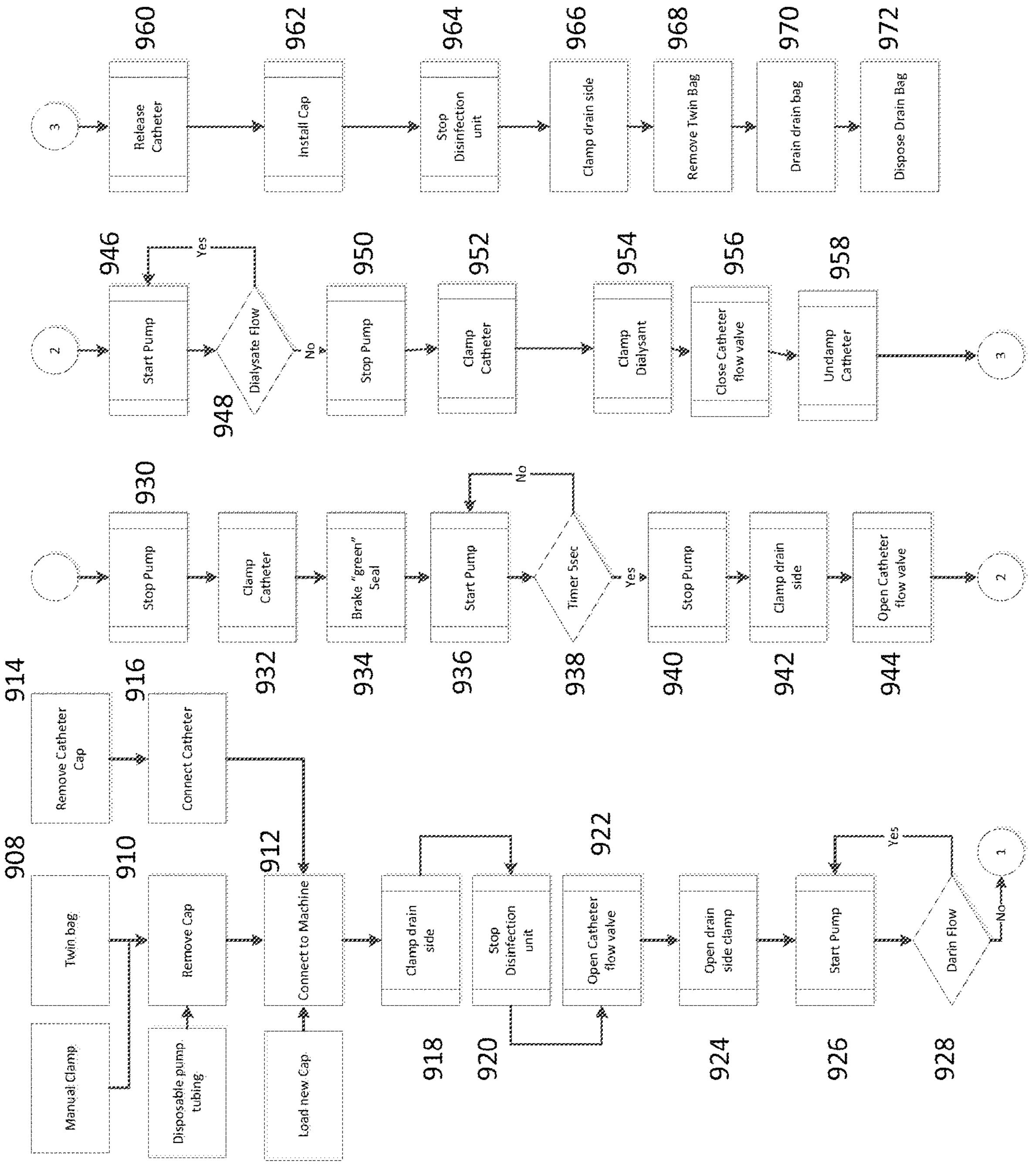
FIGS. 9A and 9B are flow charts of processes for activation of a peritoneal dialysis device, according to some embodiments of the invention.

Reference is now made to FIG. 9A depicting a process for activation of a peritoneal dialysis system, according to some embodiments of the invention.

According to some exemplary embodiments, the cap of a twin bag 908 is removed at 910. In some embodiments, a manual clamp 902 is added to the twin bag, for example to control the flow into and from the twin bag. Optionally, two clamps are added, one for each bag of the twin bags. In some embodiments, a disposable pump tubing 904 is connected to the twin bag. In some embodiments, the twin bags are connected to the device, for example device 202 or device 102. In some embodiments, when the twin bags are connected to the device, a disinfection process initiates, for example to disinfect a flow path between the twin bags and the pump tubing.

According to some exemplary embodiments, a catheter cap is removed at 214, and the catheter, for example a catheter of a patient is connected to the device at 916. In some embodiments, during the connection of the catheter a disinfection process initiates, for example to disinfect a flow path between the catheter and the pump tubing. In some embodiments, the drain side of the twin bags is clamped at 918. In some embodiments, the disinfection unit is stopped at 920. In some embodiments, the catheter flow valve is opened at 922. In some embodiments, the drain side clamp is opened at 924, for example to allow drained dialysate to enter the draining bag.

According to some exemplary embodiments, the pump is activated at 926. In some embodiments, the pump, for example a peristaltic pump rotates a rotor in a direction towards the draining bag. In some embodiments, if drained dialysate flows into the draining bag then the pump remains activated. In some embodiments, if the drained dialysate does not flow, then the pump is stopped at 930.

According to some exemplary embodiments, the catheter is clamped at 932. In some embodiments, a seal brakes at 934. In some embodiments, the seal brakes for example, to allow washing of the drained dialysate from the pump tubing. In some embodiments, the pump is activated at 936. In some embodiments, the pump is activated for a desired time period to wash the pump tubing. In some embodiments, when the desired time period is over, the pump is stopped at 940. In some embodiments, the drain side is clamped at 942. In some embodiments, the catheter flow valve is opened at 944, for example to allow a flow path between the fresh dialysate bag and the catheter.

According to some exemplary embodiments, the pump is activated at 946. In some embodiments, the pump remains activated as long as dialysate flows into the catheter. In some embodiments, if dialysate does not flow, then the pump is stopped at 950. In some embodiments, the catheter is clamped at 952, for example to isolate the catheter from the pump tubing. In some embodiments, the dialysate is clamped at 954. In some embodiments, the catheter flow valve is closed at 956, for example to prevent any flow into and out from the catheter.

According to some exemplary embodiments, the catheter is unclamped at 958. In some embodiments, the catheter is released or disconnected at 960. In some embodiments, a cap is installed on the catheter opening at 962. In some embodiments, the disinfection unit is stopped at 964.

According to some exemplary embodiments, the drain side is clamped at 966. In some embodiments, the twin bag is removed at 968. In some embodiments, the drain bag is drained at 970. In some embodiments, the drain bag is disposed at 972.

According to some exemplary embodiments, the disposable pump tubing 904 is also disconnected from the device. In some embodiments, new disposable pump tubing is added to the device between an infusion process and a draining process.

Figure 9B:
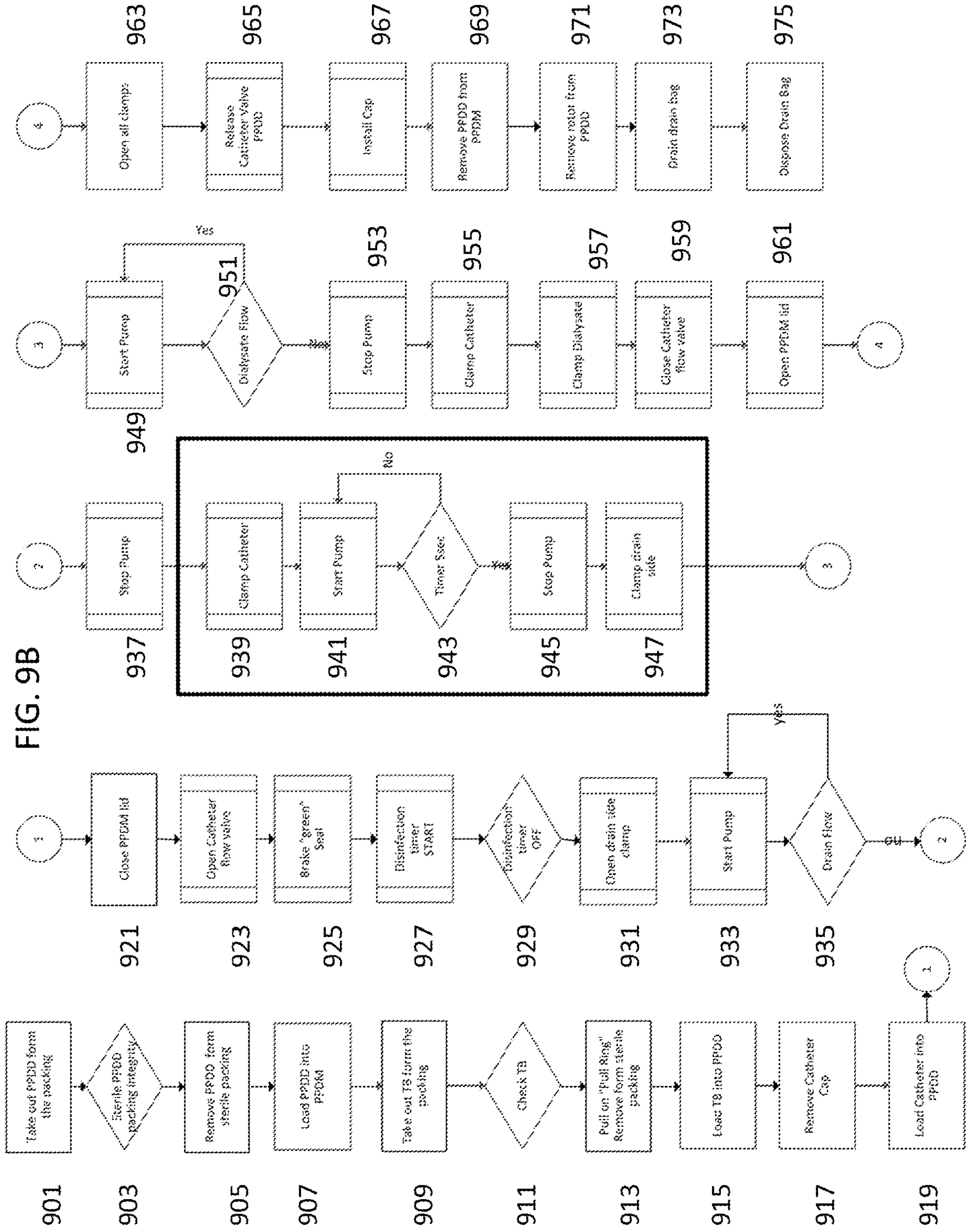

Reference is now made to FIG. 9B, depicting an activation process of a peritoneal dialysis system, according to some embodiments of the invention.

According to some exemplary embodiments, a portable peritoneal dialysis disposables (PPDD) is taken out from a packing at 901. In some embodiments, the sterility of the PPDD packing is examined and/or determined at 903. In some embodiments, the sterility of the packing is determined by examining the integrity of the packing at 903. In some embodiments, if the packing is sterile the PPDD is removed from the packing at 905.

According to some exemplary embodiments, the PPDD is loaded into a portable peritoneal dialysis machine (PPDM) at 907. In some embodiments, the PPDM is a durable part of the device, and the PPDD is the disposable part of the device. In some embodiments, the tubing is taken out from the packing, optionally a disposable packing, at 909. In some embodiments, the tubing is examined at 911. In some embodiments, a "pull ring" is removed from the sterile packing at 913. In some embodiments, the tubing is loaded into the PPDD. Optionally, the tubing is placed in association with a pump rotor of the PPDD.

According to some exemplary embodiments, the tubing is loaded into the PPDD at 915. In some embodiments, the catheter cap, for example a patient catheter cap is removed at 917. In some embodiments, the catheter is loaded into the PPDD at 919. Optionally, during the loading of the catheter, the catheter is disinfected by a disinfecting connector of the PPDD.

According to some exemplary embodiments, the lid of the PPDM is closed at 921. Optionally, closing the lid initiates a disinfection process of the catheter. In some embodiments, the catheter flow valve is opened at 923. In some embodiments, a seal, for example a "green" seal is broken at 925. Optionally, braking of the seal releases disinfecting solution into the catheter.

According to some exemplary embodiments, a disinfection timer is initiated at 927. In some embodiments, the disinfection timer is stopped 929. In some embodiments, the disinfection timer sets a desired time period sufficient for disinfecting a flow path between the tubing and the catheter. In some embodiments, a drain side clamp is opened at 931. In some embodiments, the pump is activated at 933, for example to drain dialysate from the peritoneal cavity. In some embodiments, if fluid is drained at 935 then the pump remains activated. In some embodiments, if there is no fluid to drain, the pump is stopped at 937.

According to some exemplary embodiments, the catheter is clamped at 939. In some embodiments, the pump is activated at 941, for example to clear the residual drained dialysate from the tubing. In some embodiments, the pump is activated, optionally by a timer, for at least 2 seconds, for example 2, 3, 4, 5, 6, 7 seconds or and intermediate or longer time period at 943. Alternatively, the pump is activated until there is no residual fluid in the tubing. In some embodiments, the pump is stopped at 945. In some embodiments, the drain side is clamped at 947.

According to some exemplary embodiments, the catheter clamp is released. In some embodiments, the dialysate clamp is released. In some embodiments, the pump is activated at 949, for example to allow infusion of dialysate into the catheter. In some embodiments, dialysate flows into the catheter at 951. In some embodiments, the pump remains activated as long dialysate flows into the catheter. In some embodiments, the pump is stopped 953 when dialysate does not flow into the catheter. Optionally, the pump is stopped following an activation parameter of the treatment protocol. In some embodiments, the catheter is clamped at 955. In some embodiments, the dialysate is clamped at 957. In some embodiments, the catheter flow valve is closed at 959.

According to some exemplary embodiments, the PPDM lid is opened at 961. In some embodiments, all clamps are opened at 963. In some embodiments, the catheter is released from the PPDD at 965. In some embodiments, a cap is installed on the catheter opening.

According to some exemplary embodiments, the PPDD is removed from the PPDM at 969. In some embodiments, the rotor is removed from the PPDD at 971. In some embodiments, the drain bag is drained at 973. In some embodiments, the drain bag is disposed at 975. Optionally, the PPDD or just the tubing is disposed at 975.

Exemplary Device Interactions and Functions

Figure 10:
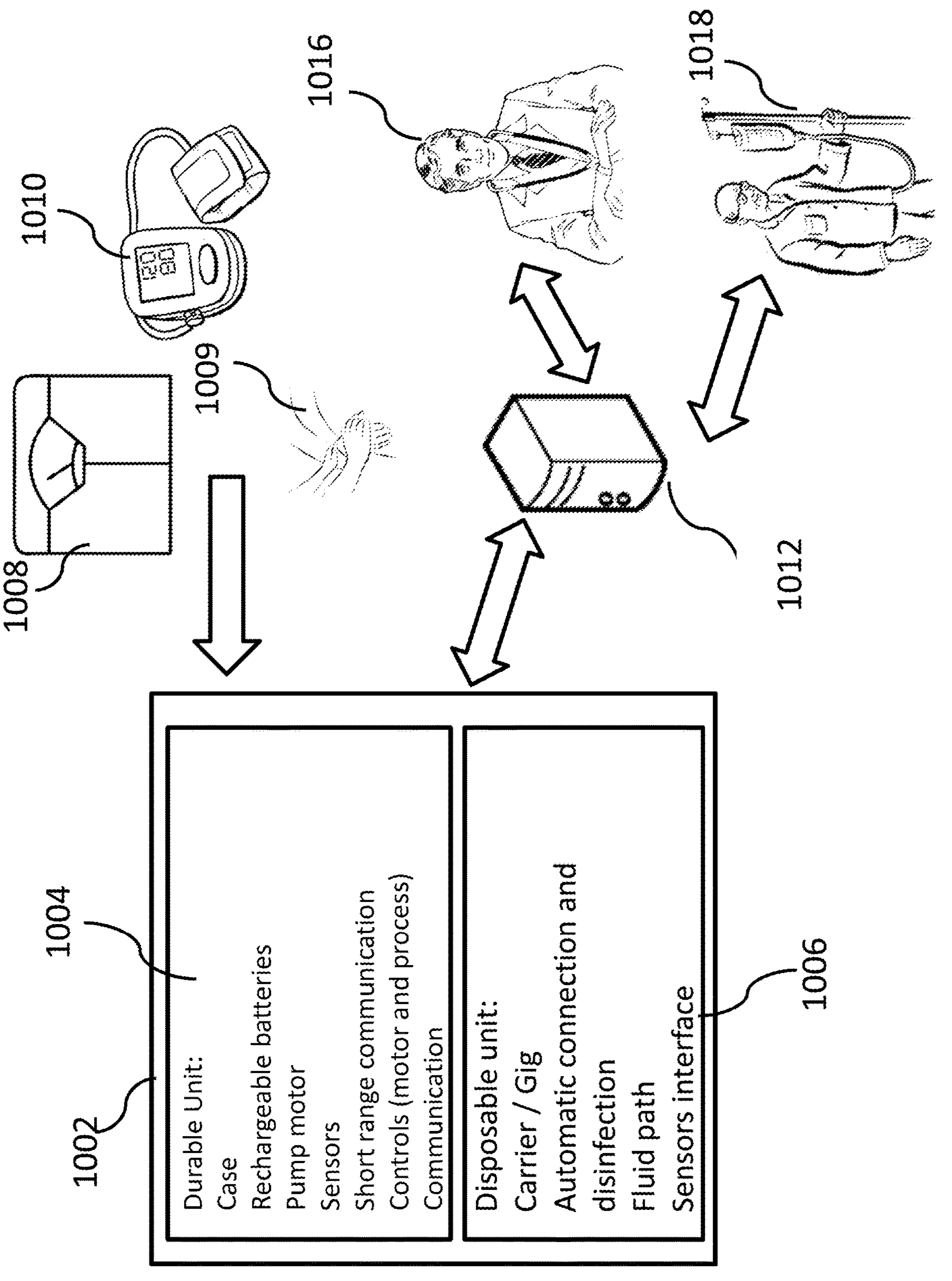
FIG. 10 is a schematic illustration of a peritoneal dialysis device interactions, according to some embodiments of the invention.

Reference is now made to FIG. 10 depicting a peritoneal dialysis device interactions and functions, according to some embodiments of the invention.

According to some exemplary embodiments, a peritoneal dialysis system 1002 comprises a PPDM unit, for example durable unit 1004 and a PPDD disposable unit 1006. In some embodiments, the durable unit 1004 comprises a case, a power unit for example a battery, a pump motor, for example an electrical pump motor, and a motor interface. In some embodiments, the durable unit further comprises at least one sensor, a communication module and a controller, for example to control the dialysis treatment process and motor.

According to some exemplary embodiments, the disposable unit 1006 comprises a carrier, a connection module, optionally an automatic connection module. In some embodiments the connection module is also a disinfection module. Additionally, the disposable unit 1006 comprises a pump rotor, which is shaped and sized to fit the motor interface of the durable unit 1004. In some embodiments, the disposable unit 1006 comprises at least one sensor, for example a clinical sensor for measuring clinical parameters of the treatment and/or clinical parameters of the patient connected to the device 1002.

According to some exemplary embodiments, the device 1002 measures clinical parameters of the patient, for example body weight 1008, blood pressure 1010 and/or heart rate 1009. In some embodiments, the device 1002 writes the measured parameter values and other information on a memory of the device or in a remote memory 1012. In some embodiments, the device 1002 reads from remote memory 1012 treatment plans and treatment parameters. Additionally, the device transmits the stored information to a physician 1016 and/or to the patient 1018. In some embodiments, the physician 1016 transmits information, for example suggested treatment protocol or suggested protocol modifications to the remote memory 1012 or directly to a memory of the device 1002.

Exemplary System

Figure 11:
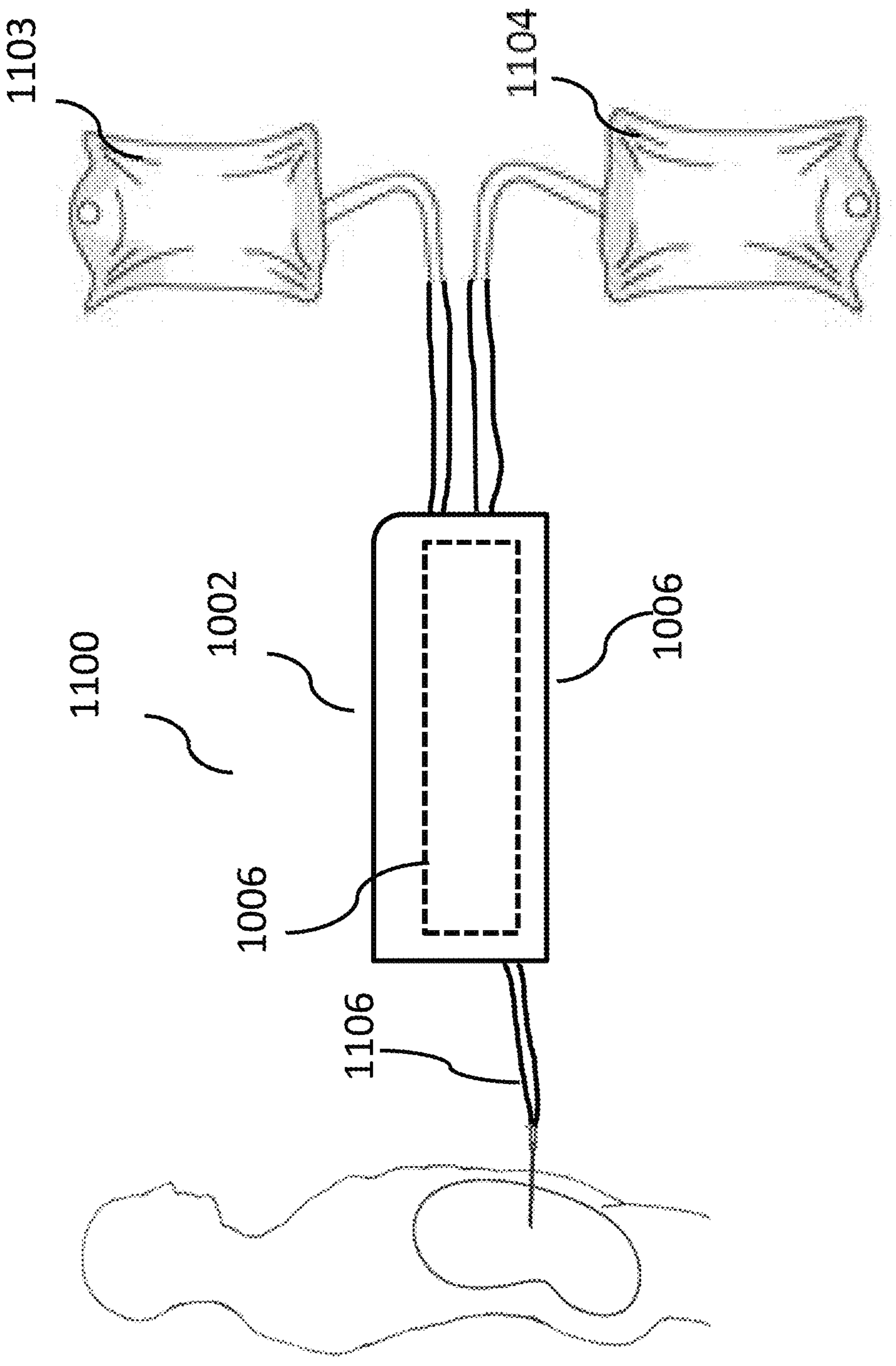
FIG. 11 is a schematic illustration of a system for delivery of a peritoneal dialysis treatment, according to some embodiments of the invention.

Reference is made to FIG. 11, depicting a system for delivery of a peritoneal dialysis treatment, according to some embodiments of the invention.

According to some exemplary embodiments, a Portable Peritoneal Dialysis System (PPDS), for example system 1100 comprises at least one bag, for example a dialysate bag 1103 and a drained dialysate bag 1104, connected to a connector of device 1102. In some embodiments, a patient catheter tube 1106 a different is connected to a different connector of device 1102.

Figure 12:
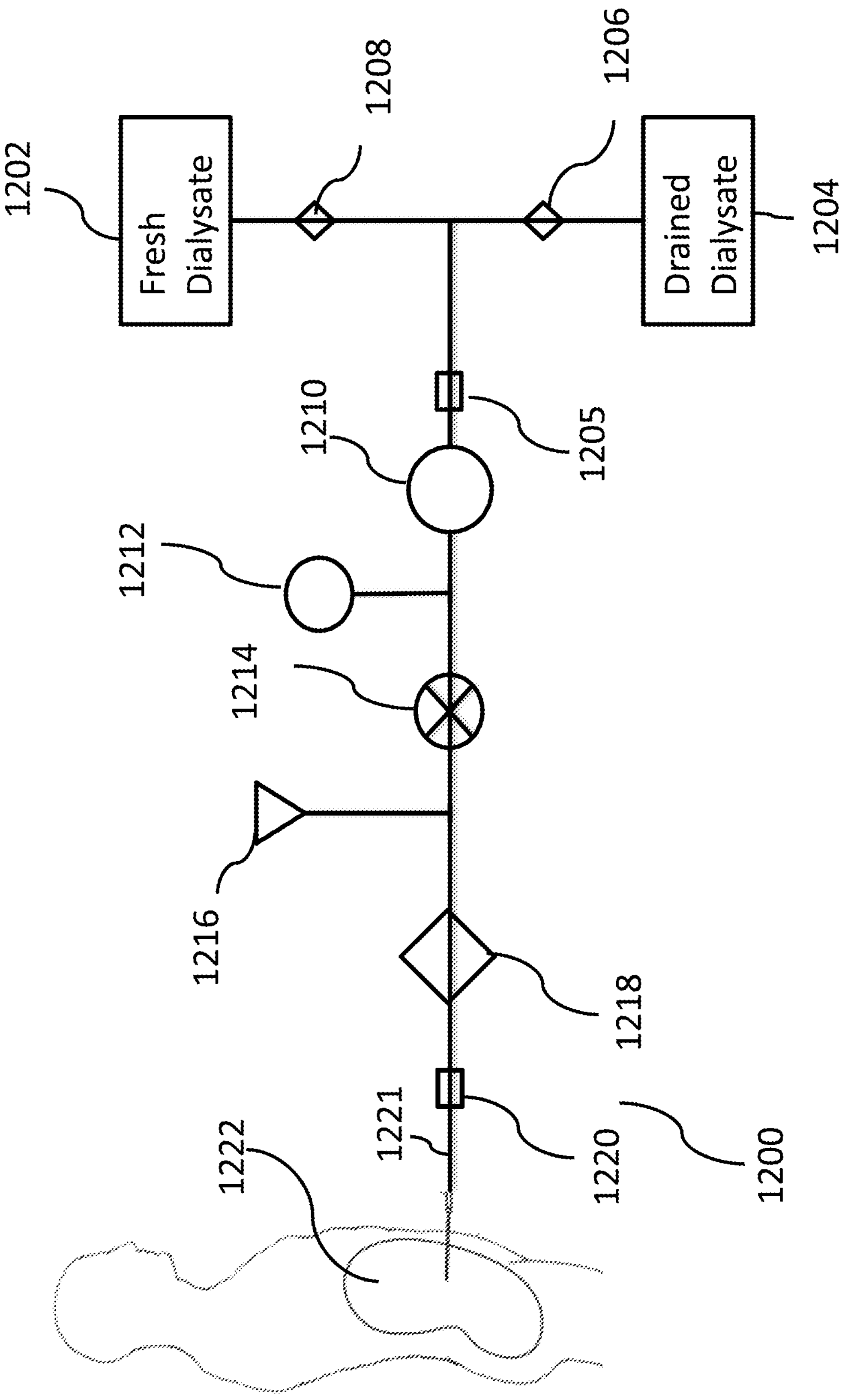
FIG. 12 is a schematic illustration of a system for monitoring and/or controlling a peritoneal dialysis treatment, according to some embodiments of the invention.

Reference is made to FIG. 12 depicting a system for monitoring and/or controlling a peritoneal dialysis treatment, according to some embodiments of the invention.

According to some exemplary embodiments, a new dialysate solution storage compartment 1202 is connected via a flow breaker 1208 to a connector 1205, for example a y-connector. In some embodiments, a used dialysate storage compartment is connected via a flow breaker 1206 to the connector 1205. In some embodiments, flow breakers 208 and 1205 are used to close the flow path between the storage compartments and the connector 1205. In some embodiments, the connector 1205 automatically disinfects the flow path towards each of the compartments.

According to some exemplary embodiments, the connector 1205 is positioned in the distal end of pump tubing, which is associated with a rotor of a peristaltic pump 1210. In some embodiments, at least one pressure sensor, for example pressure sensor 1212 senses the pressure of the fluid within the pump tubing. In some embodiments, at least one flow sensor, for example flow sensor 1214 senses the flow speed and/or the fluid volume within the pump tubing. In some embodiments, at least one peritonitis sensor, for example peritonitis sensor 1216 senses the formation of peritonitis within the peritoneal cavity, as previously described. In some embodiments, the fluid within the pump tubing passes through a heating unit 1218. In some embodiments, heating unit 1218 heats the fresh dialysate fluid within the pump tubing to a desired temperature, before it is infused into the patient's catheter.

According to some exemplary embodiments, a patient catheter 1221 connects the peritoneal cavity 1222 of a patient with a connector 1120. In some embodiments, the connector 1120 is connected to the proximal end of the pump tubing. In some embodiments, the connector 1120 automatically or semi-automatically connects the patient catheter to the proximal end of the pump tubing. Additionally or optionally, the connector 1120 automatically or semi-automatically disinfects a flow path between the patient's catheter and the pump tubing.

Exemplary Dialysate Testing Module

Reference is now made to FIGS. 13A-13G, depicting dialysate testing means, according to some embodiments of the invention.

According to some exemplary embodiments, a PPDD unit, for example a disposable unit 1301 comprises a pump tubing and at least one connector, for example a disinfecting connector at the tubing end. In some embodiments, pump tubing 1302 is associated with rotor 1308 and comprises at least one connector, for example connectors 1304 and 1314 at the two ends of the tubing 1302. In some embodiments, a flow regulator, for example a clamp is positioned on the tubing 1302 next to the connector, for example flow regulators 1306 and 1312. In some embodiments, when the flow regulators are closed fluid does not flow into and out from the pump tubing. In some embodiments fluid can flow into and out from the pump tubing only when the flow regulators are at least partly open. In some embodiments, the at least one flow regulator allows for example, to control the flow of fresh dialysate into the patient's catheter and/or from the patient's catheter into the draining bag.

According to some exemplary embodiments, at least one testing path, for example tubes 1310 and tube 1309 are fluidically connected to the pump tubing, for example to allow fluid flow from the pump tubing 1302 into at least one of the tubes 1310 or into tube 1309. In some embodiments, some of the testing paths are used for testing the drain dialysate, and some of the testing paths, for example tube 1309 is used for testing the fresh dialysate. In some embodiments, the flow into one of the testing paths is controlled by a valve or a flow regulator. Optionally, the valve or the flow regulator is automatically or semi-automatically controlled by the peritoneal dialysis device, for example device 202.

Figure 13A:
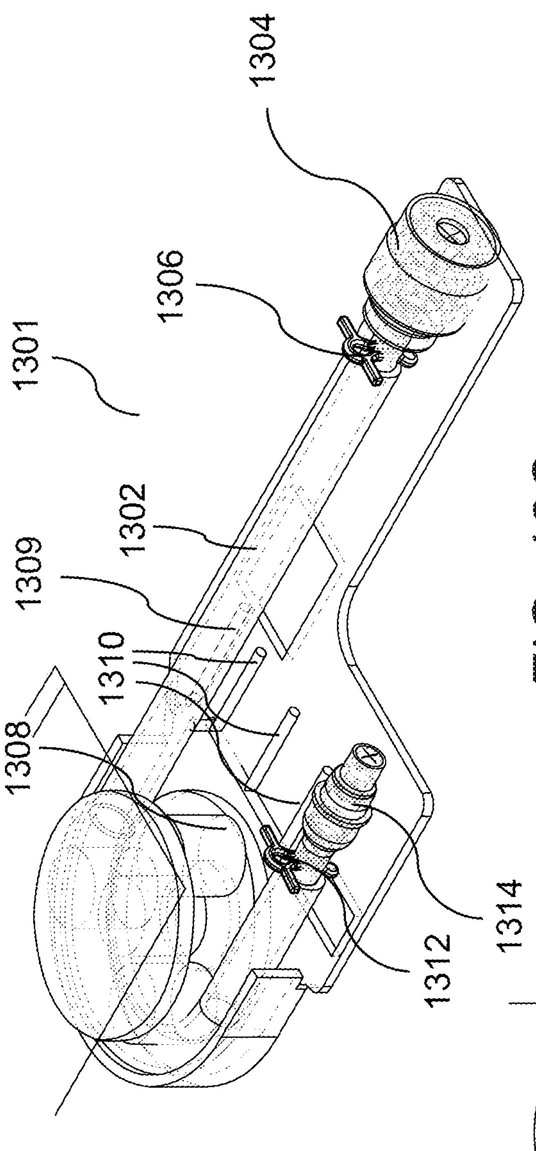
FIGS. 13A-13G are schematic illustrations of a peritoneal dialysis device and system with dialysate testing means, according to some embodiments of the invention.
Figure 13B:
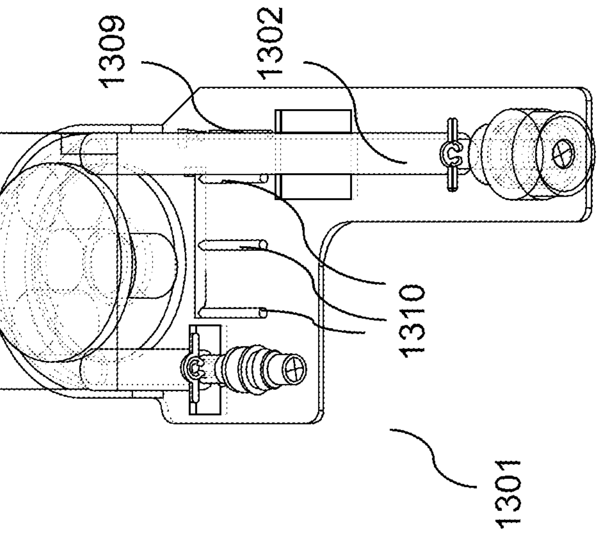
Figure 13C:
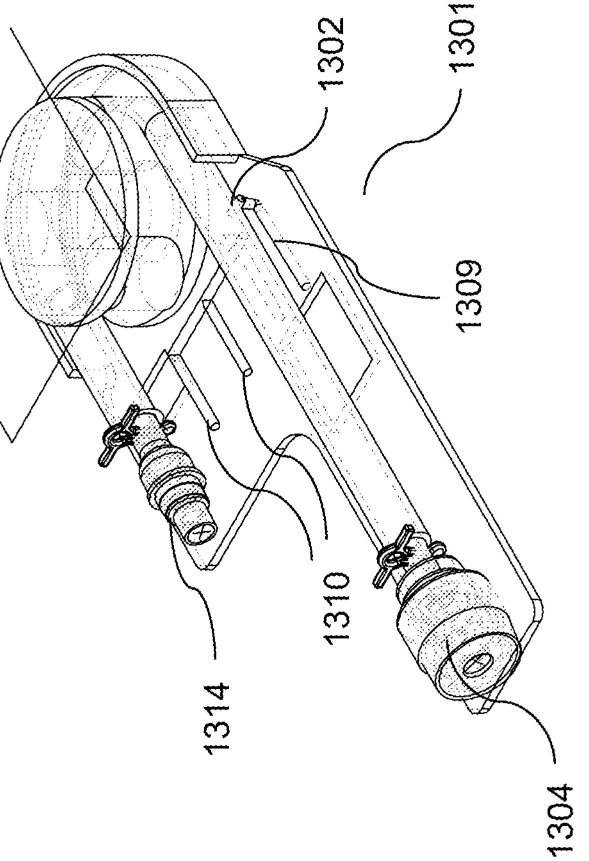
Figure 13D:
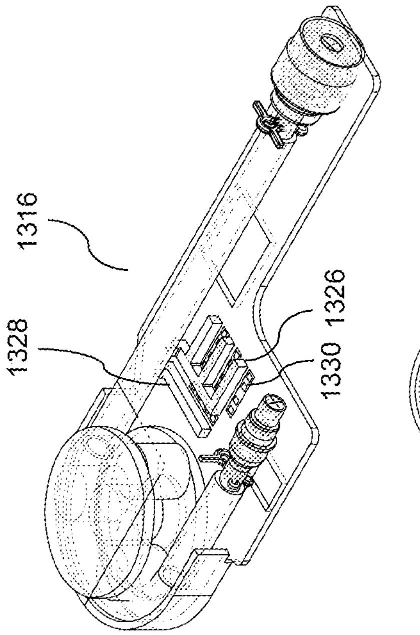
Figure 13E:
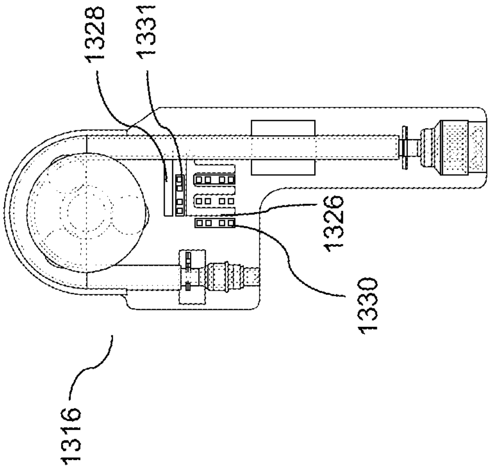

According to some exemplary embodiments, for example as shown in FIGS. 13D and 13E, each of the testing paths, for example tubes 1326 and 1328 of disposable unit 1316 comprise a scale, for example scales 1330 and 1331. In some embodiments, the scales, for example color scales are used to visually estimate the levels of chemicals and/or biological elements in the fluid using a colorimetric reaction. In some embodiments, the color scale comprises colors or indications of colors of dialysate colors.

Figure 13F:
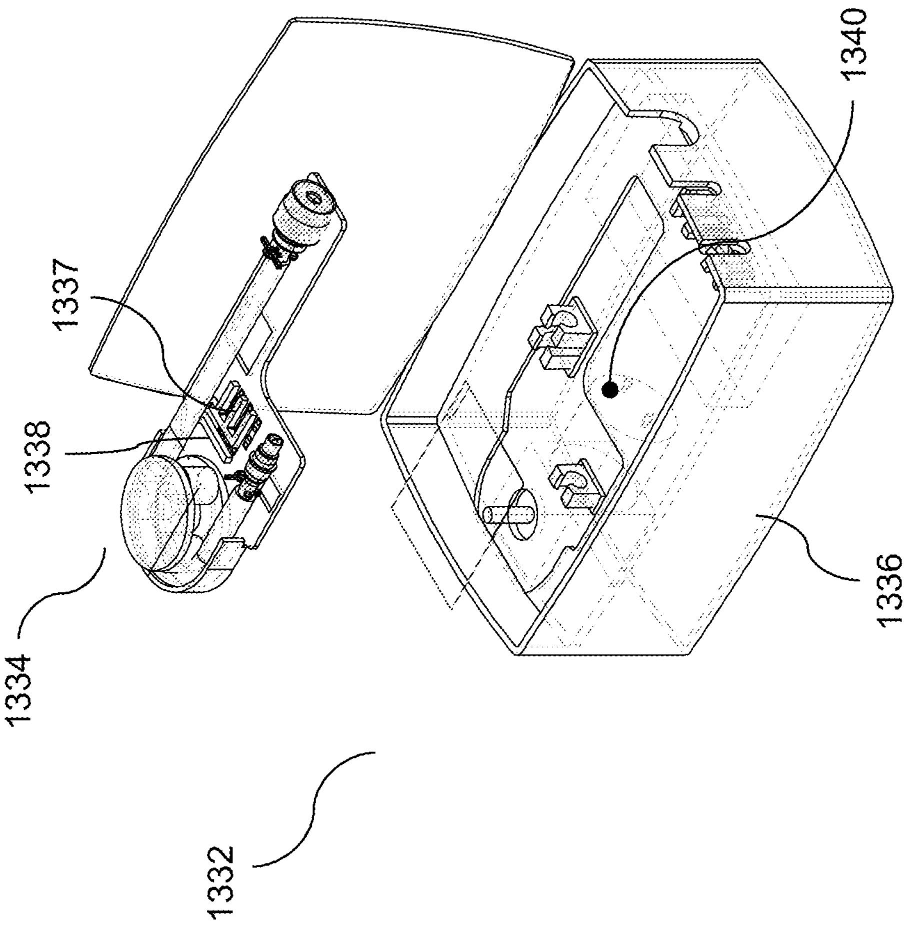
Figure 13G:
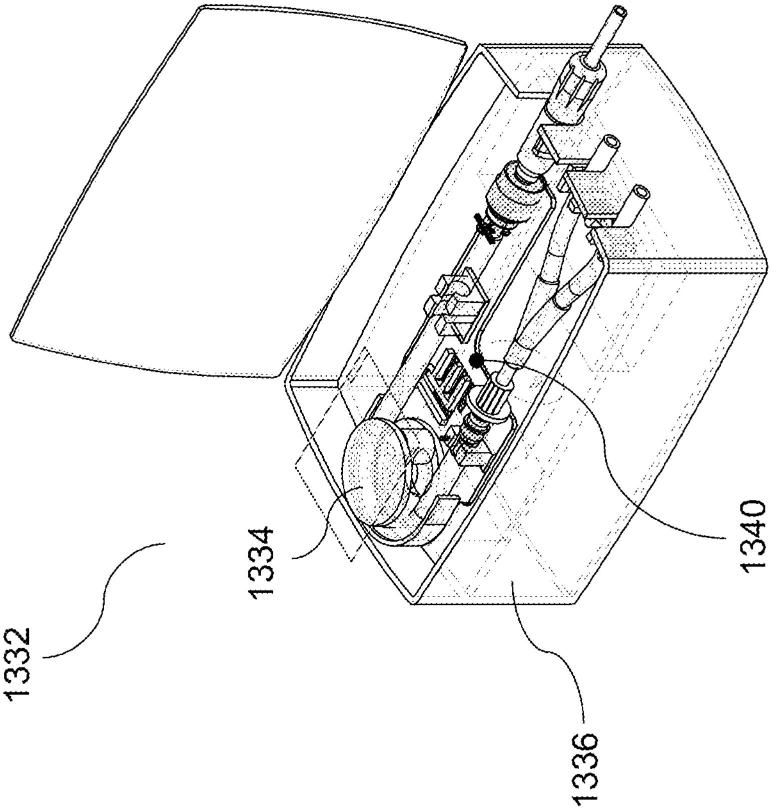
Figure 13H:
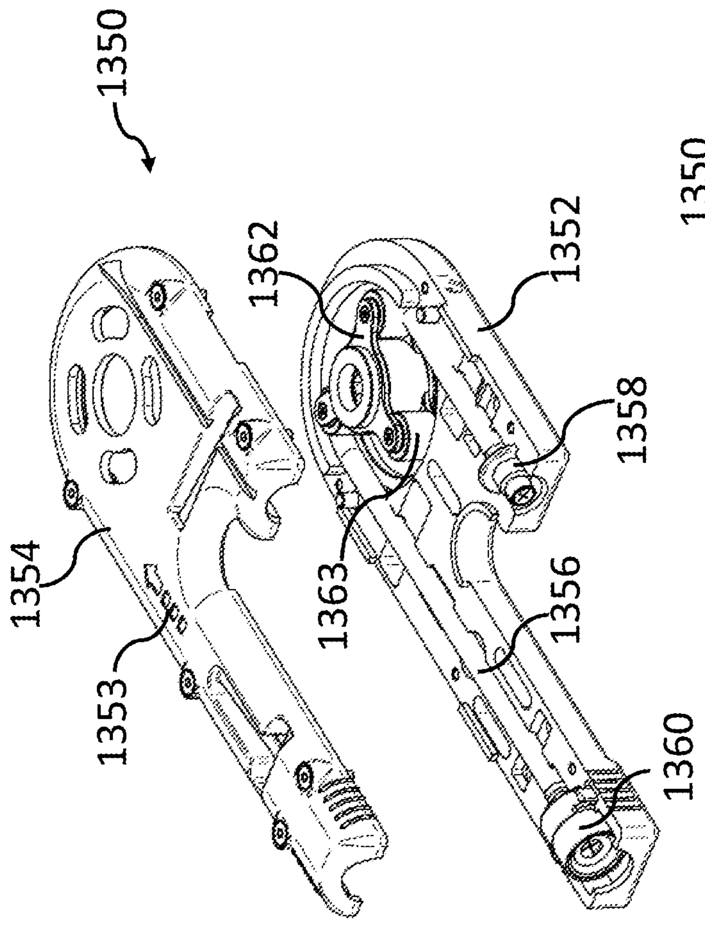
FIGS. 13H-13L are schematic representations of a disposable unit, according to some embodiments of the invention.

According to some exemplary embodiments, for example as shown in FIGS. 13F and 13G, the fluid content within the testing paths are analyzed by at least one sensor. In some embodiments, a PPDD unit, for example disposable unit 1334 of device 1332 includes at least one testing path, for example tubes 1337 and 1338. In some embodiments, the disposable unit 1334 is placed inside a PPDM unit for example, durable unit 1336. In some embodiments, durable unit 1336 comprises at least one sensor positioned such that when the disposable unit 1334 is positioned inside the durable unit 1336, sensor 1340 is proximal, and optionally aligned with at least one testing path. In some embodiments, the sensor 1340 measures the absorbance of light optionally in specific wave lengths. In some embodiments, the sensor 1340 is a spectrophotometer. In some embodiments, the at least one sensor 1340 measures absorption and/or scattering of light passing through the testing path in a wavelength range of 500-650 nm, for example in a range of 500-600 nm, in a range of 550-620 nm, in a range 530-630 nm or any intermediate, smaller or larger wavelength range. Additionally or alternatively, sensor 1340 or at least one additional sensor measures absorption and/or scattering of light passing through the testing path in a wavelength range of 150-350 nm, for example 150-250 nm, 200-300 nm, 250-350 nm or any intermediate smaller or larger range of wavelengths.

According to some exemplary embodiments, at least one sensor or a testing element is connected to the testing paths, for example to measure chemical and/or biological properties of the fluid the flows in the pump tubing.

Exemplary Disposable Unit of a Portable Peritoneal Dialysis Device

According to some exemplary embodiments, a portable peritoneal dialysis system (PPDS) comprises a portable peritoneal dialysis machine (PPDM) for example a durable unit, and a portable peritoneal dialysis disposable (PPDS), for example a disposable unit. Optionally the PPDS comprises a portable peritoneal patient management (PPPM) system. In some embodiments, the durable unit comprises a motor, optionally an electric motor and electrical wiring. In some embodiments, the disposable unit comprises a tube with at least one connector. In some embodiments, the disposable unit is shaped and sized as a single unit keeping at least most of the disposable elements, for example a tube and at least one connector encased in a separate housing from the durable unit. In some embodiments, the separate housing allows for example, easy assembly between the disposable unit and the durable unit, while protecting the disposable elements of the system. Additionally, the separate housing allows selling the disposable unit as a ready to use product without the need of further assembly of disposable element by the user.

Reference is now made to FIGS. 13H-13M depicting a disposable unit of a PPDS comprising a separate housing, according to some exemplary embodiments of the invention.

According to some exemplary embodiments, a disposable unit of a PPDS device, for example disposable unit 1350 comprises a tube 1356 and at least one connector, for example Y-set connector 1358 and catheter connector 1360 located at the two ends of the tube 1356. Optionally, at least one of the connectors is a self-sterilizing connector, for example when connecting to an external connector sterilizing material interacts with the interface between the two connectors. Additionally, the disposable unit 1350 comprises a rotor 1362 having at least one cylindrical contacting member, for example cylindrical contacting member 1363 placed at a distal end of the wings of the rotor. In some embodiments, the at least one cylindrical contacting member, optionally a rollable cylindrical contact member, is in direct contact with at least part of the tube 1356. In some embodiments, the disposable elements are placed within shaped grooves or indentations made in the internal surface of the disposable unit housing, for example a two-part housing. In some embodiments, the grooves or indentations are made in the internal surface of at least one part of the two-part housing, for example in a base portion 1352. In some embodiments, the two-part housing comprises a complimentary cover portion 1354, shaped and sized to match the base portion 1352. In some embodiments, the cover portion 1354 comprises grooves or indentations that match at least part of the three dimensional shape or external contour of the disposable elements within the base portion 1352.

Figure 13I:
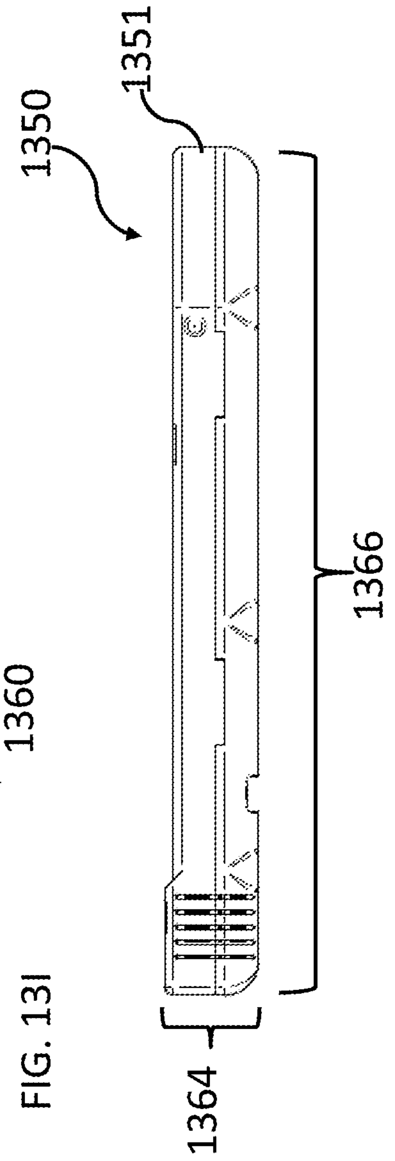

According to some exemplary embodiments, for example as shown in FIG. 13I the base portion 1352 and the cover portion are assembled into housing 1352 of the disposable unit 1350. In some embodiments, the axial length 1366 of the housing 1352 is at least 10 cm, for example 12 cm, 15 cm, 19 cm, 20 cm, 25 cm or any intermediate, smaller or larger value. In some embodiments, the width 1364 of the housing 1351 is at least 1 cm, for example 1.5 cm, 2 cm, 2.5 cm or any intermediate, smaller or larger value.

Figure 13J:
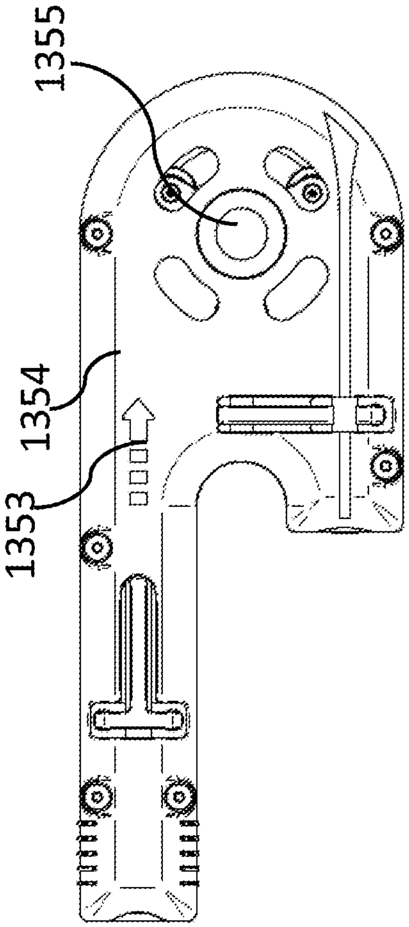

According to some exemplary embodiments, the housing is shaped to allow easy assembly into the durable unit and/or easy assembly of external tubes to at least one connector of the disposable unit. In some embodiments, for example as shown in FIG. 13J the outer surface of cover portion 1354 comprises at least one marking, for indicating an assembly direction of an external tube to a connector of the disposable unit, and or an assembly direction of the disposable unit into the durable unit, for example to reduce assembly errors due to improper alignment. In some embodiments, the at least one marking 1353 indicates for example a cover portion. In some embodiments, cover portion 1354 comprises an opening above the rotor, for example opening 1355. In some embodiments, the opening 1355 allows, for example to visualize the rotation direction of the rotor.

Figure 13K:
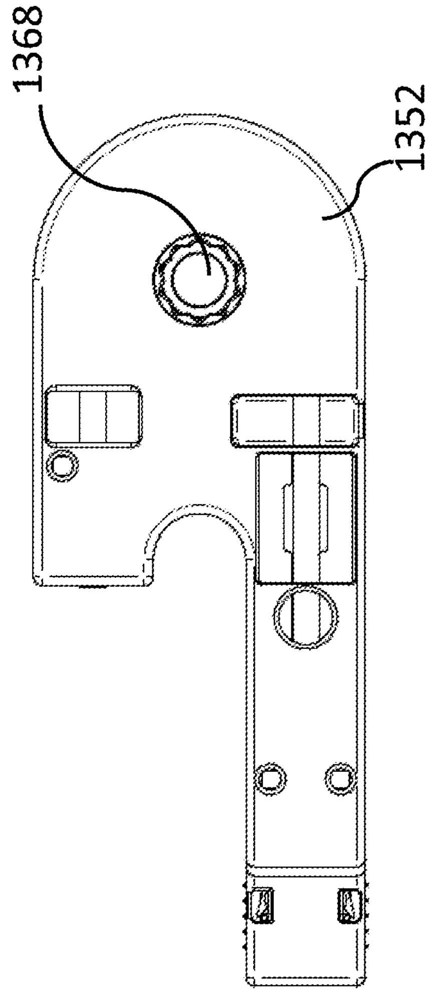

According to some exemplary embodiments, for example as shown in FIG. 13K, the base portion 1352 comprises an opening 1368 shaped and sized to allow the passing of a motor shaft of the durable unit through the opening 1368. In some embodiments, the motor shaft passes through the opening 1368 and is connected to the rotor, optionally a disposable rotor within the disposable unit housing.

Figure 13L:
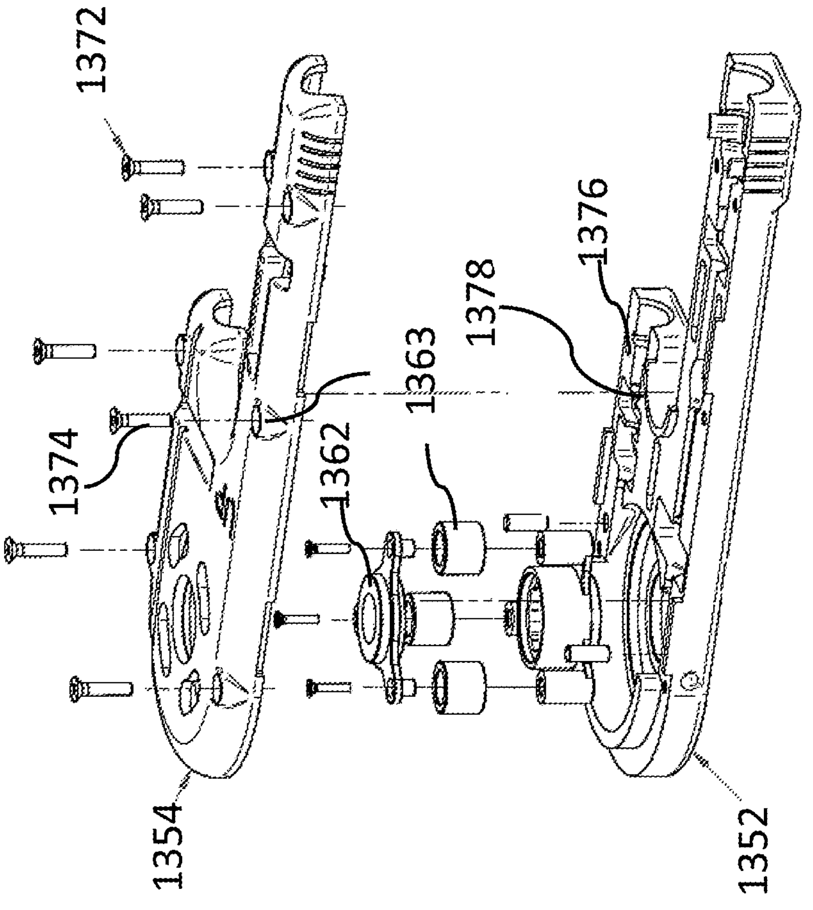

According to some exemplary embodiments, for example as shown in FIG. 13L, the cover portion 1354 of the housing is mechanically connected to the base portion 1352 of the housing via at least two connecting members 1372 and 1374, for example at least two threaded fasteners or screws. In some embodiments, the threaded fasteners comprise screws and/or bolts. In some embodiments, the two connecting members comprise pins. In some embodiments, each of the at least two connecting members penetrates through an opening in the cover portion, for example opening 1365 and into an opening in the base portion, for example base portion opening 1376. Optionally, the base portion opening comprises an internal threading complementary to an external threading on the connecting member.

According to some exemplary embodiments, for example as shown in FIG. 13L, each of the rotor 1362 wings, for example wing 1361 is connected to a cylindrical contacting member, for example cylindrical contacting member 1363 by a pin, a thread or a bolt, shaped and sized to pass through an opening in the rotor wing and an opening in the cylindrical contacting member 1363.

Figure 13M:
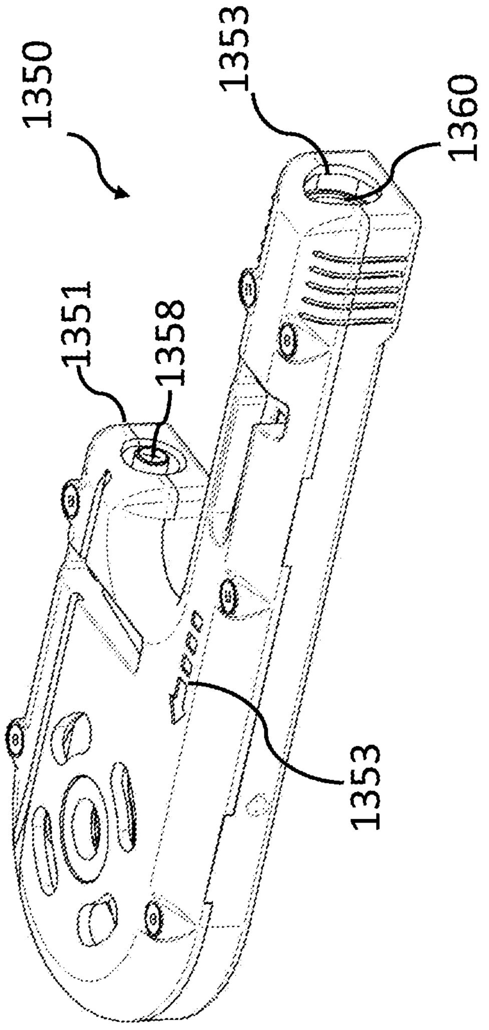
FIG. 13M is a schematic illustration of an assembled disposable unit, according to some embodiments of the invention.

According to some exemplary embodiments, for example as shown in FIG. 13M the assembled disposable unit 1350 has at least two openings in the housing, openings 1351 and 1352. In some embodiments, one opening 1353 is shaped and sized for connection of a catheter to catheter connector 1360 and optionally a second opening 1351 for connecting a Y-set connector 1358. In some embodiments, at least one marking on the external surface of the housing indicates, for example an assembly direction and/or orientation of the disposable unit into a durable unit.

Exemplary Assembly of a Disposable Unit and a Durable Unit

Figure 13O:
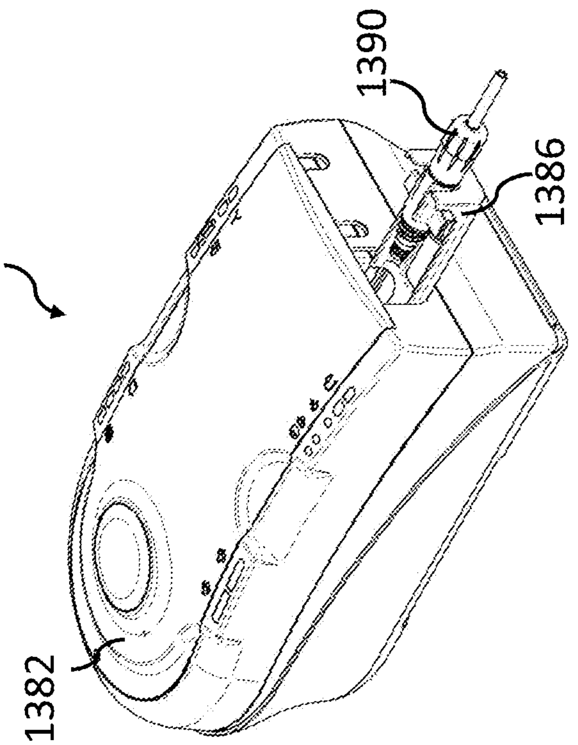
FIGS. 13N-13P are schematic illustrations of an assembled dialysis system, according to some embodiments of the invention.
Figure 13N:
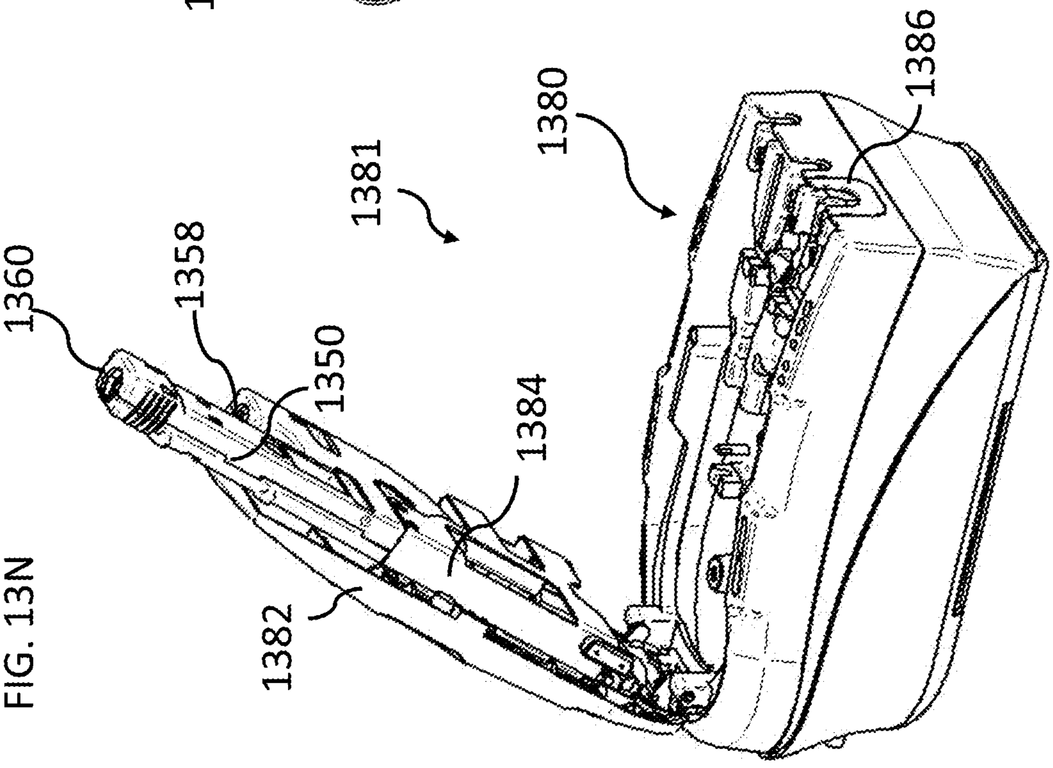
Figure 13P:
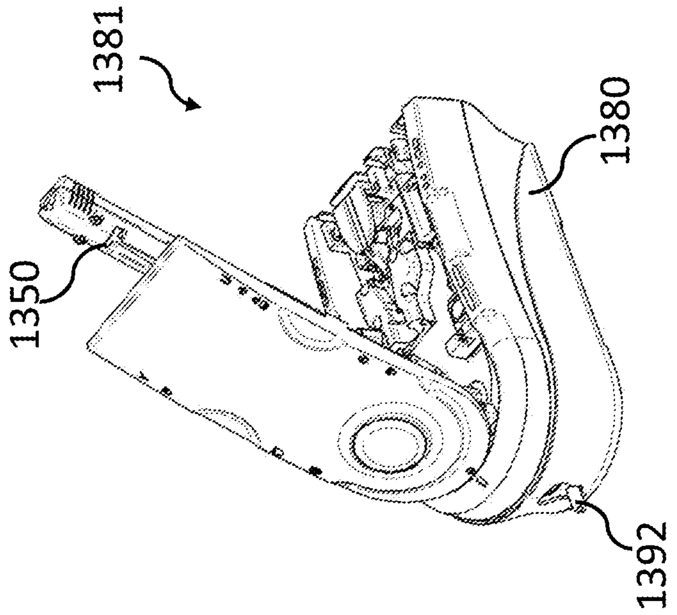

Reference is now made to FIGS. 13N-13P, depicting the assembly of a disposable unit into a durable unit, according to some exemplary embodiments of the invention.

According to some exemplary embodiments, the durable unit, for example durable unit 1380 comprises a door 1382 with optionally an inner aligner, for example aligning slot 1384 optionally attached to the internal surface of the door 1382. In some embodiments, at least part of the door 1382 is transparent, for example to allow visualization of a disposable unit, or a rotor of a disposable unit placed inside the durable unit. In some embodiments, a disposable unit, for example disposable unit 1350 is shaped and sized to inserted into the aligning slot 1384, for example as shown in FIG. 13N. In some embodiments, the disposable unit 1350 is inserted into the aligning slot in a direction and/or orientation indicated by at least one mark on the housing of the disposable unit 1350, for example mark 1353 shown in FIG. 13J.

According to some exemplary embodiments, after the insertion of the disposable unit 1350 into the aligning slot 1384, the door 1382 is closed. In some embodiments, an external connector is connected to Y-set connector 1358 through opening 1351 prior to the closure of the door 1382 or prior to the insertion of the disposable unit 1350 into the aligning slot 1384.

According to some exemplary embodiments, for example as shown in FIG. 13O, when the door 1382 is closed, a drawer of the durable unit 1380, for example drawer 1386 is extended out from the durable unit housing. Optionally, the drawer 1386 is extended automatically when the door 1382 is closed. In some embodiments, the drawer 1386 comprises an upper opening and a side opening 1385, optionally a U-shaped side opening, for placing a catheter end 1390.

According to some exemplary embodiments, when the drawer 1386 is closed, the catheter end 1390 is pushed into the catheter connector 1360. In some embodiments, when the catheter is connected through the catheter connector 1360, a disinfection process is initiated, optionally automatically by the dialysis device 1381.

According to some exemplary embodiments, the dialysis device 1381 activates a motor, for example an electric motor to move disinfecting material through the tubing of the disposable unit and dialysate into and out from the peritoneum of a patient through a catheter connected to the system. In some embodiments, the dialysis device comprises at least one battery, optionally a rechargeable battery. In some embodiments, for example as shown in FIG. 13P, the dialysis device 1381 comprises a charging plug 1392, for connecting an external power source to the rechargeable battery, for example to allow charging of the battery. Alternatively, the connection of the external power source to the dialysis device, allows to activate the device using the external power source instead or in addition to the battery.

According to some exemplary embodiments, the housing of the dialysis device 1381, comprises at least one adapter for example for connecting a belt or a harness to the dialysis device. In some embodiments, the belt or the harness is used to secure the dialysis device to a body part of a patient, for example to the hand, leg, shoulder, thigh and/or hips of the patient.

According to some exemplary embodiments, the dialysis device, for example dialysis device 1381, dialysis device 102 shown in FIG. 1 or dialysis device 202 shown in shown in FIG. 2 is portable and is configured to be secured to a body part of the patient by a belt, a harness or any adaptor. In some embodiments, the dialysis device comprises a durable unit which comprises a motor, for example an electric motor and a battery, optionally a rechargeable battery electrically connected to the rotor. In some embodiments, the durable unit comprises a control circuitry electrically connected to the motor and to the battery. In some embodiments, the control unit controls the activation of the motor according to the power level in the battery. In some embodiments, the durable unit comprises an interface connected to the control circuitry, configured to provide at least one human detectable indication, for example an alert signal by a light indication and/or a sound indication. In some embodiments, when the power level in the battery is lower than a predetermined value, then the control circuitry signals the interface to generate an alert signal, for example a signal indicating to charge the battery or to replace the battery. Alternatively or additionally, when the power level in the battery is lower than a predetermined value, the control circuitry stops the operation of the motor.

According to some embodiments, the control circuitry activates the motor in a power saving mode, for example when the power level in the battery is lower than a predetermined value. In some embodiments, the control circuitry modifies at least one activation parameter of the motor, for example rotation speed and/or rotation duration, optionally when activating the motor in a power saving mode. In some embodiments, the control circuitry prevents the activation of the motor when the battery power level is lower than a predetermined value.

According to some embodiments, the power level in the battery when the battery is fully charged is sufficient for at least one dialysis treatment session, for example 2 treatment sessions, 3 treatment sessions, 4 treatment sessions or any smaller, intermediate or larger number of treatment sessions. In some embodiments, a treatment session includes at least partly draining of dialysate from the peritoneal cavity and at least partly infusion of fresh dialysate into the peritoneal cavity. Alternatively, a treatment session includes at least partly draining of dialysate from the peritoneal cavity, at least partly infusion of fresh dialysate into the peritoneal cavity and the dwelling time of the dialysate within the peritoneal cavity.

Optionally, the dialysis device does not include a heater, for example a dialysate heater. In some embodiments, the dialysis device does not include the heater, for example to save battery power and/or to lower the overall weight of the dialysis system.

According to some embodiments the weight of the dialysis device is in a range of 500 gr to 5 kg (5000 gr), for example 1 kg, 1.5 kg, 2 kg, 2.5 kg or any intermediate smaller or larger weight. Optionally the weight of the dialysis system is below 4000 gr. In some embodiments, the length of the device is in a range of 100 mm to 450 mm, for example 100 mm, 150 mm, 170 mm, 200 mm or any intermediate, smaller or larger value. In some embodiments, the width of the device is in a range of 80 mm to 300 mm, for example 100 mm, 130 mm, 150 mm or any intermediate, smaller or larger value.

According to some embodiments, the dialysis device comprises at least one connecting member, for example a harness, a belt or an adaptor, configured to secure the system to at least one body part of the patient, for example to the hips, leg, shoulder or thigh.

Exemplary Peritoneal Dialysis System with a Detachable Module

Figure 14A:
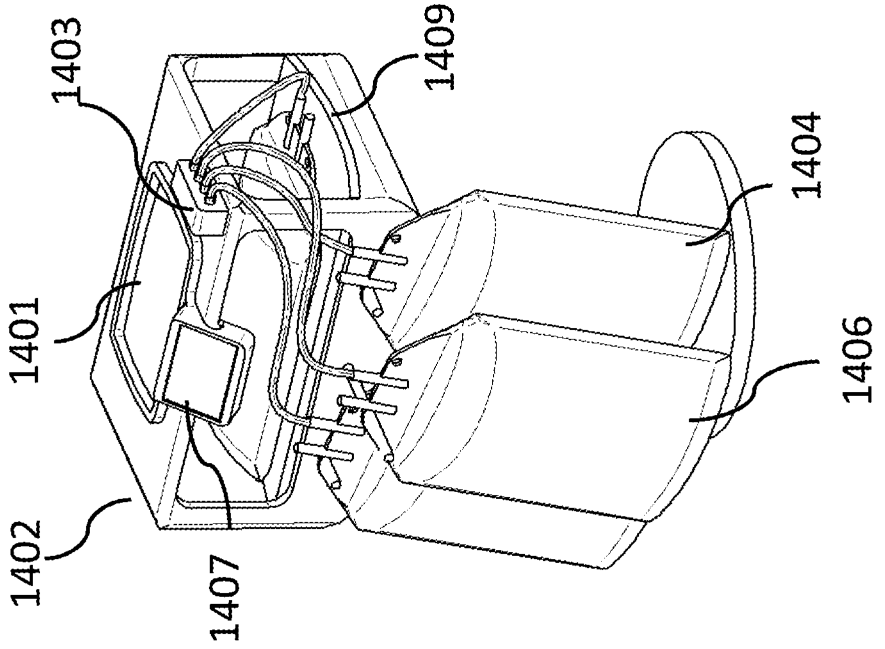
Figure 14B:
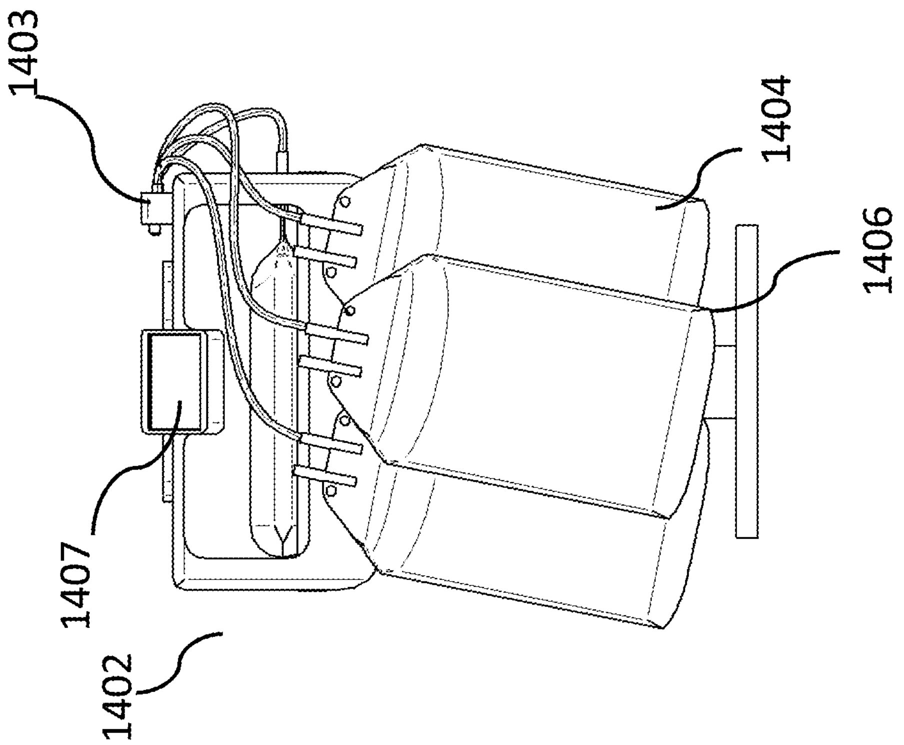

Reference is now made to FIGS. 14A and 14B depicting a peritoneal dialysis cycler base, according to some embodiments of the invention. In some embodiment, cycler base 1402 comprises a receiving interface 1401 configured to facilitate the operable coupling of a detachable dialysis device to the cycler base 1402. The detachable dialysis device will be further illustrated in FIG. 14C-D under reference numeral 1408.

According to some exemplary embodiments, a peritoneal dialysis cycler base, for example cycler base 1402 comprises a base with a control unit 1407, and a tubing connector 1403 which allows, for example fluidically connection of at least one bag, for example bags 1406 and 1404 to the cycler base 1402. In some embodiments, each of the bags are connected to the cycler base 1402 by a hook or an anchoring mechanism, which for example prevents the detachment of the bag from the cycler base. In some embodiments, the cycler base 1402 comprises a temperature monitoring and/or control module, for example module 1409 for monitoring the fluid temperature within the bags and/or to heat the fluid if necessary.

Figure 14C:
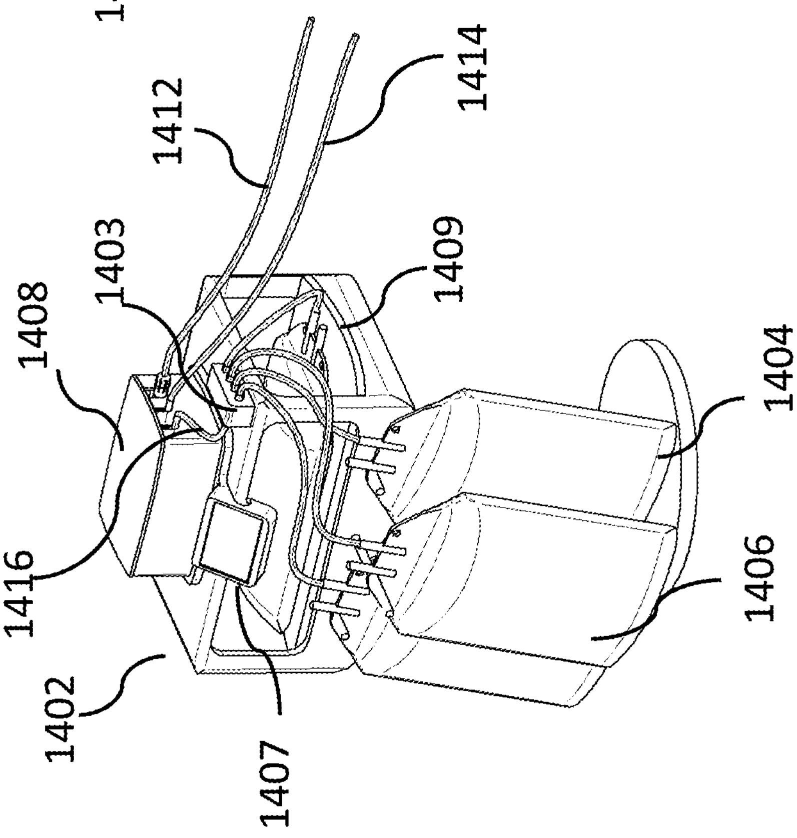
Figure 14D:
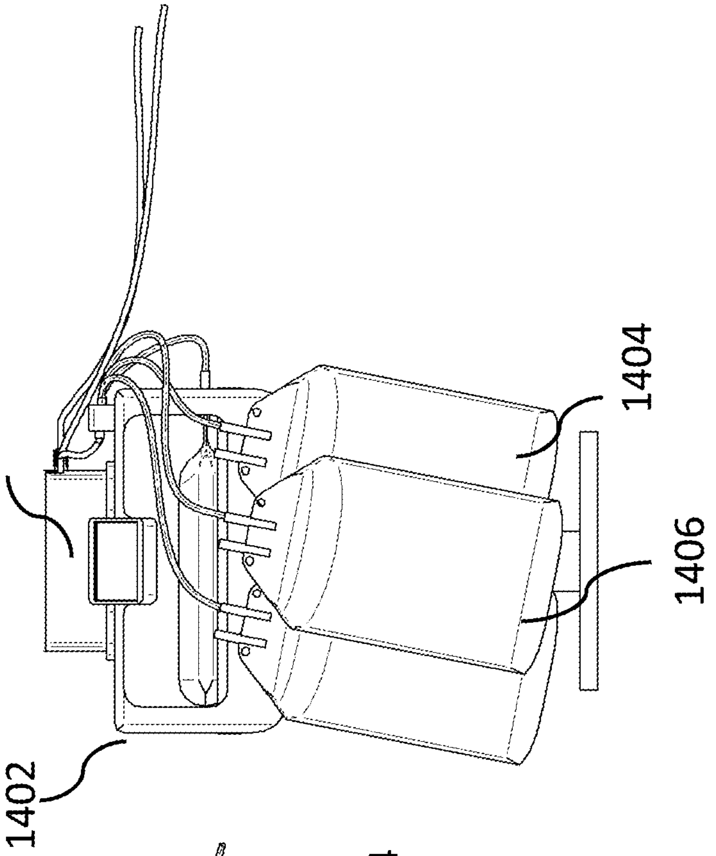

According to some exemplary embodiments, the cycler base 1402 is controlled automatically or semi-automatically by control unit 1407. In some embodiments, cycler base controls the temperature of the fluid in the bags or the fluid that flows through the tubing Reference is now made to FIGS. 14C and 14D depicting a detachable and optionally portable peritoneal dialysis device, according to some embodiments of the invention.

According to some exemplary embodiments, a detachable dialysis device 1408 comprises at least two connectors for an infusion tube 1412 and for a draining tube 1414, and at least one connector for fluidically connecting the dialysis device 1408 with the tubing connector 1403 of the cycler base 1402. In some embodiments, when a treatment session is over, for example an infusion or a draining session the patient disconnects tube 1416 which fluidically connects the detachable device 1408 and the cycler base 1402. In some embodiments, the detachable device 1408 is connected to the cycler base 1402 by wireless connection, for example Wi-Fi, Bluetooth or infra-red connection. Alternatively, the detachable device 1408 is connected to the cycler base 1402 by a communication plug.

According to some exemplary embodiments, the detachable device 1408 receives from the control unit 1407 of the cycler device 1402 information regarding the number of bags connected to the cycler device and/or their content. In some embodiments, the detachable device 1408 selects a specific bag from the bags connected to the cycler base 1402 for dialysate infusion, based on a determined treatment protocol or according to determined treatment parameters. In some embodiments, when draining dialysate the detachable device 1408 signals the cycler base 1402 to direct the draining fluid flow to a selected bag connected to the cycler base.

It is expected that during the life of a patent maturing from this application many relevant devices for monitoring and controlling a peritoneal dialysis treatment will be developed; the scope of the term peritoneal dialysis device is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A peritoneal dialysis system, comprising:

a peritoneal dialysis cycler base, and a portable peritoneal dialysis device, wherein the peritoneal dialysis cycler base is configured to detachably receive the portable peritoneal dialysis device wherein the portable peritoneal dialysis device is configured to operably couple with a patient for performing peritoneal dialysis, whether it is detached from, or docked with, the peritoneal dialysis cycler base;

and wherein the peritoneal dialysis cycler base comprises:

a control unit; and a tubing connector which allows fluidically connecting at least one fresh dialysate bag and/or at least one drain bag to the peritoneal dialysis cycler base; and wherein, when the portable peritoneal dialysis device is detachably received by the peritoneal dialysis cycler base, the portable peritoneal dialysis device is in operable communication with the peritoneal dialysis cycler base.

2. The peritoneal dialysis system according to claim 1, wherein the peritoneal dialysis cycler base comprises a temperature monitoring and/or a control module to control a fluid temperature within the at least one fresh dialysate bag and/or to heat the fluid in the at least one fresh dialysate bag if necessary and/or to automatically or semi-automatically control the fluid temperature that flows through tubing of the portable peritoneal dialysis device and/or controls the fluid temperature in the at least one fresh dialysate bag.

3. The peritoneal dialysis system according to claim 1, wherein the portable peritoneal dialysis device comprises at least two connectors for an infusion tube and for a draining tube; and at least one connector for fluidically and removably connecting the portable peritoneal dialysis device with the tubing connector of the peritoneal dialysis cycler base.

4. The peritoneal dialysis system according to claim 1, wherein the control of the peritoneal dialysis cycler base is configured to provide the portable peritoneal dialysis device with information about a number of bags connected to the peritoneal dialysis cycler base and/or a bag content.

5. The peritoneal dialysis system according to claim 1, wherein the system is configured to allow selecting through the portable peritoneal dialysis device a specific bag from a plurality of bags connected to the peritoneal dialysis cycler base for dialysate infusion, based on a determined treatment protocol or according to determined treatment parameters.

6. The peritoneal dialysis system according to claim 1, wherein the peritoneal dialysis cycler base and the portable peritoneal dialysis device are configured to perform wired or wireless communication with each other.

7. The peritoneal dialysis system according to claim 1, wherein the system is configured to receive a communication signal from the portable peritoneal dialysis device to direct a draining fluid flow to a selected drain bag connected to the peritoneal dialysis cycler base.

8. The peritoneal dialysis system according to claim 1, further comprising:
a bag switcher to which the portable peritoneal dialysis device is adapted to be detachably connected during a peritoneal dialysis treatment,
wherein the bag switcher is configured to validate that a correct bag is connected.

9. The peritoneal dialysis system according to claim 8,
wherein the controller signals the bag switcher to switch the dialysate bag to a bag with a desired dialysate temperature.

10. A peritoneal dialysis cycler base,
wherein the peritoneal dialysis cycler base is configured to detachably receive a portable peritoneal dialysis device and wherein the peritoneal dialysis cycler base comprises:
a control unit; and
a tubing connector which allows fluidically connecting at least one fresh dialysate bag and/or at least one drain bag to the peritoneal dialysis cycler base;
wherein the portable peritoneal dialysis device is configured to operably couple with a patient for performing peritoneal dialysis, whether it is detached from, or docked with, the peritoneal dialysis cycler base; and
wherein, when the portable peritoneal dialysis device is detachably received by the peritoneal dialysis cycler base, the portable peritoneal dialysis device is in operable communication with the peritoneal dialysis cycler base.

11. The peritoneal dialysis cycler base according to claim 10, further comprising:
a temperature monitoring and/or a control module to control a fluid temperature within the at least one fresh dialysate bag and/or to heat the fluid in the at least one fresh dialysate bag if necessary and/or to automatically or semi-automatically control the fluid temperature that flows through tubing of the portable peritoneal dialysis device and/or controls the fluid temperature in the at least one fresh dialysate bag.

12. The peritoneal dialysis cycler base according to claim 10, further comprising:
at least one connector for fluidically connecting, in a removable manner, the portable peritoneal dialysis device with the tubing connector of the peritoneal dialysis cycler base.

13. The peritoneal dialysis cycler base according to claim 10, wherein the control of the peritoneal dialysis cycler base is configured to provide the portable peritoneal dialysis device with information about a number of bags connected to the peritoneal dialysis cycler base and/or a bag content.

14. The peritoneal dialysis cycler base according to claim 10, wherein the peritoneal dialysis cycler base is configured to allow selecting, through the portable peritoneal dialysis device that is detachable from the peritoneal dialysis cycler base, a specific bag from a plurality of bags connected to the peritoneal dialysis cycler base for dialysate infusion, based on a determined treatment protocol or according to determined treatment parameters.

15. The peritoneal dialysis cycler base according to claim 10, wherein the peritoneal dialysis cycler base is configured for wired or wireless communication with the portable peritoneal dialysis device.

16. The peritoneal dialysis cycler base according to claim 10, wherein the peritoneal dialysis cycler base is configured to receive a signal from the portable peritoneal dialysis device to direct a draining fluid flow to a selected drain bag connected to the peritoneal dialysis cycler base.

17. The peritoneal dialysis cycler base according to claim 10, further comprising:
a memory which stores at least one treatment protocol; and
a control circuitry connected to the memory, wherein the control circuitry generates a report and/or modifies the treatment if an outcome of a treatment is not a desired outcome of the treatment protocol.

* * * * *